United States Patent [19]

Yukio et al.

[11] Patent Number: 4,983,520

[45] Date of Patent: Jan. 8, 1991

[54] DNA SEQUENCE ENCODING MODIFIED HEPATITIS B VIRUS SURFACE ANTIGEN P31 PROTEIN

[75] Inventors: Fujisawa Yukio, Kobe; Itoh Yasuaki, Nishinomiya; Nishimura Osamu, Kawanishi; Fujii Tomoko, Toyonaka, all of Japan

[73] Assignee: Takeda Chemical Industries, Ltd., Osaka, Japan

[21] Appl. No.: 898,425

[22] Filed: Aug. 20, 1986

[30] Foreign Application Priority Data

Aug. 20, 1985 [JP] Japan .................................. 60-183344
Jan. 10, 1986 [JP] Japan .................................... 61-4090
Jan. 10, 1986 [JP] Japan .................................... 61-4091
Jun. 2, 1986 [JP] Japan ................................. 61-128918

[51] Int. Cl.$^5$ .......................... C12N 1/13; C12N 1/19; C12N 7/00; C12N 15/11; C12N 15/34; C12N 15/81; A61K 39/00
[52] U.S. Cl. ................................. 435/69.3; 435/711; 435/91; 435/170; 435/171; 435/172.1; 435/172.3; 435/235; 435/252.3; 435/259; 435/320; 435/940; 536/27; 935/10; 935/22; 935/55; 935/60; 935/66; 424/88
[58] Field of Search ................... 536/27; 435/69.3, 91, 435/171, 170, 172.1, 172.3, 235, 236, 254, 255, 256, 320; 424/940, 88; 935/6, 9, 10, 11, 12, 22, 24, 28, 33, 37, 52, 55, 56, 59, 60, 66, 69

[56] References Cited

U.S. PATENT DOCUMENTS 4,428,941 1/1984 Galibert et al. ..................... 424/177
4,650,674 3/1987 Aggarwal et al. .................... 424/85

OTHER PUBLICATIONS

Michel et al., 1984, *PNAS* 81:7708–7712.
Sanchez et al., 1981, *Virology* 114(1):71–80.
Nature, 298, 347–350 (1882).
5—A Hepatitis-B Surface Antigen Polypeptide (P31) with the Receptor for Polymerized Human as Well as Chimpanzee Albumins, A. Machida et al.; Gastroenterology, Jul.–Dec. 1983, vol. 85, pp. 268–274.
6—A Polypeptide Containing 55 Amino Acid Residues Coded by the Pre-S Region of Hepatitis-B Virus Deoxyribonucleic Acid Bears the Receptor for Polymerized Human as Well as Chimpanzee Albumins, A. Machida et al.; Gastroenterology, May 1984, vol. 81, No. 5, pp. 910–918.
1—Synthesis and Assembly in Yeast of Hepatitis-B Surface Antigen Particles Containing the Polyalbumin Receptor, Pablo Valenzuela et al.; Bio/Technology, vol. 3, Apr. 1985, pp. 317–320.
Science, vol. 213, No. 4506, Tiollais et al., pp. 406–411.

*Primary Examiner*—Richard A. Schwartz
*Assistant Examiner*—Richard C. Peet
*Attorney, Agent, or Firm*—David G. Conlin; Linda M. Buckley

[57] ABSTRACT

A modified protein (i) derived from a hepatitis B virus surface antigen P31 protein and (ii) having hepatitis B virus surface antigen activity and the ability to bind polymerized human serum albumin, wherein the modification comprises rendering at least one trypsin-like protease sensitive site of the hepatitis B virus surface antigen P31 protein insensitive. The modified protein can be used in the production of a vaccine for prevention of hepatitis B virus infections and as an antigen for diagnosis of hepatitis B virus infections.

51 Claims, 21 Drawing Sheets

```
                                ATG CAG TGG AAT TCC ACA ACA TTC CAC CAA GCT
  1                             Met Gln Trp Asn Ser Thr Thr Phe His Gln Ala

CTG CTA GAT CCC AGA GTG AGG GGC CTA TAT TTT CCT GCT GGT GGC TCC AGT TCC
  12  Leu Leu Asp Pro Arg Val Arg Gly Leu Tyr Phe Pro Ala Gly Gly Ser Ser Ser

GGA ACA GTA AAC CCT GTT CCG ACT ACT GCC TCA CCC ATA TCG TCA ATC TTC TCG
  30  Gly Thr Val Asn Pro Val Pro Thr Thr Ala Ser Pro Ile Ser Ser Ile Phe Ser

AGG ACT GGG GAC CCT GCA CCG AAC ATG GAG AAC ACA ACA TCA GGA TTC CTA GGA
  48  Arg Thr Gly Asp Pro Ala Pro Asn Met Glu Asn Thr Thr Ser Gly Phe Leu Gly

CCC CTG CTC GTG TTA CAG GCG GGG TTT TTC TTG TTG ACA AGA ATC CTC ACA ATA
  66  Pro Leu Leu Val Leu Gln Ala Gly Phe Phe Leu Leu Thr Arg Ile Leu Thr Ile

CCA CAG AGT CTA GAC TCG TGG TGG ACT TCT CTC AAT TTT CTA GGG GGA GCA CCC
  84  Pro Gln Ser Leu Asp Ser Trp Trp Thr Ser Leu Asn Phe Leu Gly Gly Ala Pro

ACG TGT CCT GGC CAA AAT TCG CAG TCC CCA ACC TCC AAT CAC TCA CCA ACC TCT
 102  Thr Cys Pro Gly Gln Asn Ser Gln Ser Pro Thr Ser Asn His Ser Pro Thr Ser

TGT CCT CCA ATT TGT CCT GGC TAT CGC TGG ATG TGT CTG CGG CGT TTT ATC ATA
 120  Cys Pro Pro Ile Cys Pro Gly Tyr Arg Trp Met Cys Leu Arg Arg Phe Ile Ile

TTC CTC TTC ATC CTG CTG CTA TGC CTC ATC TTC TTG TTG GTT CTT CTG GAC TAC
 138  Phe Leu Phe Ile Leu Leu Leu Cys Leu Ile Phe Leu Leu Val Leu Leu Asp Tyr

CAA GGT ATG TTG CCC GTT TGT CCT CTA CTT CCA GGA ACA TCA ACC ACC AGC ACG
 156  Gln Gly Met Leu Pro Val Cys Pro Leu Leu Pro Gly Thr Ser Thr Thr Ser Thr

GGG CCA TGC AAG ACC TGC ACG ATT CCT GCT CAA GGA ACC TCT ATG TTT CCC TCT
 174  Gly Pro Cys Lys Thr Cys Thr Ile Pro Ala Gln Gly Thr Ser Met Phe Pro Ser

TGT TGC TGT ACA AAA CCT TCG GAC GGA AAC TGC ACT TGT ATT CCC ATC CCA TCA
 192  Cys Cys Cys Thr Lys Pro Ser Asp Gly Asn Cys Thr Cys Ile Pro Ile Pro Ser

TCC TGG GCT TTC GCA AGA TTC CTA TGG GAG TGG GCC TCA GTC CGT TTC TCC TGG
 210  Ser Trp Ala Phe Ala Arg Phe Leu Trp Glu Trp Ala Ser Val Arg Phe Ser Trp

CTC AGT TTA CTA GTG CCA TTT GTT CAG TGG TTC GTA GGG CTT TCC CGC ACT GTT
 228  Leu Ser Leu Leu Val Pro Phe Val Gln Trp Phe Val Gly Leu Ser Pro Thr Val

TGG CTT TCA GTT ATA TGG ATG ATG TGG TAT TGG GGG CCA AGT CTG TAC AAC ATC
 246  Trp Leu Ser Val Ile Trp Met Met Trp Tyr Trp Gly Pro Ser Leu Tyr Asn Ile

TTG AGT CCC TTT TTA CCT CTA TTA CCA ATT TTC TTT TGT CTT TGG GTA TAC ATT
 264  Leu Ser Pro Phe Leu Pro Leu Leu Pro Ile Phe Phe Cys Leu Trp Val Tyr Ile

TAA
 282  ***
```

FIG. 2

```
             41  42  43  44  45  46  47  48  49  50  51  52  53  54
pTRP P31-R  --- CCC ATA TCG TCA ATC TTC TCG AGG ACT GGG GAC CCT GCA CCG --
            --- Pro Ile Ser Ser Ile Phe Ser Arg Thr Gly Asp Pro Ala Pro --
```

```
pTRP P31-Ra --- CCC ATA TCG TCA ATC TTC /// /// ACT GGG GAC CCT GCA CCG --
            --- Pro Ile Ser Ser Ile Phe╗       ╔Thr Gly Asp Pro Ala Pro --
                                      ╲CCG GAT CCG GGG╱
                                       Pro Asp Pro Gly
```

FIG. 3

```
             41  42  43  44  45  46  47  48  49  50  51  52  53  54
pTRP P31-R  --- CCC ATA TCG TCA ATC TTC TCG AGG ACT GGG GAC CCT GCA CCG --
            --- Pro Ile Ser Ser Ile Phe Ser Arg Thr Gly Asp Pro Ala Pro --
```

```
pTRP P31-Rb --- CCC ATA TCG T// /// /// /// /GG ACT GGG GAC CCT GCA CCG --
            --- Pro Ile Ser         Trp         Thr Gly Asp Pro Ala Pro --
```

```
pTRP P31-Rc --- CCC ATA TC/ /// /// /// /// /// //T GGG GAC CCT GCA CCG --
            --- Pro Ile             Ser                 Gly Asp Pro Ala Pro --
```

FIG. 4

DNA SEQUENCE ENCODING MODIFIED HEPATITIS B VIRUS SURFACE ANTIGEN P31 PROTEIN

FIELD OF INDUSTRIAL UTILITY

This invention relates to novel proteins useful as vaccines and a method of producing the same.

BACKGROUND ART

Type B hepatitis is a viral disease which occurs frequently in particular in the tropics of Africa, in Southeast Asia and in the Far East. Hepatitis B is suggested to be causative of chronic hepatitis or hepatic cirrhosis or, further, primary liver cancer. The pathogen is hepatitis B virus (hereinafter abbreviated as "HBV"), which is one of the DNA viruses. Occurring as a spherical particle having a diameter of 42 nm, it is called "Dane particle" after the discoverer. In the outer layer, there is HBV surface antigen (hereinafter abbreviated as "HBsAg"). It includes subtypes adr, adw, ayr, ayw and so on, which differ in antigenicity. The subtypes adw and adr are common in Japan.

In the blood of patients with hepatitis B, there are also detected smaller particles and tubular particles besides Dane particles. These particles have been shown to contain the same type of HBsAg as found in the Dane particle. For other viruses, it is known that an antibody to the surface antigen of a virus can prevent infection with said virus. In the case of HBV, it may be anticipated that a vaccine against hepatitis B might be produced based on HBsAg. However, human and chimpanzee alone are susceptible to HBV infection. Attempts to infect cultured cells have been unsuccessful. Therefore, the source of HBsAg is limited to the blood of infected human patients. While the small and other particles obtained may meet the demand therefor as a material for preparing diagnostic reagents, the supply is still insufficient for large-scale vaccine production.

Recent advances in molecular biology have made it possible to transform bacteria by introducing thereinto a DNA coding for a nonbacterial protein. If the structural gene for HBsAg (hereinafter abbreviated as "HBsAg gene") can be expressed in bacteria as a result of the use of this gene manipulation technique, it will become possible to produce HBsAg, substantially free from the risk of HBV infection, in large quantities and to open a way to practical use of hepatitis B vaccine.

For the subtype ayw found predominantly in Europe and America among the currently known four subtypes adw, adr, ayw and ayr, the locus and base sequence of the HBsAg gene have been determined [Galibert, F. et al., Nature, 281, 646 (1979); Charnay, P. et al., Nucleic Acids Res., 7, 335 (1979)] and its expression as a hybrid protein in *Escherichia coli* has been reported [Charnay, P. et al., Nature, 286, 893 (1980); Edman, J. C. et al., Nature, 291, 503 (1981)].

For the subtypes adw and adr, which are frequently found in Japan, some of the present inventors have succeeded in constructing a DNA containing the HBsAg gene, determined the DNA base sequence of said gene and the locus thereof on the genome, and opened a way to large-scale HBsAg production by cultivation of a transformant carrying this recombinant DNA (Japanese Unexamined Patent Publication Nos. 194897/1983, 201796/1983 and 74985/1984).

As recently reported by Machida, A. et al. [Gastroenterology, 85, 268 (1983); ibid., 86, 910 (1984)], the HBsAg small particles obtained from the plasma of hepatitis B virus e antigen-positive patients have been shown to contain a P31 protein (molecular weight: 31 kilodaltons) and a P35 protein (a conjugated protein with a sugar joined to P31; molecular weight: 35 kilodaltons) in addition to those principal peptides so far identified, such as P-I (molecular weight: 22-24 kilodaltons) and P-II (molecular weight: 25-29.5 kilodaltons) [Peterson, D. L. et al., Proc. Natl. Acad. Sci. U.S.A., 74, 1530 (1977)]. P31 is composed of P-I and 55 amino acid residues encoded by the Pre-S region joined to the N-terminus of P-I, and the presence of a polymerized human serum albumin (poly-HSA) receptor in this region has been established. The above-cited report published in 1984 shows that the above P31 protein has a sugar chain. On the other hand, it is considered that the Dane particle adheres to the hepatocyte via poly-HSA for enabling proliferation since poly-HSA and the receptor therefor are present also on the hepatocyte surface. Therefore it is expected that successful masking of the poly-HSA receptor on the Dane particle with an antibody to P31 would prevent said particle from binding to the hepatocyte, hence would contribute to more effective prevention of HBV infection.

On the other hand, restrictive hydrolysis of P31 with various proteases, for example trypsin, cleaves P31 selectively at the site of the 48th amino acid (arginine) residue from the N-terminus, giving a protein (P28) having a molecular weight of 28 kilodaltons. Also in the case of P31 gene expression in *Saccharomyces cerevisiae*, a tendency is seen toward decomposition of the gene product due to the presence of a large quantity of trypsin-like protease in yeast cells, which leads to formation of P28 (FIG. 1). In addition to this P28, 30-, 21- and 19-kilodalton proteins, among others, may possibly be formed as a result of decomposition of the 16th and 18th arginine residues and the 177th and 196th lysine residues from the N-terminus of P31 in the presence of trypsin-like protease in the yeast.

As mentioned above, the HBsAg particles obtained from the plasma of hepatitis B virus e antigen-positive patients contain a P31 protein and a P35 protein (a conjugated protein with a sugar joined to P31; molecular weight: 35 kilodaltons) in addition to principal peptides such as P-I and P-II [Stibbe, W. et al., J. Virol., 46, 626(1983)]. In particular, the main body of the infections HBV named as Dane particle possesses P31 protein and P35 protein besides P-I and P-II as surface antigens. It would be more effective to use plural antigens found in HBV than to use a single antigen as a vaccine material. That is, a preferable vaccine should have P31 protein and P35 protein as well as P-I and P-II. Although production of vaccine against hepatitis B virus by recombinant DNA techniques has been attempted, only Michel, M. L. et al report [Proc. Natl. Acad. Sci. U.S.A., 81, 708 (1984); Bio/Technology, 3, 561(1985)]a vaccine material that contains plural antigens found in HBV. However, their methods require the use of an animal cell as a host which suffers the disadvantage of being very costly.

DISCLOSURE OF THE INVENTION

This invention provides:

(1) A modified P31 protein having hepatitis B virus surface antigen activity and ability to bind polymerized human serum albumin which is derived from a hepatitis B virus surface antigen P31 protein by such modification as to render at least one trypsin-like protease sensitive site thereof insensitive;

(2) A DNA which contains a DNA coding for a modified P31 protein having hepatitis B virus surface antigen activity and ability to bind polymerized human serum albumin which is derived from a hepatitis B virus surface antigen P31 protein by such modification as to render at least one trypsin-like protease sensitive site thereof insensitive;

(3) A transformant carrying a DNA which contains a DNA coding for a modified P31 protein having hepatitis B virus surface antigen activity and ability to bind polymerized human serum albumin which is derived from a hepatitis B virus surface antigen P31 protein by such modification as to render at least one trypsin-like protease sensitive site thereof insensitive;

(4) A method of producing a modified P31 protein having hepatitis B virus surface antigen activity and ability to bind polymerized human serum albumin which is derived from a hepatitis B virus surface antigen P31 protein by such modification as to render at least one trypsin-like protease sensitive site thereof insensitive, which comprises cultivating a transformant carrying a DNA which contains a DNA coding for said modified P31 protein and isolating from the culture said modified P31 protein produced and accumulated therein; and (5) A method of producing (i) a modified P31 protein having hepatitis B virus surface antigen activity and ability to bind polymerized human serum albumin which is derived from a hepatitis B virus surface antigen P31 protein by such modification as to render at least one trypsin-like protease sensitive site thereof insensitive, and (ii) a hepatitis B virus surface antigen P25 protein, which method comprises cultivating a transformant carrying a DNA which contains a DNA coding for said modified P31 protein and a DNA coding for said P25 protein. The products and methods of the present invention offer advantages over vaccines known in the art in terms of risk of infection and cost of production.

The trypsin-like protease is a yeast protease capable of digesting a peptide chain between Arg and X and between Lys and X (X is an amino acid residue).

The modified P31 protein of the present invention is hardly decomposed with the trypsin-like protease, and, therefore, it is easier to extract and purify the modified P31 protein expressed in a yeast without decomposition by the trypsin-like protease.

The DNA coding for the modified P31 protein according to the invention may be for any subtype (adr, adw, ayr, ayw) and can be prepared, for example, by the the following method.

The plasmid pBR322-BamHI/HBr330 (hereinafter abbreviated as "pHBr330") containing the 3.19 kb adr-type HBV DNA [described in Japanese Unexamined Patent Publication No. 74985/1984 or Nucleic Acids Res., 11, 1747 (1983)]inserted therein was double-digested with the restriction enzymes EcoRI and BamHI to give a 1398 bp DNA fragment containing a part of the pre-S region. A P31-encoding DNA is produced by joining an appropriate adaptor containing the sequence $$\begin{bmatrix} 5'\text{ATGCAGTGG}3' \\ 3'\text{TACGTCACCTTAA}5' \end{bmatrix}$$

to the above fragment and inserted into an appropriate vector.

DNAs coding for other subtypes of P31 can be prepared in the same manner as mentioned above.

For example, by the following method, there may be produced a DNA coding for a modified P31 protein lacking in the 48th amino acid (arginine) or a peptide chain containing said arginine from the N-terminus of P31, which is one of those sites that are sensitive to trypsin-like protease, or containing another amino acid or peptide chain substituting for said arginine or said arginine-containing peptide chain.

In the case of the subtype adr P31 gene, a site capable of recognizing the restriction enzyme XhoI is present in the region coding for the arginine which is the 48th amino acid from the N-terminus, as shown in FIG. 2. Therefore, the arginine codon can be eliminated by cleaving the P31 gene using XhoI and then removing the arginine-encoding region using an exonuclease, such as nuclease BAL31 or by cleaving the P31 gene using XhoI, repairing the XhoI cleavage site with a DNA polymerase large fragment and inserting an appropriate linker. From among the products, one which is in phase with respect to the gene reading frame is to be selected.

The DNA coding for the modified P31 protein may be chemically synthesized. In that case, the synthesis is carried out such that the sequence coding for the 48th amino acid arginine or a peptide chain containing the same is either missing or substituted for by such codon or codons as coding for some other amino acid or a peptide and, in addition, such that the reading frame is kept in phase.

Furthermore, a 267 bp DNA fragment obtained by digestion of the plasmid pBR-Sal-6 shown in FIG. 5 with the restriction enzymes SalI and XbaI is inserted into the vector M13mpII at its SalI-XbaI site and the resultant product is used for the infection of *Escherichia coli* JM103 (Pharmacia P-L Biochemicals). After growing, the M13 phage released into the broth is precipitated with polyethylene glycol and then treated with phenol to give the single-strand M13 phage DNA.

Then, a primer for converting the codon AGG for the 48th amino acid arginine from the N-terminus of P31 into, for example, the codon CAG for glutamine, such as d$^{5'}$(CCCAGTCTGCGAGAAG)$^{3'}$, can be prepared by chemical synthesis. This primer and the previously prepared M13 DNA are mixed with each other. After rendering double-stranded under the action of DNA polymerase I large fragment, the product can be cyclized in the presence of T4 DNA ligase. This circular DNA is introduced into *Escherichia coli* JM103, the M13 phage DNA released on a plate is transferred onto a filer and subjected to plaque hybridization using said synthetic primer labeled with $^{32}$P [Maniatis, T. et al., Molecular Cloning, A Laboratory Manual, Cold Spring Harbor Laboratory, p. 312 (1982)]. Digestion with the restriction enzymes SalI-XbaI of the DNA prepared from the phage for which a strong signal is detectable can give a 267 bp DNA fragment. Substitution of said fragment for the 267 bp SalI-XbaI fragment from the plasmid pBR-Sal-6 gives a DNA coding for a modified P31 protein (modified P31 gene).

Since no XhoI recognition site is present on the DNA coding for the subtype adw P31 or the subtype adyw P31, the gene for the relevant modified P31 can be produced by the technique of site-directed mutagenesis [Smith, M. and Gillam, S., Genetic Engineering, 3, 1 (1982)] as mentioned above.

A plasmid DNA, cosmid DNA, phage DNA or the like containing the whole or a part of the HBsAg gene can be used as a template DNA for said site-directed mutagenesis. The M13 phage DNA and φX174 phage DNA are desirable for a template DNA since the single-strand DNA can be prepared easily. When the M13 phage or φX174 phage with the whole or a part of the HBsAg gene inserted therein, for instance, is used, the single-strand DNA originally occurring within the phage particles can be recovered by precipitation of the phage particles occurring in the culture broth with polyethylene glycol, deproteinizing treatment with phenol and precipitation with ethanol. When a double-strand plasmid DNA or cosmid DNA with the whole or a part of the HBsAg gene inserted therein is used as the template DNA, the double-strand DNA can be converted to the single-strand DNA prior to use thereof by heat-treating the double-strand DNA at 100° C. for 1 to 10 minutes, preferably 3 to 5 minutes, followed by quenching with ice water.

The primer for site-directed mutagenesis may have any DNA sequence which has a desirably modified DNA sequence and can be hybridized with the template DNA and thus function as a primer in DNA synthesis. It is desirable to prepare a single-strand DNA having an appropriate sequence by chemical synthesis, although any method may be applicable to the preparation of said primer.

Such primer and the previously prepared single-strand DNA are mixed together and a double-strand DNA is restored under the action of DNA polymerase I large fragment. The double-strand DNA can be cyclized under the action of T4 DNA ligase. This circular DNA is introduced into Escherichia coli. The desired mutant can be selected by plaque hybridization [Maniatis, T. et al., Molecular Cloning, A Laboratory Manual, Cold Spring Harbor Laboratory, p. 312 (1982)]or colony hybridization [ibid., p. 326] using a radioisotope-labeled primer as the probe. A phage DNA or plasmid DNA is prepared from the thus-obtained plaque or colony. A modified P31 gene can be constructed using said DNA.

For eliminating the 48th amino acid (arginine) from the N-terminus or a peptide containing the same, DNA construction may be made either such that the 48th amino acid arginine alone becomes missing or such that a peptide containing the 48th amino acid arginine becomes missing. The size of the missing peptide is optional provided that the HBsAg activity and the ability to bind polymerized human serum albumin can be retained without said peptide. Preferably, however, a peptide containing the 48th amino acid arginine within the range of the peptide chain covering the 26th–55th (from the N-terminus) amino acids, more preferably a peptide containing the 48th amino acid arginine within the range of the peptide chain covering the 44th–49th amino acids, should be missing.

In place of the missing 48th amino acid arginine or the missing peptide containing said arginine, there may be added an amino acid other than arginine or lysine or a peptide chain. In such case, the additional peptide chain should comprise about 1 to 50 amino acids, preferably about 1 to 4 amino acids.

The codons for the 16th and 18th amino acids (arginine) and the 177th and 196th amino acids (lysine) as counted from the N-terminus can be replaced with codons other than those for lysine and arginine by the above-mentioned technique of site-directed mutagenesis to give a modified P31 gene.

The modification of the above-mentioned trypsin-like protease sensitive site is preferably made at least at the 48th amino acid (arginine) from the N-terminus of P31 or a peptide chain containing said amino acid arginine, and the only modification of the 48th amino acid (arginine) or a peptide chain containing said amino acid arginine is more preferable.

The codons for other amino acids than lysine and arginine which are to be used for the above-mentioned addition or substitution are, for example, codons for asparagine, aspartic acid, alanine, isoleucine, glycine, glutamine, glutamic acid, cysteine, serine, tyrosine, tryptophan, threonine, valine, histidine, phenylalanine, proline, methionine and leucine.

A recombinant DNA capable of expression of the modified P31-encoding DNA can be constructed by insertion of this modified P31-encoding DNA at the 3′ end of a promoter region capable of functioning in one or more of various hosts (e.g. *Escherichia coli, Bacillus subtilis,* yeast, animal cells).

The promoter region may be any promoter region provided that it contains a site which is necessary for RNA polymerase binding for the initiation of mRNA synthesis.

When *Escherichia coli*, for instance, is used as the host, a recombinant DNA capable of expression of the modified P31-encoding DNA can be constructed by insertion of the modified P31-encoding DNA at the 3′ end of a promoter capable of functioning in *Escherichia coli*. Thus, for example, the modified P31-encoding DNA is inserted into the expression vectors pTRP 601, pTRP 771, etc , which are disclosed in Japanese Unexamined Patent Publication No. 201796/1983, under the action of T4 DNA ligase. Using this reaction mixture, a strain of *Escherichia coli* (e.g. The strain C600, 294, W3110, RR1l, PR13) is transformed by the known method [Cohen, S. N. et al., Proc. Natl. Acad. Sci. U.S.A., 69, 2110 (1972)] or a modification thereof. The promoter to be used is not necessarily limited to the trp promoter (trp-p) but the recA promoter (Japanese Unexamined Patent Publication No. 65099/1984), lac promoter, $\lambda P_L$ promoter and the like may also be used.

Transformants obtained in the above manner and carrying the novel recombinant plasmid DNA containing the modified P31 protein-encoding DNA can be selected using, for example, the resistance to ampicillin or tetracycline or both as the phenotype. For sorting out a strain carrying the novel recombinant plasmid DNA containing the modified P31 protein-encoding DNA, the following technique, for instance, is used. One chain of the above-mentioned adaptor, namely $^{5'}$AATTCCACTGCATTGTAT$^{3'}$, is radiolabeled using $\gamma$-$^{32}$P-ATP in the presence of T4 polynucleotide kinase and, using this as a probe, a positive clone can reliably be located among the already-obtained drug-resistant transformants by the per se known colony hybridization method [Grunstein, M. and Hogness, D. S., Proc. Natl. Acad. Sci. U.S.A., 72, 3961 (1975)].

A transformant picked out in this manner is cultivated in a per se known medium. As the medium, there may be mentioned, for example, L broth, Penassay broth, or M-9 medium containing glucose and Casamino Acids [Miller, J., Experiments in Molecular Genetics, 431–433 (Cold Spring Harbor Laboratory, New York, 1972)]. For efficient promoter operation, a drug such as 3β-indolylacrylic acid may be added to the medium as necessary.

The cultivation of said transformant is carried out generally at 15°–43° C., preferably at 28°–40° C., for a period of 2–24 hours, preferably for 4–16 hours, if necessary with aeration and/or agitation.

When a yeast, for instance, is used as the host, a yeast transformant can be prepared in the following way. A yeast promoter region such as the repressible acid phosphatase gene promoter region [Meyhack, B. et al., EMBO J., 6, 675 (1982)], glyceraldehyde 3-phosphate dehydrogenase gene promoter region [Holland, J. P. and Holland, M. J., J. Biol. Chem., 255, 2596 (1980)] or 3-phosphoglycerate kinase gene promoter region [Dobson, M. J. et al., Nucleic Acids Res., 10, 2625 (1982)], is inserted into an Escherichia coli-yeast shuttle vector such as YEp13 [Broach, J. R. et al., Gene, 8, 121 (1979)], pSH15 or pSH19 [Harashima, S. et al., Mol. Cell. Biol., 4, 771 (1984)], followed by linking of the modified P31 protein-encoding DNA just behind said promoter region in the presence of T4 DNA ligase. Furthermore, a terminator for terminating transcription can be inserted just behind the modified P31 protein-encoding DNA to thereby increase the yield of the modified P31 protein. As the terminator, there can be used, for example, the 3'-non-coding region of, for example, the 3-phosphoglycerate kinase gene or glyceraldehyde 3-phosphate dehydrogenase gene. The above reaction mixture is used for transforming the above-mentioned host Escherichia coli strain by the above-mentioned method of Cohen et al. The thus-obtained transformant carrying the novel recombinant DNA containing the modified P31 protein-encoding DNA can be selected by using ampicillin resistance, for instance, as the phenotype. A strain carrying the novel recombinant plasmid DNA having the modified P31 protein-encoding DNA can be picked out by using the above-mentioned method in the same manner.

The plasmid DNA is isolated from the thus-selected transformant by the alkaline extraction method [Birnboim, H. C. and Doly, J., Nucleic Acids Res., 7, 1513 (1979)] and then used for transforming a yeast such as a leucine-requiring strain of Saccharomyces cerevisiae, such as AH22R$^-$ (leu2 his4 can1 cir$^+$ pho80) [Proc. Natl. Acad. Sci. U.S.A., 80, 1 (1983)] or AH22R$^-$-derived K33-7B (pho80-AH22, pho8-2) or K33-8D (pho80-AH22, pho8-2 trpl), by the known method [Hinnen, A. et al., Proc. Natl. Acad. Sci. U.S.A., 75, 1927 (1978)] or a modification thereof. The yeast as the host is not limited to these, but Saccharomyces cerevisiae is preferred.

yeast transformant obtained in this manner is cultivated in any suitable medium known to those skilled in the art. As the medium, there xay be mentioned, for example, Burkholder minimum medium [Bostian, K. L. et al., Proc. Natl. Acad. Sci. U.S.A., 77, 4505 (1980)].

The cultivation of the yeast transformant is carried out generally at 15°–40° C., preferably 24°–37° C., for 10–96 hours, preferably 24–72 hours. Aeration and/or agitation can be performed as necessary.

When Bacillus subtilis or an animal cell, for instance, is used as the host, the modified P31 protein can be produced by inserting the modified P31 protein-encoding DNA at the 3' end of a promoter region capable of functioning in Bacillus subtilis or the animal cell, transforming the host with the resultant recombinant DNA by methods known to those skilled in the art and cultivating the obtained transformant. Among the said hosts, a yeast is preferable.

The modified P31 activity of a product can be measured, for example by binding the sample to a cyanogen bromide-activated cellulose paper, followed by reaction with the $^{125}$I-anti-HBsAg antibody of Austria II-125 (Dainabbott) for direct immunoassay [Fujisawa, Y. et al., Nucleic Acids Res., 11, 3581 (1983)].

After cultivation, cells are collected by methods well known to those skilled in the art. In the case of an Escherichia colitransformant, the cells collected are suspended in a buffer solution containing a protein denaturing agent such as urea or guanidine hydrochloride, and the suspension is stirred in the cold and then centrifuged to give a modified P31-containing supernatant; or the cells are suspended in a buffer and then disrupted by sonication, lysozyme and/or freeze-thawing, followed by centrifugation, which gives a modified P31-containing supernatant. Among these and other appropriate methods, however, preferred is the method comprising, for example, harvesting cells, suspending them in a buffer, adding lysozyme, homogenizing the suspension for effecting lysis, adding a buffer containing urea (3–10M), stirring the resulting mixture (at 0°–10° C. for 0.5–8 hours) and conducting centrifugation to give a supernatant.

In the case of a yeast transformant, cells are lysed with Zymolyase (Kirin Brewery) or disrupted by mechanical treatment with glass beads or the like. A surfactant is added thereto, such as Triton X-100 or deoxycholate, and/or a protein denaturing agent, such as urea or guanidine hydrochloride, whereby the modified P31 can be extracted advantageously.

The modified P31-containing extract can be subjected to chromatographic treatment using DEAE-Toyopearl or Butyl-Toyopearl, each equilibrated with 10 mM phosphate buffer containing 10 mM EDTA and 1 mM diisopropylfluorophosphate or another protease inhibitor. The isolation and purification of the modified P31 can also be effected efficiently by affinity chromatographic treatment. The modified P31 adsorbed on these columns can be eluted with a buffer containing a salt in an appropriately defined concentration. As desired, the modified P31-containing eluate fraction collected can be concentrated by ultrafiltration, for instance.

The modified P31 protein is isolated from the above-mentioned extract and at the same time purified by a purification procedure comprising affinity chromatographic treatment.

As the affinity chromatography, there may be mentioned affinity chromatography using polymerized human serum albumin (poly-HSA) as the ligand, and antibody column treatment using an antibody against HBsAg, in particular a monoclonal antibody.

The affinity chromatography using poly-HSA as the ligand is used very advantageously for the purification of modified P31 proteins.

Usable carriers for such affinity chromatography include Formyl-Cellulofine (Seikagaku Kogyo) and Affigel-15 (Bio-Rad), among others. In particular, Formyl-Cellulofine is preferred.

Poly-HSA can be produced by polymerizing human serum albumin with a crosslinking agent (e.g. glutaraldehyde). This is bound to the above-mentioned carrier using, for example, a reducing agent (e.g. NaCNBH$_3$), followed, as desired, by washing. The thus-obtained poly-HSA-bound carrier is generally packed in a column for use in said affinity chromatography.

For the P31 protein purification by affinity chromatography using poly-HSA as the ligand, the above-mentioned P31-containing solution (cell extraction supernatant) is applied to the above-mentioned column equilibrated with a buffer (e.g. phosphate buffer), followed by elution of the adsorbed P31 with a buffer. To said buffer, there can be added a surfactant (e.g. Tween 20) or a protein denaturing agent (urea) or the like in an appropriate amount, and an appropriate eluent can be prepared by combining these additives from the chemical and concentration viewpoint.

A P31 protein-containing eluate fraction is thus collected and, as desired, concentrated by ultrafiltration, for instance.

Said concentrate can be subjected to gel filtration treatment using Sephacryl S-300 or the like. Modified P31 proteins are eluted in the vicinity of the void volume.

Modified P31-containing fractions obtained by a variety of chromatographic procedures can be further purified in such a purification process as sucrose gradient ultracentrifugation or cesium chloride gradient ultracentrifugation.

The DNA coding for the modified P31 protein to be used for production of the modified P31 protein and P25 protein includes the above-mentioned DNA and can be prepared according to the above-mentioned method.

A DNA coding for subtype adw P25 protein (P25 gene) can also be obtained from the plasmid pHBV 933 with a 3.2 kb adw HBV DNA inserted therein described in Japanese Unexamined Patent Publication No. 194897/1983 or Nucleic Acids Res., 11, 1747(1983). The expression plasmid pTRP SS-6[Fujisawa, Y. et al., Nucleic Acids Res. 11, 3581 (1983)] which can express the adw P25 gene (isolated by pHBV 933) in *Escherichia coli* is double-digested with ClaI and PstI to give a 0.82 kb DNA fragment containing the P25 gene. A DNA coding for another subtype P25 can be prepared in the same way as the above-mentioned method. An appropriate linker is added to the DNA fragment and the resulting fragment is inserted in a vector.

It is preferable that the modified P31 and P25 are different in subtype, and more preferable that the modified P31 is adr, the P25 being adw.

A recombinant DNA capable of simultaneous expression of the modified P31 protein and the P25 protein can be constructed by inserting the modified P31 protein-encoding DNA and the P25 protein-encoding DNA, respectively, at the 3' and of promoter regions capable of functioning in one or more of various hosts (e.g. *Escherichia coli, Bacillus subtilis*, yeast, animal cells).

The promoter region may be any promoter region provided that it contains sites which are necessary for the synthesis of mRNA by RNA polymerase.

When *Escherichia coli*, for instance, is used as the host, a recombinant DNA capable of expression of the modified P31-encoding DNA and the P25-encoding DNA can be constructed by inserting the modified P31-encoding DNA and the P25-encoding DNA at the 3' end of promoter(s) capable of functioning in *Escherichia coli*. Using the recombinant DNA, a strain of *Escherichia coli* (e.g. C600, 294, W3110, RR1, PR13) is transformed by the known method [Cohen, S. N. et al., Proc. Natl. Acad. Sci. U.S.A., 69, 2110(1972)] or a modification thereof. The promoter to be used is not necessarily limited to the trp promoter (trp-p) but the recA promoter (Japanese Unexamined Patent Publication No. 65099/1984), lac promoter, $\lambda P_L$ promoter and the like may also be used.

Transformants obtained in the above manner and carrying the novel recombinant plasmid DNA containing the modified P31 protein-encoding DNA and the P25 protein-encoding DNA can be selected using, for example, the resistance to ampicillin or tetracycline or both as the phenotype. For isolating a strain carrying the novel recombinant plasmid DNA containing the modified P31 protein-encoding DNA and the P25 protein-encoding DNA, the above-mentioned techniques are used.

When an yeast, for instance, is used as the host, an yeast transformant can be prepared in the following way. Two (the same or different kind) yeast promoter regions such as the repressible acid phosphatase gene promoter region [Meyhack, B. et al., EMBO J., 6, 675(1982)], glyceraldehyde 3-phosphate dehydrogenase gene promoter region [Holland, J. P. and Holland, M. J., J. Biol. Chem., 255, 2596 (1980)] or 3-phosphoglycerate kinase gene promoter region [Dobson, M. J. et al., Nucleic Acids Res., 10, 2625(1982)], are inserted into an *Escherichia coli*-yeast shuttle vector such as YEp13 [Broach, J. R. et al., Gene, 8, 121(1979)], pSH15 or pSH19 [Harashima, S. et al., Mol. Cell. Biol., 4, 771 (1984)], followed by linking the modified P31 protein-encoding DNA just behind one of said promoter regions and linking the P25 protein-encoding DNA just behind the other promoter region in the presence of T4 DNA ligase. In the same manner as mentioned above, a terminator may be inserted just behind the modified P31 protein-encoding DNA and/or the P25 protein-encoding DNA. The above reaction mixture is used for transforming the above-mentioned host *Escherichia coli* strain by the above-mentioned method of Cohen et al. The obtained transformant carrying the novel recombinant DNA containing the modified P31 protein-encoding DNA and the P25 protein-encoding DNA can be selected by using ampicillin resistance, for instance, as the phenotype marker. A strain carrying the novel recombinant plasmid DNA having the modified P31 protein-encoding DNA and the P25 protein-encoding DNA can be picked out by isolating the plasmid DNA by the alkaline extraction method [Birnboim, H. C. and Doly, J., Nucleic Acids Res., 7, 1513(1979)] and analyzing the size of DNA fragments resulting from treatment of various restriction enzymes by, for instance, agarose gel electrophoresis.

The plasmid DNA is isolated from the selected transformant by the alkaline extraction method [Birnboim, H. C. and Doly, J., Nucleic Acids Res., 7, 1513(1797)] and then used for transformation of an yeast such as a leucine-requiring strain of *Saccharomyces cerevisiae*, such as AH22R$^-$ (leu 2 his 4 can 1 cir$^+$ pho80) [Proc. Natl. Acad. Sci. U.S.A., 80, 1 (1983)] or AH22R$^-$-derived K33-7B (pho80-AH22, pho 8-2) or K33-8D (pho 80-AH22, pho 8-2, trpl), by the known method [Hinnen, A. et al., Proc. Natl. Acad. Sci. U.S.A., 75, 1927(1978)] or a modification thereof. The yeast as the host is not limited to these, but *Saccharomyces cerevisiae* is preferred.

When *Bacillus subtilis* or an animal cell, for instance, is used as the host, the modified P31 protein and the P25 protein can be produced by inserting the modified P31 protein-encoding DNA and the P25 protein-encoding DNA at the 3' end of promoter regions capable of functioning in *Bacillus subtilis* or an animal cell, transforming the host with the recombinant DNA by methods known to those skilled in the art and cultivating the obtained transformant.

The modified P31 and P25 activities of a product can be measured, for example, by Ausria II-125 (Dainabbott) or Auszyme II (Abbott).

The obtained transformant can be cultivated in the same manner as that of the above-mentioned transformant carrying the modified P31 protein-encoding DNA. Extraction of the modified P31 and P25 can be conducted in the same manner as that of the above-mentioned modified P31. Isolation and purification of the modified P31 and P25 from the extract can be conducted by, for example, gel filtration, hydroxyapatite column chromatography, ion exchange column chromatography, ultracentrifugation and/or affinity chromatography using anti-HBsAg antibody.

On the analysis by the Western blotting of the modified P31 DNA product and the P25 DNA product, there are detected a protein of 38-37 kilodaltons (P37) and a protein of 25 kilodaltons (P25). The P37 has a 31 kilodalton-protein to which a sugar chain is bound and has a poly-HSA receptor and HBsAg antigenicity. The P25 has HBsAg antigenicity. The P37 and P25 are extracted from the yeast as an aggregate particle.

The transformant carrying a plasmid with plural antigen genes inserted therein produces a remarkably larger amount of the antigen than that carrying a plasmid with a single gene inserted therein.

The modified P31 proteins as well as P37 and P25 according to the present invention have essentially the same biological activity as that possessed by the known HBsAg small particles produced by using the blood of HBV-infected subjects as the starting material and can be used as vaccines for prevention of HBV infections and antigens for the diagnosis of HBV infections in the same manner as said HBsAg small particles.

In this specification and the accompanying drawings, those abbreviations that are recommended by the IUPAC-IUB Commission on Biochemical Nomenclature or are in common use in the relevant field of art are used for indicating bases and amino acids by abbreviations. Examples are given in the following. Unless otherwise specifically indicated, amino acids, for which optical isomerism is possible, are in the L form.

| | |
|---|---|
| DNA | Deoxyribonucleic acid |
| RNA | Ribonucleic acid |
| mRNA | Messenger RNA |
| A | Adenine |
| T | Thymine |
| G | Guanine |
| C | Cytosine |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| EDTA | Ethylenediaminetetraacetic acid |
| SDS | Sodium dodecyl sulfate |
| DTT | Dithiothreitol |
| Gly | Glycine |
| Ala | Alanine |
| Val | Valine |
| Leu | Leucine |
| Ile | Isoleucine |
| Ser | Serine |
| Thr | Threonine |
| Cys | Cysteine |
| ½Cys | Half cystine |
| Met | Methionine |
| Glu | Glutamic acid |
| Asp | Aspartic acid |
| Lys | Lysine |
| Arg | Arginine |
| His | Histidine |
| Phe | Phenylalanine |
| Tyr | Tyrosine |
| Trp | Tryptophan |
| Pro | Proline |
| Asn | Asparagine |
| Gln | Glutamine |
| $Ap^r$ | Ampicillin resistance gene |
| $Tc^r$ | Tetracycline resistance gene |
| ars 1 | Autonomous replication sequence 1 |
| IR | Inverted repeat |

BRIEF DESCRIPTION OF THE DRAWINGS

FIG. 2 shows the base sequence (upper row) of subtype adr HBsAg P31 and the corresponding amino acid sequence (lower row).

FIG. 3 shows the base sequence (upper) of the modified portion in pTRP P31-Ra and the corresponding amino acid sequence (lower). In this figure, the slashes indicate the missing portion and the symbol "Z N" indicates the added portion.

FIG. 4 shows the base sequence (upper) of the modified portion each of pTRP P31-Rb and pTRP P31-Rc and the corresponding amino acid sequence. In the figure, the slashes indicate the missing portions.

EXAMPLES

The following reference examples and working examples are further illustrative of the present invention. However, they are by no means limitative of the invention.

REFERENCE EXAMPLE 1

Construction of expression vector containing yeast repressible acid phosphatase promoter (PHO5-P)

The *Escherichia coli* plasmid pJA1 (50 μg) [Kramer, R. A. and Anderson, N., Proc. Natl. Acad. Sci. U.S.A., 77, 6541 (1980)] containing a 7.9 kb DNA fragment containing the *Saccharomyces cerevisiae* S288C-derived repressible acid phosphatase gene (PHO5) and constitutive acid phosphatase gene (PHO3) was treated with 20 units of the restriction enzyme BamHI (Takara Shuzo) and 20 units of the restriction enzyme SalI (Takara Shuzo) in a reaction mixture [10 mM Tris-HCl (pH 8.0), 7 mM MgCl$_2$, 100 mM NaCl, 2 mM 2-mercaptoethanol] at 37° C. for 3 hours, followed by 1.0% agarose (Sigma) slab gel electrophoresis in a buffer [100 mM Tris-HCl, 100 mM boric acid, 2 mM EDTA (pH 8.3)] at 140 volts for 2 hours. After electrophoresis, the gel piece containing a 0.63 kb DNA fragment was sealed in a dialysis tube, the tube was immersed in the buffer for electrophoresis, and said fragment was eluted electrically from the gel [McDonell, M. W. et al., J. Mol. Biol., 110, 119 (1977)]. The dialyzate within the dialysis tube was extracted with phenol and further with ether, NaCl was added to a concentration of 0.2M and, after addition of two volumes of cold ethanol, DNA precipitation was effected at −20° C.

Figure 10:
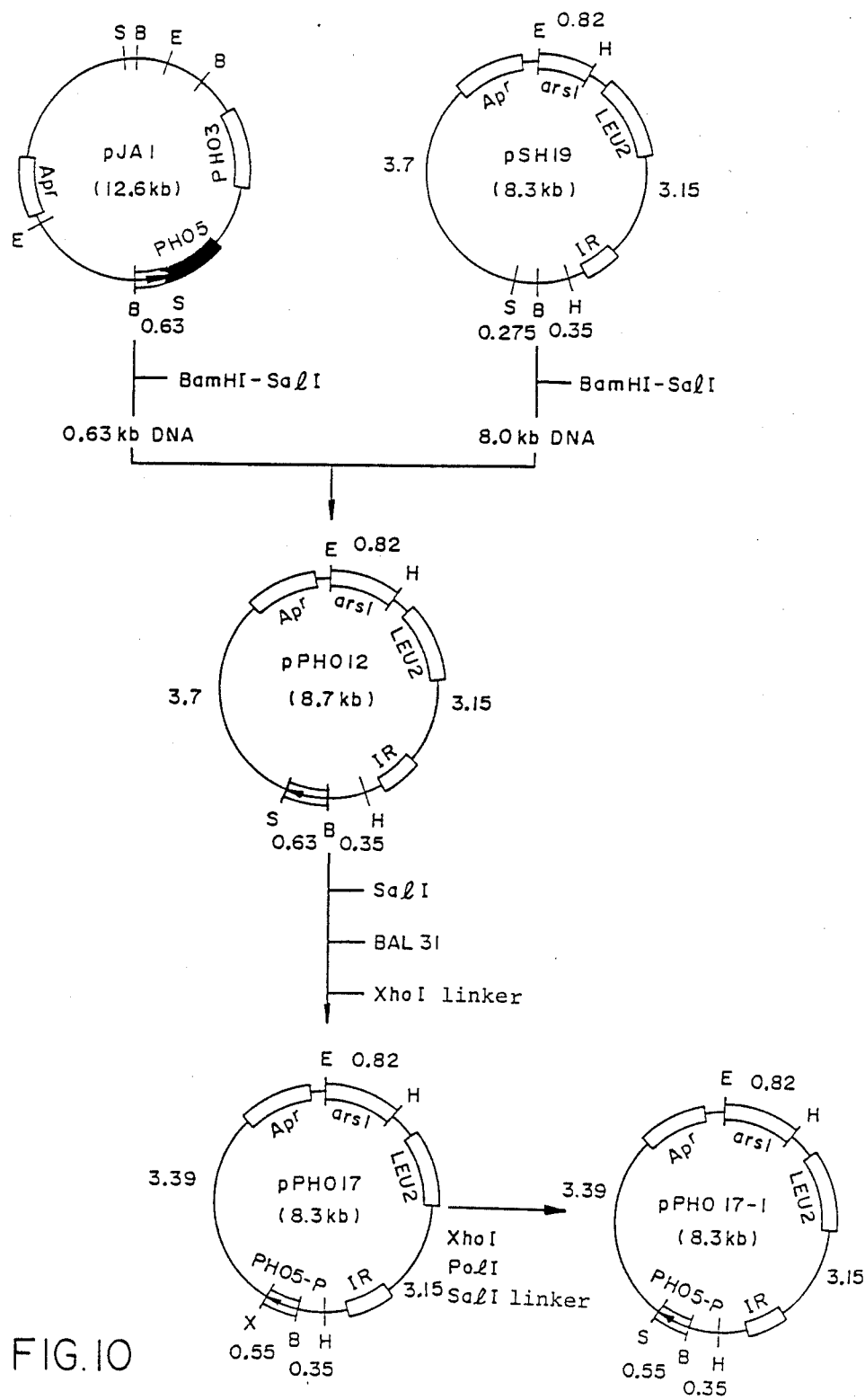
FIG. 10 shows the construction scheme for pPHO 17-1.

A 1-μg portion of the plasmid pSH 19 was digested with 2 units of the restriction enzyme BamHI and 2 units of the restriction enzyme SalI in 20 μl of a reaction mixture [10 mM Tris-HCl (pH 8.0), 7 mM MgCl$_2$, 100 mM NaCl, 2 mM 2-mercaptoethanol] at 37° C. for 2 hours, and the reaction mixture was subjected to electrophoresis using 0.8% agarose slab gel and operating under the above-mentioned conditions. After electrophoresis, an 8.0 kb DNA fragment was separated from the gel by the above-mentioned method, deproteinized with phenol and precipitated with cold ethanol (cf. FIG. 10).

A 400-ng portion of said 8.0 kb DNA fragment was mixed with 200 ng of the above-mentioned 0.63 kb DNA fragment, and DNA ligation was carried out overnight at 14° C. in 20 μl of a reaction mixture [66 mM Tris-HCl (pH 7.6), 6.6 mM MgCl$_2$, 10 mM dithiothreitol, 1 mM ATP, 2 units of T4 DNA ligase (Takara Shuzo)]. Using this mixture, the strain *Escherichia coli* 294 was transformed by the method of Cohen et al, supra. From along the transformants selected using ampicillin resistance as the index, a plasmid, pPHO 12, with the 0.63 kb DNA fragment from pJA1 being inserted at the BamHI-SalI site of pSH 19 was selected by examination of molecular weight and restriction enzyme cleavage pattern of plasmid DNA isolated by the above-mentioned alkaline extraction method (cf. FIG. 10).

A 3-μg portion of plasmid pPHO 12 DNA was digested with 2 units of the restriction enzyme SalI in 20 μl of a reaction mixture [10 mM Tris-HCl (pH 7.5), 7 mM MgCl$_2$, 175 mM NaCl, 0.2M EDTA, 7 mM 2-mercaptoethanol] at 37° C. for 2 hours, followed by deproteinization with phenol and DNA precipitation with cold ethanol. A 3 μg portion of this DNA was treated with 12 units of BAL31 nuclease (Bethesda Research Laboratories) in 50 μl of a reaction mixture [20 mM Tris-HCl (pH 8.1), 12 mM CaCl$_2$, 12 mM MgCl$_2$, 1 mM EDTA] at 30° C. for 2 minutes, followed by deproteinization with phenol and DNA precipitation with cold ethanol (cf. FIG. 10).

The XhoI linker d(CCTCGAGG) [200 ng; New England BioLabs] was phosphorylated at the 5' end by treating with 3 units of T4 polynucleotide kinase (Takara Shuzo) in 50 μl of a reaction mixture [50 mM Tris-HCl (pH 7.6), 10 mM MgCl$_2$, 10 mM 2-mercaptoethanol, 100 μM ATP] at 37° C. for 1 hour.

A 40 ng portion of the 5'-phosphorylated XhoI linker [5'-P-d(CCTCGAGG)] was mixed with 400 ng of the above-mentioned BAL-31-treated pPHO12 DNA and ligation was effected under the above-mentioned conditions in the presence of T4 DNA ligase. Using this reaction mixture, *Escherichia coli* 294 was transformed by the method of Cohen et al., supra. From among the plasmid DNAs isolated by the above-mentioned alkaline extraction method of the transformants selected with ampicillin resistance as the index, there was selected a plamid, pPHO 17, which gave 0.55 kb fragment upon double digestion with BamHI and XhoI. Analysis of the base sequence by the dideoxynucleotide method [Sanger, F. et al., Proc. Natl. Acad. Sci. U.S.A., 74, 5463 (1977)] revealed that the BAL-31 nuclease treatment had resulted in elimination of 20 bp upstream from the start codon ATG of PHO5 (cf. FIG. 10).

Then, 2 μg of said plasmid pPHO 17 was digested with 4 units of the restriction enzyme XhoI (Takara Shuzo) in 20 μl of a reaction mixture [6 mM Tris-HCl (pH 7.9), 150 mM NaCl, 6 mM MgCl$_2$, 6 mM 2-mercaptoethanol] at 37° C. for 2 hours, followed by deproteinization with phenol and DNA precipitation with cold ethanol.

A 1-μg portion of said DNA was treated with 5 units of DNA polymerase I large fragment (New England BioLabs) in 30 μl of a reaction mixture [40 mM potassium phosphate buffer (pH 7.5), 6.6 mM MgCl$_2$, 1 mM 2-mercaptoethanol, 33 μM dATP, 33 μM dGTP, 33 μM dTTP, 33 μM dCTP] at 12° C. for 30 minutes to render the cohesive ends blunt, followed by deproteinization with phenol and DNA precipitation with cold ethanol. 500 ng of said DNA fragment and 50 ng of the SalI linker phosphorylated under the above-mentioned conditions [5'-P-d(GGTCGACC)] (New England BioLabs) were mixed together and ligation was effected under the above-mentioned conditions under the action of T4 DNA ligase. Using this reaction mixture, *Escherichia coli* 294 was transformed by the method of Cohen et al., supra, and a plasmid pPHO 17-1, in which the XhoI site of the plasmid pPHO 17 was converted to an SalI site, was recovered from among ampicillin resistant transformants (cf. FIG. 10).

REFERENCE EXAMPLE 2

Construction of expression vector containing yeast phosphoglycerate kinase promoter (PGK-P)

(1) Cloning of phosphoglycerate kinase gene (PGK)

The chromosomal DNA (350 μg) of *Saccharomyces cerevisiae* strain Kyokai 3 (available from IFO) as prepared by the method of Cryer, D. R. et al. [Methods in Cell Biology, vol. XII, pp. 39–44 (1975)] was digested with 200 units of the restriction enzyme HindIII (Takara Shuzo) in 1 ml of a reaction mixture [10 mM Tris-HCl (pH 7.5), 7 mM $MgCl_2$, 60 mM NaCl] at 37° C. for 3 hours, followed by 1% agarose slab gel electrophoresis under the conditions described in Reference Example 1. After electrophoresis, the DNA fragments were fractionated into fractions 1–10 in the order of size by dividing the agarose gel. The agarose gel piece corresponding to each fraction was sealed in a dialysis tube and the DNA was electrically eluted from said gel piece under the conditions described in Reference Example 1. The eluate was treated with phenol and then cold ethanol was added to thereby cause DNA precipitation. A 0.5-μg portion of the DNA from each fraction was electrophoresed under the conditions described in Reference Example 1 using 1% agarose slab gel and then DNA adsorption on a nitrocellulose filter (Schleicher and Schull) was effected by the method of Southern [Southern, E. M., J. Mol. Biol., 98, 503 (1975)]. 5'-TGAAGATAAAGACAT-3', which is complementary to the oligonucleotide coding for the five amino acids from the N-terminus of PGK [Dobson, M. J. et al., Nucleic Acids Res., 10, 2625 (1982)], was synthesized by the method of Crea, R. et al. [Proc. Natl. Acad. Sci. U.S.A., 75, 5765 (1978)] and 1 μg of said oligonucleotide was reacted with 10 μCi of γ-[$^{32}$p]ATP (Amersham) in the presence of 10 units of polynucleotide kinase in 30 μl of a reaction mixture [50 mM Tris-HCl (pH 7.6), 10 mM $MgCl_2$, 10 mM 2-mercaptoethanol] at 37° C. for 30 minutes to thereby label the 5' end with $^{32}$P. To said reaction mixture was added 10 μl of 200 mM EDTA (pH 8.0) and, after deproteinization with phenol, the mixture was applied to a Sepharose 4B (Pharmacia) column (0.25×25 cm) equilibrated with TEN buffer [10 mM Tris-HCl (pH 8.0), 200 mM NaCl, 1 mM EDTA]. The labeled oligonucleotide eluted in the vicinity of the void volume was collected and used as a probe for screening the PGK gene. When blotting was performed using the above-mentioned nitrocellulose filter and said probe by the above-mentioned Southern method, the probe strongly hybridized with the sample of fraction No. 3 which contained 2.6–2.9 kb DNA fragments.

Then, 10 μg of the cloning vector pTR 262 [Roberts, T. M. et al., Gene, 12, 123 (1980)] was digested with 10 units of the restriction enzyme HindIII in 50 μl of a reaction mixture [10 mM Tris-HCl (pH 7.5), 7 mM $MgCl_2$, 60 mM NaCl] at 37° C. for 2 hours, followed by deproteinization with phenol and DNA precipitation with cold ethanol (HindIII-digested pTR 262). 0.1 μg of the HindIII-digested pTR262 and 0.2 μg of the DNA of fraction No. 3 were mixed together and ligation was effected using T4 DNA ligase under the conditions described in Reference Example 1. Using said reaction mixture, *Escherichia coli* DH1 [Maniatis, T. et al., Molecular Cloning, Cold Spring Harbor Laboratory, 254–255 (1982)] was transformed to give about 1300 transformants exhibiting tetracycline resistance.

From among them, PGK gene-carrying transformants were picked out by colony hybridization [Suggs, S. V. et al., Proc. Natl. Acad. Sci. U.S.A., 78, 6613 (1981)] using the above $^{32}$P-labeled synthetic probe. From a transformant giving a strong signal upon autoradiography, a plasmid, pPKT 3, was isolated by the above-mentioned alkaline extraction method and digested with HindIII, whereupon a 2.95 kb DNA insert was detected. Examination by the method of Southern, supra, confirmed that said insert was able to hybridize with said probe.

(2) Isolation of PGK promoter fragment

The plasmid pPKT 3 DNA (50 μg) was digested with 50 units of the restriction enzyme HindIII in 100 μl of a reaction mixture [10 mM Tris-HCl (pH 7.5), 7 mM $MgCl_2$, 60 mM NaCl] at 37° C. for 2 hours, followed by 1% agarose slab gel electrophoresis under the conditions described in Reference Example 1. After electrophoresis, a 2.95 kb DNA fragment was isolated from the gel by the method described in Reference Example 1 (cf. FIG. 11).

5 μg of said 2.95 kb DNA fragment was digested with 5 units of the restriction enzyme SalI in 20 μl of a reaction mixture [10 mM Tris-HCl (pH 7.5), 7 mM $MgCl_2$, 175 mM NaCl, 7 mM 2-mercaptoethanol] at 37° C. for 3 hours, followed by 1.2% agarose slab gel electrophoresis under the conditions described in Reference Example 1. After electrophoresis, a 2.1 kb DNA fragment was isolated from the gel by the method described in Reference Example 1. 0.5 μg of said 2.1 kb DNA fragment was mixed with 0.5 μg of a 3.74 kb DNA obtained by HindIII-SalI digestion of the plasmid pBR322 and ligation was effected using T4 DNA ligase under the conditions described in Reference Example 1. Using said reaction mixture, *Escherichia coli* DH1 was transformed and the desired plasmid, pPKT 101, was recovered from an ampicillin-resistant transformant (cf. FIG. 11).

Then, for eliminating the structural gene region from the PGK gene, 10 μg of said plasmid pPKT 101 was first digested with 10 units of the restriction enzyme SalI in 30 μl of a reaction mixture [10 mM Tris-HCl (pH 7.5), 7 mM $MgCl_2$, 175 mM NaCl, 0.2M EDTA, 7 mM 2-mercaptoethanol] at 37° C. for 3 hours, followed by deproteinization with phenol and DNA precipitation with cold ethanol (SalI-digested pPKT 101). Thereafter, 1 μg of the SalI-digested pPKT 101 was treated with 10 units of BAL31 nuclease in 20 μl of a reaction mixture [20 mM Tris-HCl (pH 8.1), 12 mM $CaCl_2$, 12 mM $MgCl_2$, 1 mM EDTA] at room temperature for 5 minutes, immediately followed by termination of the reaction by addition of 1 volume of phenol, which was further followed by DNA precipitation with cold ethanol (BAL-digested pPKT 101). 50 ng of the phosphorylated XhoI linker described in Reference Example 1 was mixed with 0.2 μg of the BAL-digested pPKT101 and ligation was effected under the conditions described in Reference Example 1 in the presence of T4 DNA ligase. *Escherichia coli* DH1 was transformed using said reaction mixture and, from among ampicillin-resistant transformants, a pPKT 101-derived plasmid, pPKT 567, missing a 0.69 kb portion starting from the SalI site of pPKT 101 and extending in the direction of the promoter region was recovered. Analysis of the DNA base sequence by the dideoxynucleotide method proved that, in pPKT 567, the BAL digestion had eliminated the PGK structural gene and a 5'-non-coding region up to −24 (cf. FIG. 11).

(3) Construction of expression vector

Figure 11:
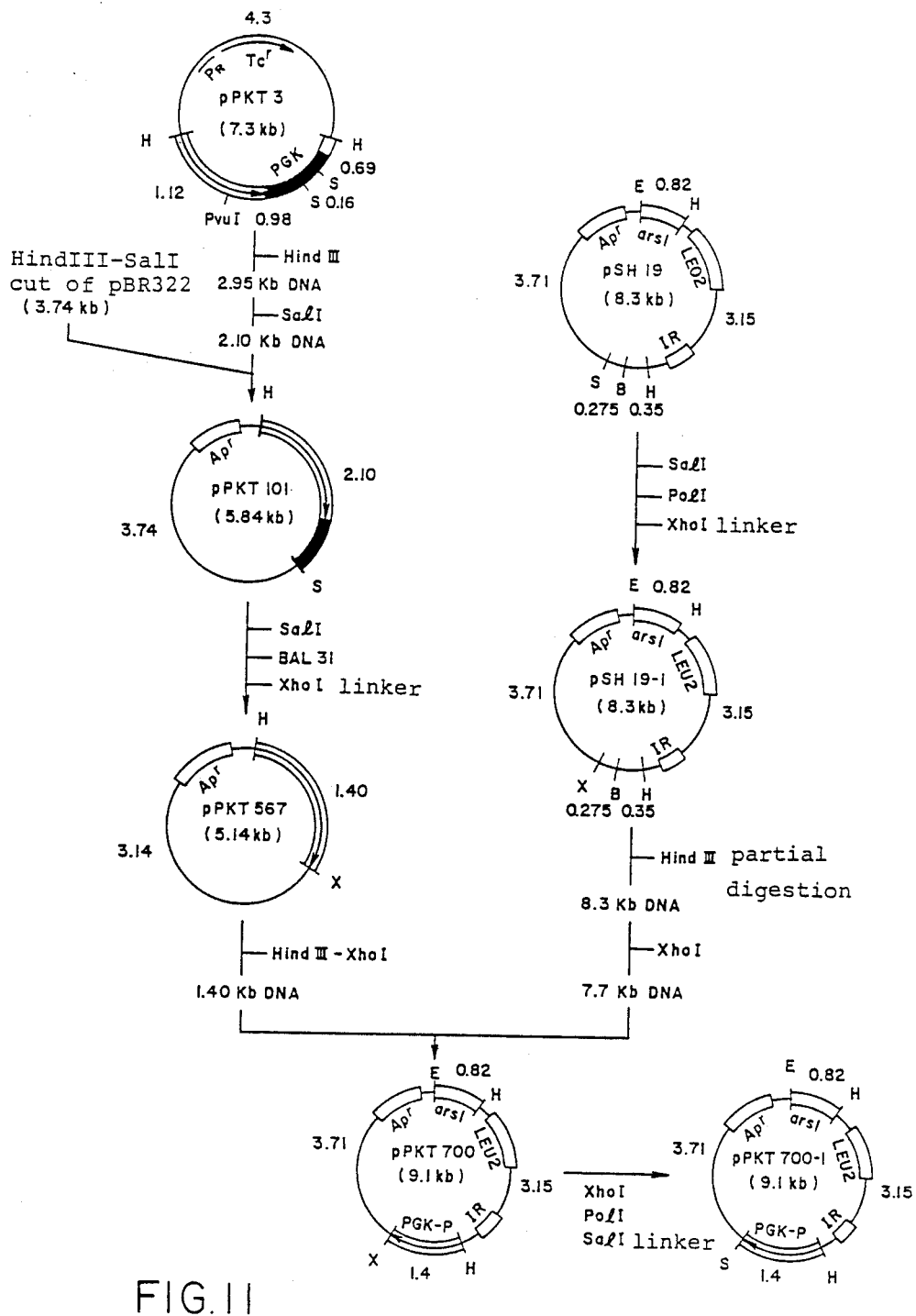
FIG. 11 shows the construction scheme for pPKT 700.1.

5 μg of the *Escherichia coli*-yeast shuttle vector pSH19 was digested with 6 units of the restriction enzyme SalI in 20 μl of a reaction mixture [10 mM Tris-HCl (pH 7.5), 7 mM MgCl$_2$, 175 mM NaCl, 0.2 mM EDTA, 7 mM 2-mercaptoethanol] at 37° C. for 2 hours, followed by deproteinization with phenol and DNA precipitation with cold ethanol. 1 μg of said DNA was treated with DNA polymerase I large fragment under the conditions described in Reference Example 1 to thereby render the SalI cohesive ends blunt. 500 ng of said DNA fragment was mixed with 50 ng of the phosphorylated XhoI linker described in Reference Example 1 and ligation was effected under the conditions described in Reference Example 1. *Escherichia coli* DH1 was transformed with said reaction mixture and, from among ampicillin-resistant transformants, there was obtained a transformant carrying a plasmid, pSH 19-1, resulting from conversion of the SalI site of pSH 19 to an XhoI site (cf. FIG. 11).

15 μg of said plasmid pSH 19-1 DNA was digested with 24 units of the restriction enzyme HindIII in 100 μl of a reaction mixture [10 mM Tris-HCl (pH 7.5), 7 mM MgCl$_2$, 60 mM NaCl] at 37° C. for 10 minutes, followed immediately by termination of the reaction by addition of 10 μl of 0.2M EDTA. The reaction mixture was subjected to 0.7% agarose slab gel electrophoresis under the conditions described in Reference Example 1 and an 8.3 kb DNA fragment resulting from cleavage at one HindIII site of the plasmid was recovered from the gel by the method described in Reference Example 1. 3 μg of said 8.3 kb DNA fragment was digested with 10 units of the restriction enzyme XhoI (Takara Shuzo) in 30 μl of a reaction mixture [10 mM Tris-HCl (pH 7.5), 7 mM MgCl$_2$, 100 mM NaCl, 7 mM 2-mercaptoethanol] at 37° C. for 2 hours, followed by 0.7% agarose slab gel electrophoresis under the conditions described in Reference Example 1. After electrophoresis, a 7.7 kb DNA fragment was separated from the gel by the method described in Reference Example 1 (cf. FIG. 11).

10 μg of the plasmid pPKT 567 DNA described in (2) of Reference Example 2 was digested with 10 units each of the restriction enzymes HindIII and XhoI in 50 μl of a reaction mixture [50 mM Tris-HCl (pH 7.6), 50 mM NaCl, 1 mM dithiothreitol, 10 mM MgCl$_2$] at 37° C. for 2 hours. Following 1.2% agarose slab gel electrophoresis performed under the conditions described in Reference Example 1, a 1.40 kb DNA fragment was isolated from the gel (cf. FIG. 11).

0.2 μg of said 1.40 kb DNA fragment was mixed with 0.5 μg of the above-mentioned 7.7 kb DNA fragment and ligation was effected using T4 DNA ligase under the conditions described in Reference Example 1. *Escherichia coli* DH1 was transformed with said reaction mixture and a transformant bearing the desired plasmid, pPKT 700 was picked out from among ampicillin-resistant transformants. Then, following the procedure described in Reference Example 1, a plasmid, pPKT 700-1, having a SalI site in place of the XhoI site of the plasmid pPKT 700 was constructed (cf. FIG. 11).

REFERENCE EXAMPLE 3

Construction of expression vector containing yeast glyceraldehyde 3-phosphate dehydrogenase promoter (GLD-P)

(1) Cloning of glyceraldehyde 3-phosphate dehydrogenase gene (GLD)

5'-AGCAACTCTAACCAT-3', complementary to the oligonucleotide portion of GLD coding for the five amino acdis from the N terminus of pgap491 [Holland, J. P. et al., J. Biol. Chem., 258, 5291 (1983)], was synthesized by the above-mentioned method of Crea, R. et al. and labeled with $^{32}$P according to the procedure described in (1) of Reference Example 2, for use as a probe. Upon Southern blotting using the nitrocellulose filter described in (1) of Reference Example 2 and said probe, the probe strongly hybridized with the sample of fraction No. 7 containing 2.0–2.3 kb DNA fragments.

Figure 12:
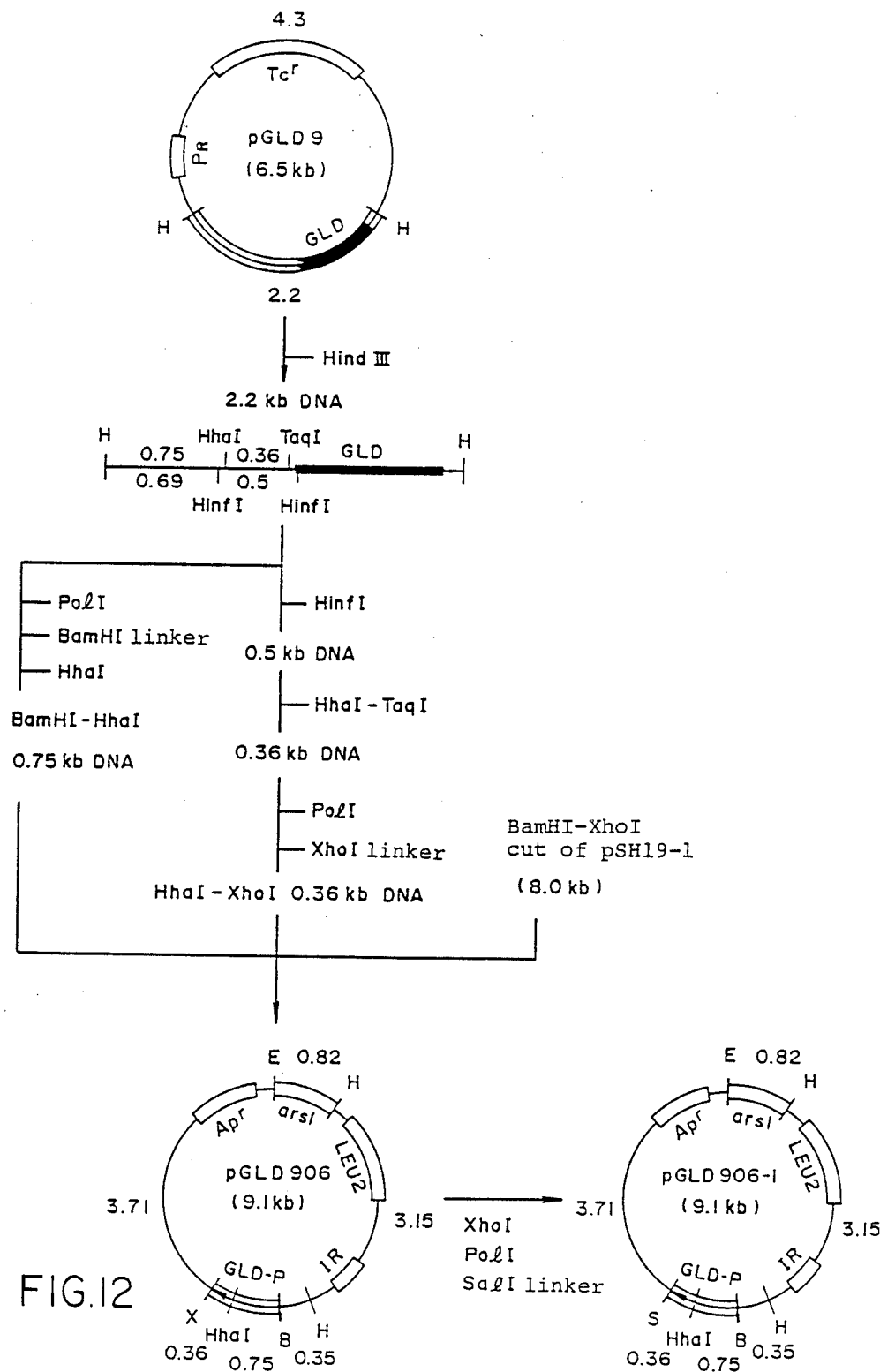
FIG. 12 shows the construction scheme for pGLD 906-1.

0.1 μg of the HindIII-digested pTR 262 described in (1) of Reference Example 2 was mixed with 0.2 μg of the DNA of fraction No. 7 and ligation was carried out using T4 DNA ligase under the conditions described in Reference Example 1. The reaction mixture was used for transformation of *Escherichia coli* DH1, which was performed by the method described in (1) of Reference Example 2 and gave about 1,200 tetracycline-resistant transformants. From among these transformants, one capable of strongly hybridizing with the $^{32}$P-labeled probe in colony hybridization was picked out. A plasmid, pGLD 9, was isolated from this transformant by the above-mentioned alkaline extraction method. Upon digestion with HindIII, a 2.2 kb insert DNA was detected, while testing by the method of Southern confirmed that this insert could hybridize with said probe (cf. FIG. 12).

(2) Isolation of GLD promoter fragment

100 μg of the plasmid pGLD 9 DNA was digested with 50 units of the restriction enzyme HindIII in 200 μl of a reaction mixture [10 mM Tris-HCl (pH 7.5), 7 mM MgCl$_2$, 60 mM NaCl] at 37° C. for 3 hours, followed by 1.0% agarose slab gel electrophoresis under the conditions described in Reference Example 1. After electrophoresis, a 2.2 kb DNA fragment was separated from the gel by the method described in Reference Example 1. 10 μg of said 2.2 kb DNA fragment was digested with 10 units of the restriction enzyme HinfI (Takara Shuzo) in 50 μl of a reaction mixture [10 mM Tris-HCl (pH 7.5), 7 mM MgCl$_2$, 100 mM NaCl, 7 mM 2-mercaptoethanol] at 37° C. for 2 hours, followed by hybridization using the probe for GLD and the method of Southern, whereupon said probe was bound to a 0.5 kb DNA fragment (cf. FIG. 12).

5 μg of said 0.5 kb DNA fragment was digested with 10 units each of the restriction enzymes HhaI (Takara Shuzo) and TaqI (New England BioLabs) in 30 μl of a reaction mixture [10 mM Tris-HCl (pH 7.5), 50 mM NaCl, 10 mM MgCl$_2$, 1 mM dithiothreitol] at 37° C. for 3 hours, followed by 1.5% agarose slab gel electrophoresis under the conditions described in Reference Example 1. After electrophoresis, a 0.36 kb DNA fragment was separated from the gel by the method described in Reference Example 1 (cf. FIG. 12).

1 μg of said 0.36 kb DNA fragment was treated with DNA polymerase I large fragment under the conditions described in Reference Example 1 to thereby render the cohesive TaqI ends blunt. Then, 1 μg of this fragment was mixed with 50 ng of the phosphorylated XhoI linker described in Reference Example 1 and ligation was conducted using T4 DNA ligase under the conditions described in Reference Example 1. Thereafter, an excessive amount of XhoI was added and, after 4 hours of digestion at 37° C., the 0.36 kb DNA fragment with the linker joined thereto was isolated using a Sepharose 4B column under the conditions described in (1) of Reference Example 2.

Separately, 10 μg of the above-mentioned 2.2 kb DNA was treated with DNA polymerase I large fragment under the conditions described in Reference Example 1 to thereby render the cohesive ends blunt and then ligated with 50 ng of a BamHI linker (New England BioLabs) phosphorylated under the conditions described in Reference Example 1 [5'-Pd(CGCGGATCCGCG)] using T4 DNA ligase under the conditions described in Reference Example 1. Thereafter, 20 units of BamHI was added and digestion was carried out at 37° C. for 3 hours and, then, the 2.2 kb DNA fragment with the linker joined thereto was isolated using a Sepharose 4B column under the conditions described in (1) of Reference Example 2. 6 μg of said DNA fragment was digested with 2 units of the restriction enzyme HhaI in 50 μl of a reaction mixture [10 mM Tris-HCl (pH 7.5), 50 mM NaCl, 10 mM MgCl₂, 1 mM dithiothreitol] at 37° C. for 2 hours, followed by 1.0% agarose slab gel electrophoresis under the conditions described in Reference Example 1. After electrophoresis, a 0.75 kb DNA fragment was separated from the gel by the method described in Reference Example 1 (cf. FIG. 12).

(3) Construction of expression vector

10 μg of the plasmid pSH19-1 DNA described in (3) of Reference Example 2 was digested with 10 units each of the restriction enzymes BamHI and XhoI in 50 μl of a reaction mixture [10 mM Tris-HCl (pH 7.5), 7 mM MgCl₂, 100 mM NaCl, 7 mM 2-mercaptoethanol] at 37° C. for 2 hours, followed by 1.0% agarose slab gel electrophoresis under the conditions described in Reference Example 1. After electrophoresis, an 8.0 kb DNA fragment was separated from the gel by the method described in Reference Example 1.

500 ng of said 8.0 kb DNA fragment was mixed with 200 ng of the 0.36 kb DNA fragment and 200 ng of the 0.75 kb DNA fragment each described in (2) of Reference Example 3 and ligation was effected using T4 DNA ligase under the conditions described in Reference Example 1. *Escherichia coli* DH1 was transformed using the reaction mixture and a transformant carrying a plasmid, pGLD 906, consisting of the three DNA fragments joined together was isolated from among ampicillin-resistant transformants. Then, a plasmid, pGLD 906-1, was derived from said plasmid pGLD906 by converting the XhoI site to a SalI site by following the procedure described in Reference Example 1 (cf. FIG. 12).

REFERENCE EXAMPLE 4

Figure 13:
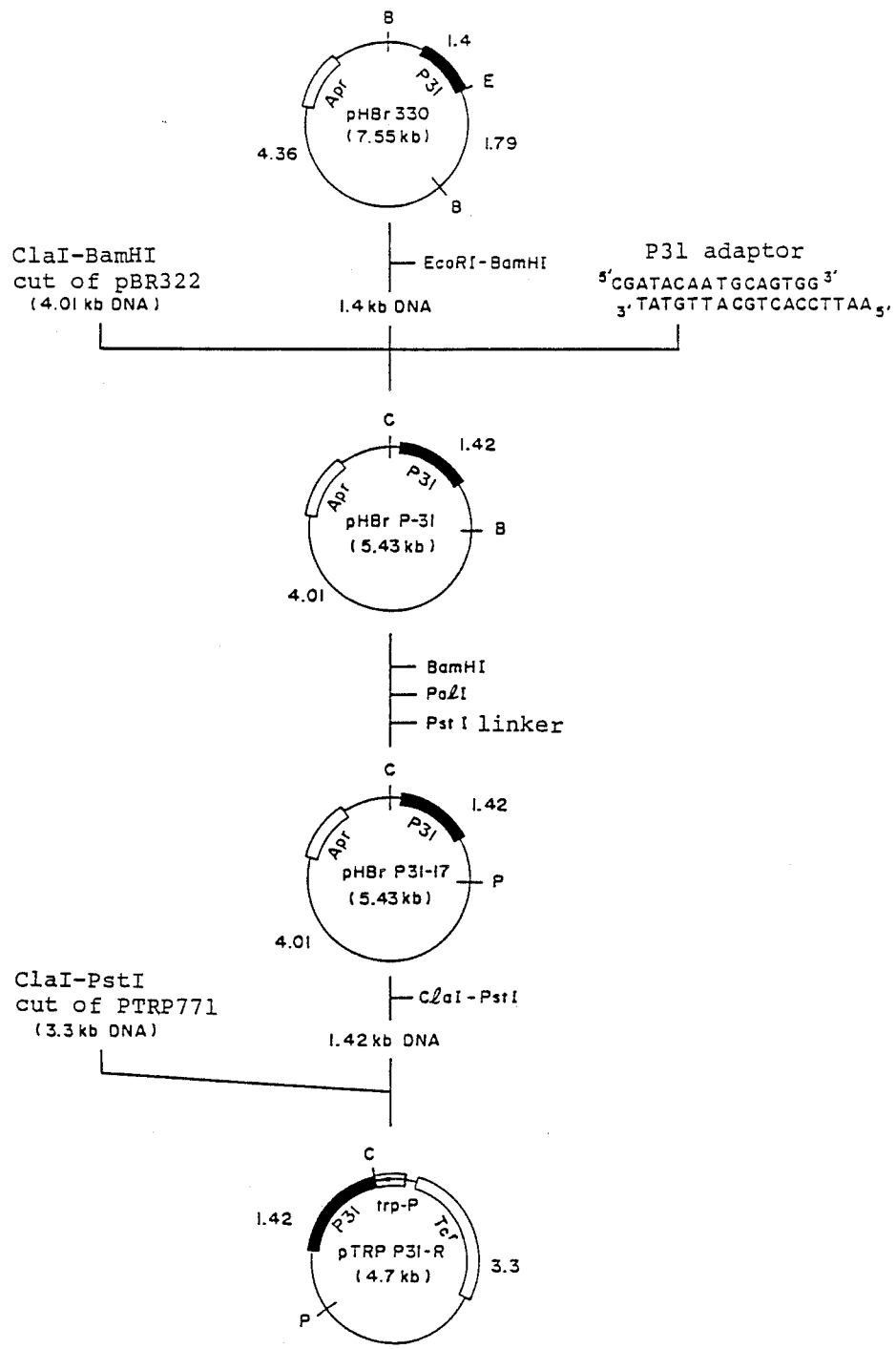
FIG. 13 shows the construction scheme for pTRP P31-R.

Construction of recombinant DNA capable of expression of subtype adr hepatitis B virus surface antigen P31 gene and transformation of *Escherichia coli* with said DNA The plasmid pBR322-BamHI/HBr330 DNA (also referred to as "pHBr330") described in Japanese Patent Unexamined Publication No. 74985/1984 and Nucleic Acids Res., 11, 1747 (1983) was prepared following the procedure described in Reference Example 1 of Japanese Patent Unexamined Publication No. 201796/1983. 50 μg of said plasmid pHBr330 was digested with 20 units each of the restriction enzymes EcoRI (Takara Shuzo) and BamHI in 100 μl of a reaction mixture [100 mM Tris-HCl (pH 7.5), 7 mM MgCl₂, 50 mM NaCl, 7 mM 2-mercaptoethanol] at 37° C. for 3 hours, followed by 1.0% agarose slab gel electrophoresis under the conditions described in Reference Example 1. After electrophoresis, a 1.4 kb DNA fragment was separated from the gel by the method described in Reference Example 1 (cf. FIG. 13).

2 μg of the plasmid pBR322 DNA was digested with 2 units each of the restriction enzymes BamHI and ClaI (New England BioLabs) in 20 μl of a reaction mixture [10 mM Tris-HCl (pH 8.0), 7 mM MgCl₂, 100 mM NaCl, 2 mM 2-mercaptoethanol] at 37° C. for 2 hours, followed by 0.8% agarose slab gel electrophoresis under the conditions described in Reference Example 1. Thereafter, a 4.01 kb DNA fragment was separated from the gel by the method described in Reference Example 1.

500 ng of the above 4.01 kb DNA fragment, 500 ng of the above 1.4 kb DNA fragment and 50 ng of a synthetic adaptor

phosphorylated at the 5' ends by the method described in Reference Example 1 were ligated together using T4 DNA ligase under the conditions described in Reference Example 1. The above adaptor was chemically synthesized by the phosphotriester method [Crea, R. et al., Proc. Natl. Acad. Sci. U.S.A., 75, 5765 (1978)]. Using the reaction mixture, *Escherichia coli* 294 was transformed and a plasmid (pHBr P31) DNA consisting of the above three DNAs joined together was isolated from an ampicillin-resistant transformant (cf. FIG. 13).

1 μg of the plasmid pHBr P31 DNA was digested with 2 units of the restriction enzyme BamHI in 20 μl of a reaction mixture [10 mM Tris-HCl (pH 8.0), 7 mM MgCl₂, 100 mM NaCl, 2 mM 2-mercaptoethanol] at 37° C. for 2 hours, followed by deproteinization with phenol and DNA precipitation by addition of cold ethanol (BamHI-digested pHBr P31).

500 ng of the BamHI-digested pHBr P31 was filled in with DNA polymerase I large fragment under the conditions described in Reference Example 1 to render the cohesive ends blunt, followed by deproteinization with phenol and DNA precipitation with cold ethanol. 300 ng of said DNA fragment and 50 ng of a PstI linker [5'-Pd(GCTGCAGC)] (New England BioLabs) phosphorylated at the 5' end by the method described in Reference Example 1 were ligated together under the conditions described in Reference Example 1 in the presence of T4 DNA ligase. Using the reaction mixture, *Escherichia coli* 294 was transformed, transformants were checked by the method described in Reference Example 1, and a plasmid, pHBrP31-17, in which the BamHI site of the plasmid pHBrP31 had been converted to a PstI site, was isolated (cf. FIG. 13).

50 μg of said pHBr P31-17 was digested with 20 units each of the restriction enzymes ClaI and PstI (Takara Shuzo) in 100 μl of a reaction mixture [20 mM Tris-HCl (pH 7.5), 10 mM MgCl₂, 50 mM (NH₄)₂SO₄] at 37° C. for 3 hours, followed by 1.0% agarose slab gel electrophoresis under the conditions described in Reference Example 1. After electrophoresis, a 1.42 kb DNA fragment was separated from the gel by the method described in Reference

EXAMPLE 1

50 μg of the expression vector pTRP 771 described in Japanese Patent Unexamined Publication No. 201796/1983 and Nucleic Acids Res., 11, 3581 (1983) was digested with the restriction enzymes ClaI and PstI in 100 μl of the above-mentioned reaction mixture under the same conditions. The reaction mixture was subjected to 1.0% agarose slab gel electrophoresis under the conditions described in Reference Example 1. After electrophoresis, a 3.3 kb DNA fragment was separated from the gel by the method described in Reference Example 1.

200 ng of said 1.42 kb DNA (P31-encoding DNA) and 500 ng of the 3.3 kb DNA were ligated together under the conditions described in Reference Example 1 in the presence of T4 DNA ligase. The reaction mixture was used for transformation of Escherichia coli 294 and a transformant Escherichia coli strain (294/pTRP P31-R) carrying a plasmid (pTRP P31-R) comprising the expression vector and said P31-encoding DNA inserted into said vector was isolated by the method of Reference Example 1 (cf. FIG. 13).

Furthermore, Escherichia coli C600 was transformed with the plasmid pTRP P31-R to give Escherichia coli C600/pTRP P31-R.

REFERENCE EXAMPLE 5

Construction of DNA molecule for use in yeast, which is capable of expression of subtype adr hepatitis B virus surface antigen P31 gene and transformation of yeast with said DNA molecule (1) 50 μg of the plasmid pHBr P31 DNA described in Reference Example 4 was digested with 20 units each of the restriction enzymes ClaI and BamHI in 100 μl of a reaction mixture [100 mM Tris-HCl (pH 8.0), 7 mM $MgCl_2$, 100 mM NaCl, 2 mM 2-mercaptoethanol] at 37° C. for 3 hours, followed by 1.0% agarose slab gel electrophoresis under the conditions described in Reference Example 1. Thereafter, a 1.42 kb DNA fragment was separated from the gel by the method described in Reference Example 1.

Figure 14:
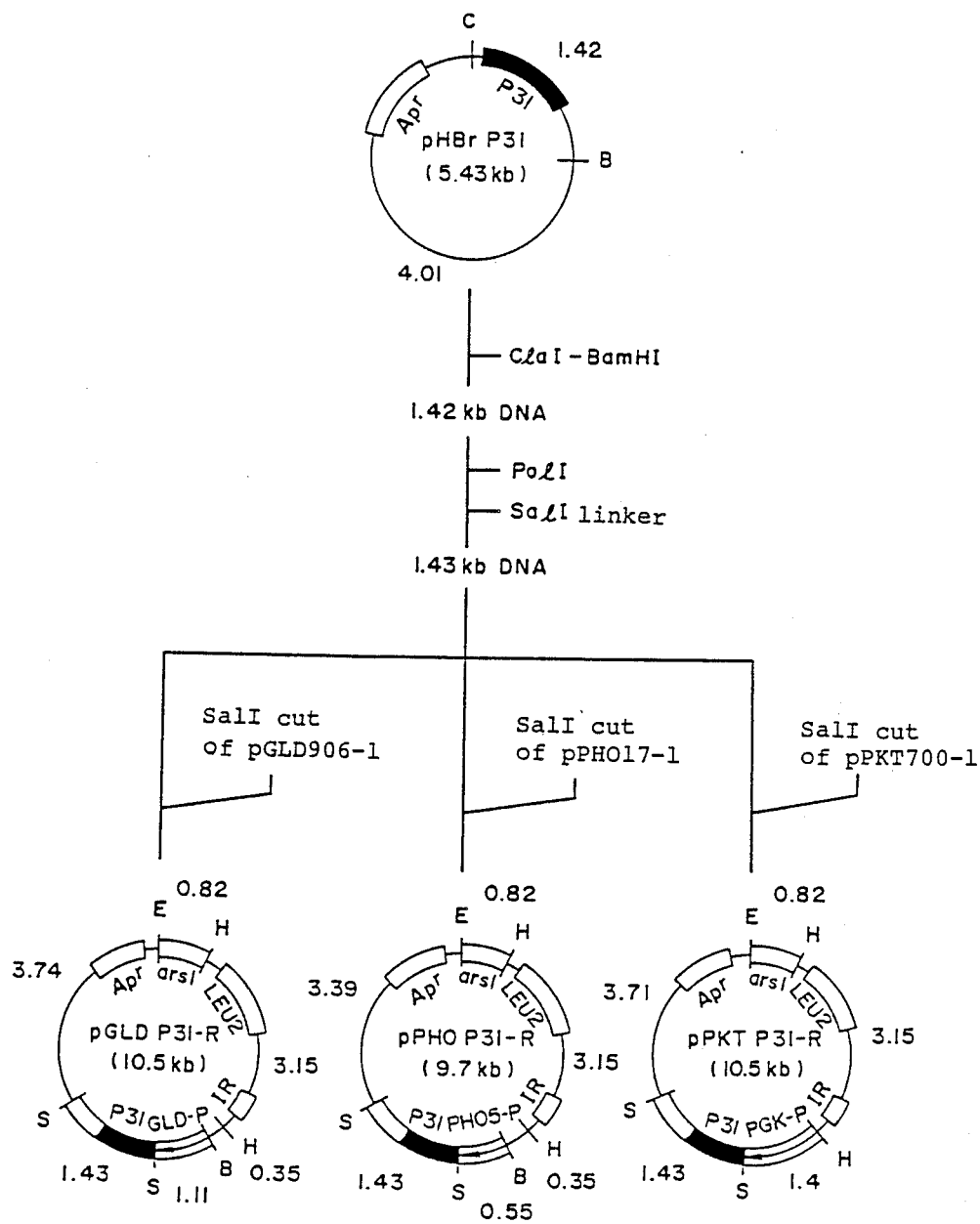
FIG. 14 shows the construction scheme for pPHO P31-R.

2 μg of said 1.42 kb DNA fragment was filled in under the conditions described in Reference Example 1 in the presence of DNA polymerase I large fragment to thereby make the cohesive ends blunt, followed by deproteinization with phenol and DNA precipitation with cold ethanol. 1.5 μg of said DNA and 50 ng of the phosphorylated SalI linker described in Reference Example 1 were ligated under the conditions described in Reference Example 1 in the presence of T4 DNA ligase. To the reaction mixture was added the restriction enzyme SalI, and digestion was performed at 37° C. for 3 hours, which led to cohesive end formation. After deproteinization with phenol, the reaction mixture was applied to a Sepharose 4B column and a 1.43 kb DNA fragment-containing fraction eluted in the vicinity of the void volume under the conditions described in (1) of Reference Example 2 was collected. Said DNA, i.e. a DNA coding for subtype adr P31, was precipitated with cold ethanol (cf. FIG. 14).

1 μg of the expression vector pPHO 17-1 described in Reference Example 1 was digested with 2 units of the restriction enzyme SalI in 20 μl of a reaction mixture [6 mM Tris-HCl (pH 7.5), 6 mM $MgCl_2$, 150 mM NaCl, 6 mM 2-mercaptoethanol] at 37° C. for 2 hours, followed by addition of 0.1 unit of alkaline phosphatase and further digestion at 65° C. for 30 minutes. Thereafter, deproteinization was carried out with phenol and DNA precipitation by addition of cold ethanol (SalI-digested pPHO 17-1).

Then, 200 ng of the above-mentioned 1.43 kb DNA fragment and 200 ng of the SalI-digested pPHO 17-1 were ligated together under the conditions described in Reference Example 1 in the presence of T4 DNA ligase. Using the reaction mixture, Escherichia coli 294 was transformed and transformants were examined by the method described in Reference Example 1. A tramsformant (Escherichia coli 294/pPHO P31-R) carrying a plasmid, pPHO P31-R, with the subtype 1.43 kb DNA fragment containing the subtype adr P31-encoding DNA being inserted in the same directionality as that of the PHO-5 promoter was thus isolated. Said plasmid pPHO P31-R was separated from this transformant by the alkaline extraction method and used for transformation of the host yeast Saccharomyces cerevisiae AH22R$^-$ by the above-mentioned method of Hinnen et al., and a yeast transformant (AH22R$^-$/pPHO P31-R) carrying said plasmid was isolated (cf. FIG. 14).

REFERENCE EXAMPLE 6

Figure 19:
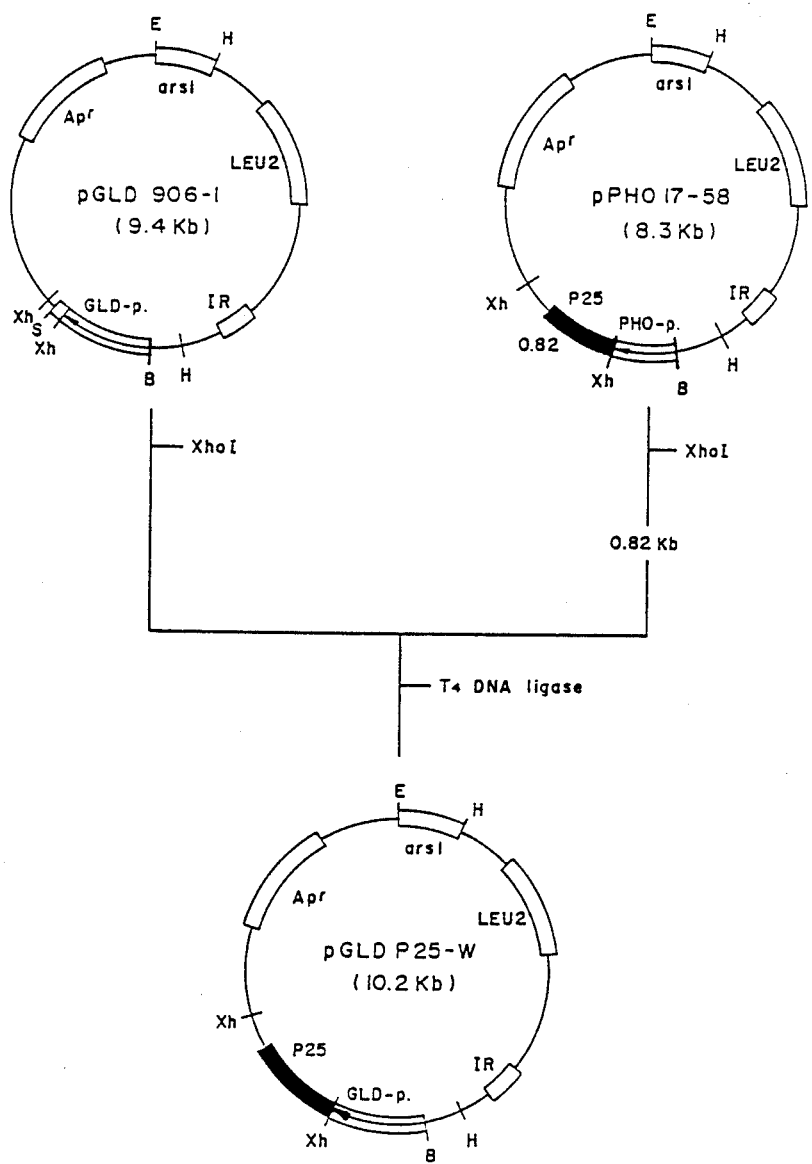
FIG. 19 shows the construction scheme for pGLD P25-W.

Construction of P25 gene expression plasmid using exogenous gene expression vector having GLD promoter 5 μg of the plasmid pPHO 17-58 described in the Example of Japanese Patent Application No. 193765/1984 filed on Sept. 13, 1984 [Japanese Unexamined Patent Publication No. 70989/1986] was digested with the restriction enzyme XhoI and a 0.82 kb DNA fragment containing subtype adw P25 gene was separated by the agarose slab gel electrophoresis method described in Reference Example 1. 0.5 μg of said DNA was mixed with 0.1 μg of a DNA obtained by digestion of the exogenous gene expression plasmid pGLD 906-1 described in Reference Example 3 with XhoI and ligation was effected using T4 DNA ligase. The reaction mixture was used for transformation of Escherichia coli DH1 to give ampicillin-resistant transformants. From one of the transformants, there was obtained a plasmid, pGLD P25-W, with the P25 gene inserted therein in the same directionality of that of the GLD promoter (FIG. 19).

EXAMPLE 1

Construction of modified subtype adr P31 gene in which codon for 48th amino acid arginine of P31 is missing 1.0 μg of the plasmid pTRP P31-R was digested with 2 units of the restriction enzyme XhoI (Nippon Gene) in 15 μl of a reaction mixture [50 mM Tris-HCl (pH 7.5), 100 mM NaCl, 10 mM $MgCl_2$, 1 mM dithiothreitol] at 37° C. for 2 hours, followed by deproteinization with phenol and DNA precipitation by addition of cold ethanol. The DNA was treated with 2.5 units of S1 nuclease (Bethesda Research Laboratories) in 20 μl of a reaction mixture [30 mM sodium acetate buffer (pH 4.6), 50 mM NaCl, 1 mM $ZnSO_4$, 5% glycerol] at room temperature for 30 seconds, immediately followed by deproteinization with phenol and DNA precipitation by addition of cold ethanol. The DNA was mixed with 50 ng of a 5' end-phosphorylated BamHI linker [5'-P-d(CCGGATCCGG)] (Bethesda Research Laboratories) and ligation was carried out in 20 μl of a reaction mixture [66 mM Tris-HCl (pH 7.6), 6.6 mM MgCl$_2$, 10 mM dithiothreitol, 1 mM ATP, 2 units of DNA ligase (New England BioLabs)] at 14° C. overnight. To the reaction mixture was added 10 units of BamHI (Nippon Gene). After 2 hours of digestion at 37° C., the reaction mixture was subjected to 0.8% agarose slab gel electrophoresis in a buffer [100 mM Tris-HCl, 100 mM boric acid, 2 mM EDTA (pH 8.3)] at 140 V for 2 hours. After electrophoresis, the gel pieces containing 3.1 kb and 1.6 kb DNA fragments with the BamHI linker added thereto were respectively sealed in dialysis tubes. The tubes were immersed in a buffer for electrophoresis and the DNA fragments were eluted electrically [McDonell, M. W. et al., J. Biol. Chem., 110, 119 (1977)]. The dialysis tube contents were extracted with phenol and further with ether. Then, NaCl was added to a concentration of 0.2M, followed by addition of 2 volumes of cold ethanol to cause precipitation of said DNA fragments. Said DNA fragments were converted to a circular DNA by treatment with T4 DNA ligase under the above-mentioned conditions. To the reaction mixture was added 5 units of the restriction enzyme XhoI and, after 2 hours of treatment at 37° C., the reaction mixture was used for transforming *Escherichia coli* DH1 [Maniatis, T. et al., Molecular Cloning, Cold Spring Harbor Laboratory, 254–255 (1982)] to give tetracycline-resistant transformants. From one of said transformants, there was obtained a plasmid, pTRP P31-Ra, having a BamHI site in place of the XhoI site of the subtype adr P31 gene and missing the codon for the 48th amino acid arginine. The sequence of the mutation site of said plasmid is shown in FIG. 3.

1.0 μg of the plasmid pTRP P31-R digested with the restriction enzyme XhoI was treated with 5 units of the exonuclease Bal31 (Bethesda Research Laboratories) in 20 μl of a reaction mixture [20 mM Tris-HCl (pH 8.1), 12 mM CaCl$_2$, 12 mM MgC$_2$, 1 mM EDTA] at room temperature for 3 seconds, immediately followed by deproteinization with phenol and DNA precipitation by addition of cold ethanol. The DNA was converted to a circular DNA by treatment with T4 DNA ligase under the conditions mentioned above, which was followed by digestion with the restriction enzyme XhoI. This reaction mixture was used for transformation of *Escherichia coli* DH1. From among the tetracycline-resistant transformants thus obtained, clones reactive with an anti-HBsAg antibody were selected by colony immunoassay [David, J. K. et al., Methods in Enzymology, 79, 622–630 (1981)] so that plasmids retaining the right reading frame of the P31 gene could be picked out. As a result, pTRP P31-Rb and pTRP P31-Rc were obtained as such clones. The plasmids were analyzed for the sequence of the mutation site by the M13 dideoxy method [Yoshioka, K. et al., Saibo Kogaku (Cell Engineering), 1, 79–87 (1982)]. The results of the analysis are shown in FIG. 4.

EXAMPLE 2

Expression of modified P31 gene in *Escherichia coli*

The plasmids pTRP P31-Ra, pTRP P31-Rb and pTRP P31-Rc described in Example 1 were used for transformation of the *Escherichia coli* strains 294 and C600 to give the following transformants: 294/pTRP P31-Ra, 294/pTRP P31Rb, 294/pTRP P31-Rc, C600/pTRP P31-Ra, C600/pTRP P31-Rb and C600/pTRP P31-Rc.

Each transformant was cultivated in M-9 medium containing 2.0% glucose and 1.0% Casamino Acids at 37° C. for 8 hours and, then, cells were harvested and washed with a buffer [30 mM Tris-HCl (pH 8.0), 50 mM NaCl, 5 mM EDTA]. The cells were suspended and lysed in a lysing solution containing 10 mM Tris-HCl (pH 8.0), 5 mM EDTA, 1 mM phenylmethylsulfonyl fluoride and 5 mg/ml lysozyme. Guanidine hydrochloride was added to the lysate solution to a final concentration of 7M, followed by incubation at 37° C. for 2 hours. The lysate solution was centrifuged at 15,000 rpm at room temperature for 15 minutes. A defined amount of the supernatant obtained was spotted onto a piece of cyanogen bromide-activated filter paper. This filter paper piece was immersed in a 5% glycine solution [5% glycine, 50 mM Tris-HCl (pH 8.0), 0.5M NaCl, 0.1% Triton X-100] for 16 hours and then washed thoroughly with a washing solution [50 mM Tris-HCl (pH 8.0), 0.5M NaCl, 0.1% Triton X-100, 0.2% bovine serum albumin]. Said filter paper piece was subjected to reaction with the $^{125}$I-anti-HBsAg monoclonal antibody (10$^6$ cpm/ml) for 3 hours, followed by washing with the washing solution. After air drying, the radioactivity of this filter paper piece was measured using a gamma ray counter and the antigen quantity was calculated. The results thus obtained are shown in Table 1, wherein the yield is per liter of the broth. A purified standard HBsAg P31 sample was used as the standard for the assay.

TABLE 1

| Transformant | HBsAg (mg/λ broth) |
| --- | --- |
| *Escherichia coli* 294/pTRP P31-Ra | 1.5 |
| *Escherichia coli* 294/pTRP P31-Rb | 1.8 |
| *Escherichia coli* 294/pTRP P31-Rc | 2.0 |
| *Escherichia coli* C600/pTRP P31-Ra | 2.3 |
| *Escherichia coli* C600/pTRP P31-Rb | 2.6 |
| *Escherichia coli* C600/pTRP P31-Rc | 2.4 |

EXAMPLE 3

Figure 5:
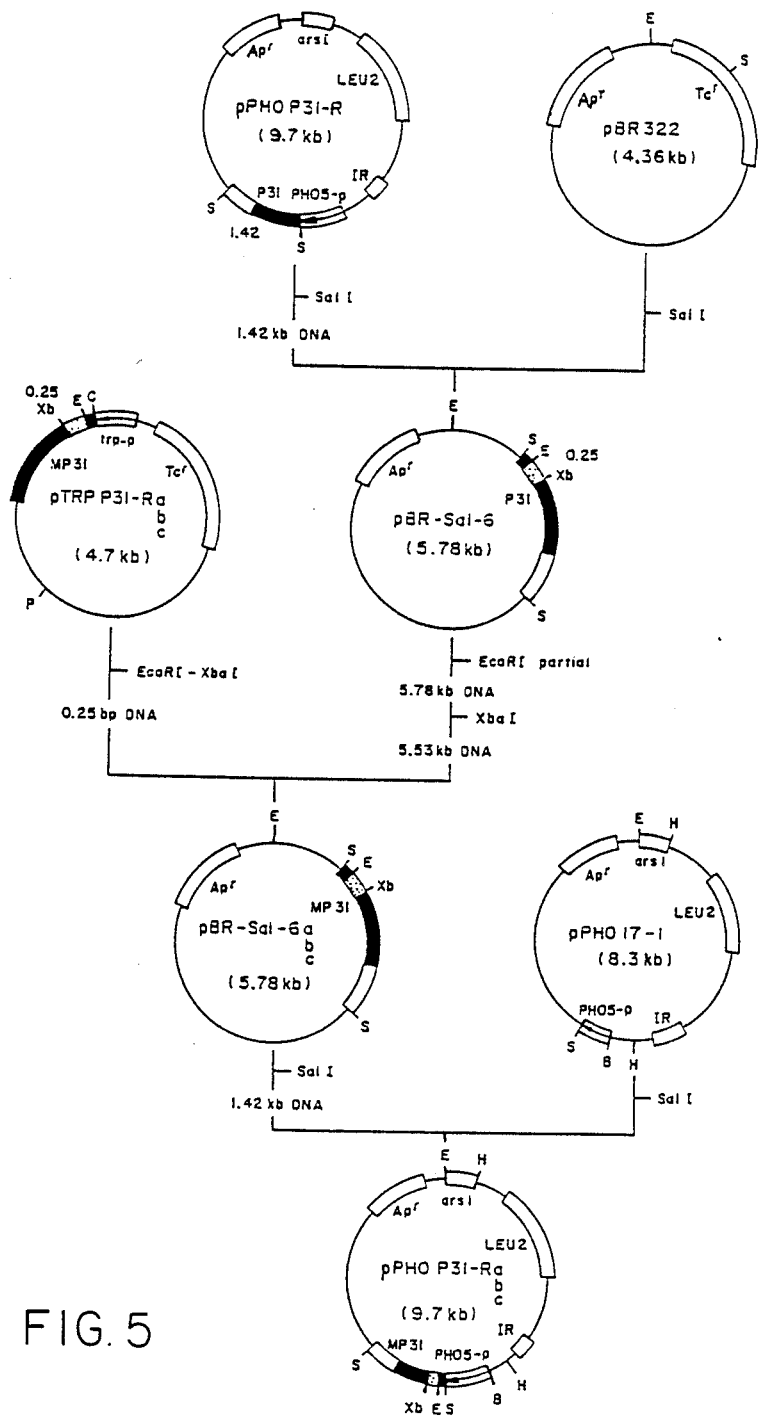
FIG. 5 shows the construction schemes for pPHO P31-Ra, pPHO P31-Rb and pPHO P31-Rc. In the figure, B, C, E, H, S and Xb stand for BamHI, ClaI, EcoRI, HindIII, SalI and XbaI, respectively.

Construction of modified P31 gene expression plasmid using exogenous gene expression vector having PHO-5 promoter and transformation of yeast with said plasmid 5 μg of the plasmid pPHO P31-R was digested with 10 units of the restriction enzyme SalI (Nippon Gene) in 30 μl of a reaction mixture [50 mM Tris-HCl (pH 7.5), 100 mM NaCl, 10 mM MgCl$_2$2, 1 dithiothreitol] at 37° C. for 2 hours. Thereafter, a 1.42 kb DNA fragment containing the P31 gene was separated on an agarose slab gel under the conditions mentioned above and said DNA was recovered from the gel. 0.5 μg of said DNA was mixed with 0.1 μg of pBR322 digested with the restriction enzyme SalI and ligation was effected using T4 DNA ligase. Transformation of *Escherichia coli* DH1 using the reaction mixture gave ampicillin-resistant transformants. From one of said transformants, there was obtained a plasmid, pBR-Sal-6, with a 1.42 kb DNA fragment containing the subtype adr P31 gene being inserted therein at the SalI site of pBR322 (FIG. 5).

20 μg of pBR-Sal-6 was digested with 10 units of the restriction enzyme EcoRI (Nippon Gene) in 50 μl of a reaction mixture [50 mM Tris-HCl (pH 7.5), 100 mM NaCl, 10 mM MgCl$_2$, 1 mM dithiothreitol] at 37° C. for 10 minutes (partial digestion) and a 5.78 kb DNA fragment, resulting from cleavage only at one of the two EcoRI sites existing in said plasmid, was separated on an agarose slab gel under the conditions mentioned above. Said DNA fragment was then recovered from the gel (FIG. 5), and 2 μg of said 5.78 kb DNA was digested with 4 units of the restriction enzyme XbaI (Nippon Gene) in 20 μl of a reaction mixture [50 mM Tris-HCl (pH 7.5), 100 mM NaCl, 10 mM MgCl$_2$, 1 mM dithiothreitol] at 37° C. for 2 hours. Agarose slab gel electrophoresis of the reaction mixture gave a 5.53 kb DNA (FIG. 5).

5 μg of pTRP P31-Ra was digested with 10 units of EcoRI and 10 units of XbaI, followed by 5% polyacrylamide slab gel electrophoresis in a buffer [100 mM Tris-HCl, 100 mM boric acid, 2 mM EDTA (pH 8.3)] at 150 V for 1 hour. After electrophoresis, a 0.25 kb DNA fragment was recovered. Furthermore, the same procedure was followed with pTRP P31-Rb and pTRP P31-Rc, and 0.25 kb DNA fragments were recovered respectively. 0.05 μg of each DNA fragment was mixed with 0.1 μg of the above-mentioned 5.53 kb DNA and ligation was carried out using T4 DNA ligase. The ligation mixture was used for transformation of *Escherichia coli* DH1 to give ampicillin-resistant transformants. From among the transformants obtained in this manner, a plasmid, pBR-Sal-6a, with the pTRP P31-Ra-derived 0.25 kb DNA fragment inserted therein, a plasmid, pBR-Sal-6b, with the pTRP P31 Rb-derived 0.25 kb DNA fragment inserted therein, and a plasmid, pBR-Sal-6c, with the pTRP P31-RC-derived 0.25 kb DNA fragment inserted therein were respectively recovered (FIG. 5).

5 μg of pBR-Sal-6a was digested with 10 units of the restriction enzyme SalI and a 1.42 kb DNA fragment containing an modified P31 gene was separated on an agarose slab gel under the conditions mentioned above and recovered from the gel. 0.2 μg of said DNA was mixed with 0.1 μg of a DNA derived from the plasmid pPHO 17-1 by digestion with SalI and ligation was performed using T4 DNA ligase. The reaction mixture was used for transformation of *Escherichia coli* DH1, which gave ampicillin-resistant transformants. From among said transformants, there was obtained a plasmid, pPHO P31-Ra, with the modified P31 gene inserted therein in the same directionality as that of the PHO-5 promoter. In the same manner, there were obtained a plasmid, pPHO P31-Rb, with the corresponding 1.42 kb DNA fragment obtained by digestion of pBR-Sal-6b with SalI being inserted therein in the same directionality as that of pPHO17-1, and a plasmid, pPHO P31-Rc, with the corresponding 1.42 kb DNA fragment obtained by SalI digestion of pBR-Sal-6c being inserted therein in the same directionality as that of pPHO 17-1 (FIG. 5).

pPHO P31-Ra, pPHO P31-Rb and pPHO P31-Rc were respectively used for transformation of the yeast host *Saccharomyces cerevisiae* AH22R$^-$ to give transformants (AH22R$^-$/pPHO P31-Ra, AH22R$^-$/pPHO P31-Rb and AH22R$^-$/pPHO P31-Rc).

EXAMPLE 4

Figure 6:
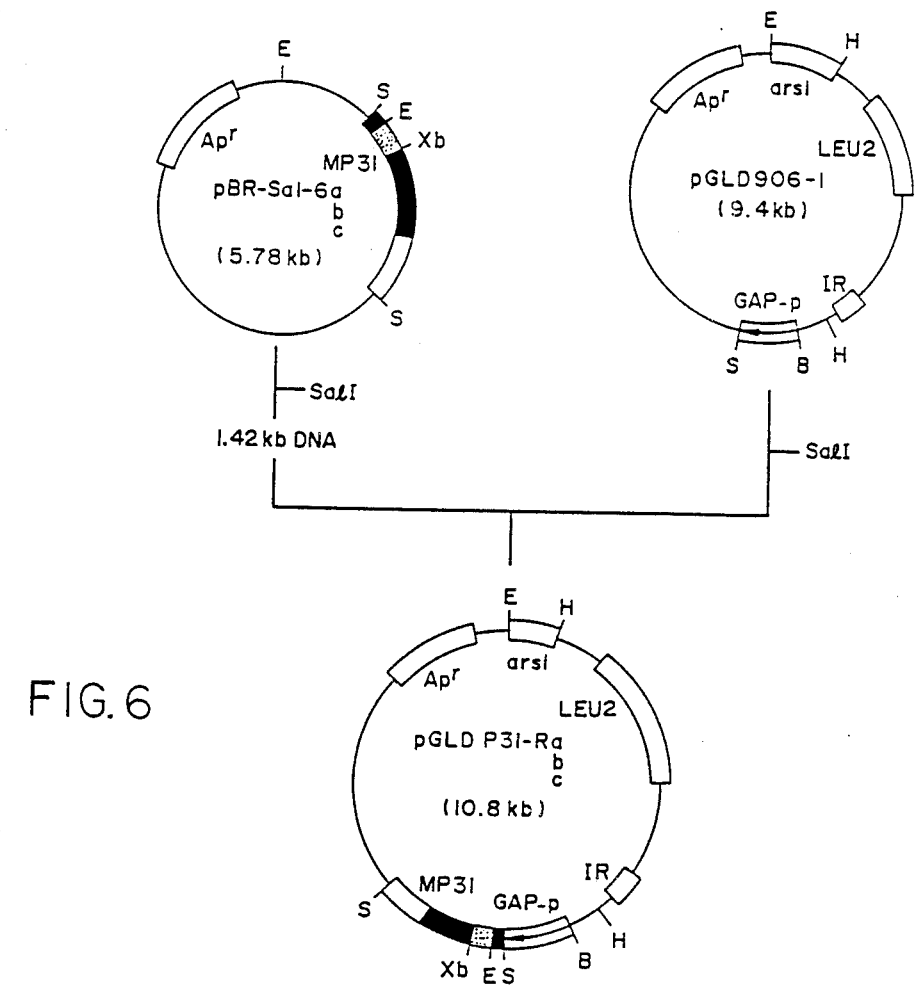
FIG. 6 shows the construction schemes for pGLD P31-Ra, pGLD P31-Rb and pGLD P31-Rc.
Figure 7:
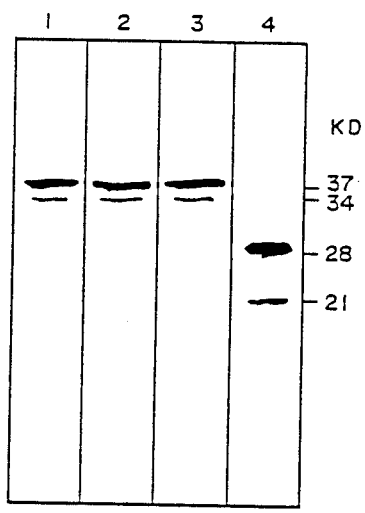
FIG. 7 shows the results of analysis by Western blotting of the extracts from cells of *Saccharomyces cerevisiae* AH22R⁻/pPHO P31-Ra (lane 1), AH22R⁻/pPHO P31-Rb (lane 2), AH22R⁻/pPHO P31-Rc (lane 3) and AH22R⁻/pPHO P31-R (lane 4).
Figure 1:
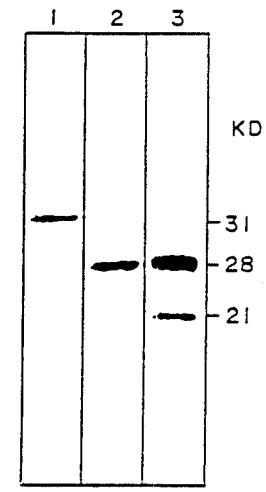
FIG. 1 shows the results of analysis of the gene products by Western blotting. In the figure, lane 1 shows the result of analysis of the extract from cells of *Escherichia coli* C600/pTRP P31-R, lane 2 that of the trypsin-treated extract from cells of *Escherichia coli* C600/pTRP P31-R and lane 3 that of the extract from cells of *Saccharomyces cerevisiae* AH22R⁻/pPHO P31-R.

Construction of modified P31 gene expression plasmid using an exogenous gene having a GLD promoter and transformation of yeast with said plasmid 0.1 μg of a DNA derived from the plasmid pGLD 906-1 by digestion with SalI was mixed with 0.2 μg of the pBR-Sal-6a-derived 1.42 kb DNA fragment described in Example 3 and ligation was carried out using T4 DNA ligase. Transformation of *Escherichia coli* DH1 with the ligation reaction mixture gave ampicillin-resistant transformants. From among said transformants, there was obtained a plasmid, pGLD P31-Ra, with the modified P31 gene inserted therein in the same directionality as that of the GLD promoter. In the same manner, there were obtained a plasmid, pGLD P31-Rb, with the pBR-Sal-6b-derived 1.42 kb DNA fragment described in Example 3 being inserted therein in the same directionality as that of pGLD 906-1, and a plasmid, pGLD P31-Rc, with the pBR- Sal-6c-derived 1.42 kb DNA fragment described in Example 3 being inserted therein in the same directionality as that of pGLD 906-1 (FIG. 6).

pGLD P31-Ra, pGLD P31-Rb and pGLD P31-Rc were respectively used for transformation of the yeast host *Saccharomyces cerevisiae* AH22R$^-$ to give transformants (AH22R$^-$/pGLD P31-Ra, AH22R$^-$/pGLD P31-Rb and AH22R$^-$/pGLD P31-Rc).

EXAMPLE 5

Expression of modified P31 gene in yeast

The yeast transformants carrying the modified P31 gene expression plasmids obtained in Examples 3 and 4 were each cultivated in Burkholder's and his low phosphate media at 30° C. for 2 days. Thereafter, cells were harvested and washed with physiological saline.

The cells were converted to spheroplasts using Zymolyase (Seikagaku Kogyo) by the method of Miyanohara, A. et al. [Proc. Natl. Acad. Sci. USA, 80, 1 (1983)]. 0.1% Triton X-100 was then added to the spheroplasts for extraction of the modified P31. The lysate was centrifuged at room temperature at 15,000 rpm for 15 minutes. The thus-obtained supernatant was measured for P31 activity using Auszyme II (Abbott). The results thus obtained are shown in Table 2. Each P31 yield was calculated on the per-liter-of-broth basis.

TABLE 2

| Yeast transformant | | Modified P31 (μg/l broth) |
|---|---|---|
| *Saccharomyces cerevisiae* | AH22R$^-$/pPHO P31-Ra | 259 |
| | AH22R$^-$/pPHO P31-Rb | 548 |
| | AH22R$^-$/pPHO P31-Rc | 1,391 |
| | AH22R$^-$/pGLD P31-Ra | 950 |
| | AH22R$^-$/pGLD P31-Rb | 950 |
| | AH22R$^-$/pGLD P31-Rc | 1,402 |

EXAMPLE 6

Production of modified P31 protein particles

The yeast transformant AH22R$^-$/pPHO P31-Rb produced in Example 2 was cultivated in Burkholder's low phosphate medium containing 5% glucose at 30° C. for 2 days. Cells were then harvested and washed with 0.85% NaCl. 20 g of the wet cells was suspended in 80 ml of 10 mM potassium phosphate buffer (KPB), pH 7.4, containing 8 mg of Zymolyase 60000, 10 mM EDTA, 1 mM phenylmethylsulfonyl fluoride (PMSF) and 14 mM 2-mercaptoethanol and lysis was effected by incubation at room temperature for 3 hours. The lysate was centrifuged at 8,000 rpm at 5° C. for 10 minutes.

The thus-obtained sediment, which contained the cell membrane and cell wall fragments, was suspended in 80 ml of 10 mM KPB (pH 7.4)-10 mM EDTA-1 mM PMSF, followed by centrifugation at 5° C. and 8,000 rpm for 10 minutes. The sediment thus obtained was again suspended in 10 mM KPB (pH 7.4)-10 mM EDTA-1 mM PMSF and a sediment was obtained by centrifugation. Said sediment, which was composed of the cell membrane and wall fragments, was suspended in 80 ml of 10 mM KPB (pH 7.4)-10 mM EDTA-1 mM PMSF-0.1% Triton X-100 and the mixture was stirred at 5° C. for 2 hours to thereby cause extraction of the modified P31 protein. Said suspension was subjected to centrifugation at 5° C. at 8,000 rpm for 10 minutes to give a supernatant. The content of the modified P31 protein in this extract was about 5–10%.

80 ml of said extract was applied to a DEAEToyopearl (Toyo Soda Kogyo) column (1.2×6.5 cm) equilibrated with 10 mM KPB (pH 7.4)-10 mM EDTA, followed by thorough washing of the column with 10 mM KPB (pH 7.4)-10 mM EDTA containing 0.1M NaCl. The modified P31 protein was then eluted by increasing the NaCl concentration progressively.

The modified P31 eluate fraction thus obtained was concentrated using an ultrafiltration membrane and the concentrate was subjected to gel filtration using a Sephacryl S-300 (Pharmacia) column (1.7×77 cm) equilibrated with 0.1M KPB (pH 7.4)-0.1M NaCl-10 mM EDTA. The modified P31 protein, eluted in the vicinity of the void volume, was layered on a 5–40% CsCl gradient in a Beckman SW41 centrifugal tube and centrifugation was carried out at 5° C. and 40,000 rpm for 16 hours.

The modified P31 fraction was dialyzed against mM KPB (pH 7.4)-10 mM EDTA and then layered on a 5–30% sucrose gradient in the above-mentioned centrifugal tube for SW41, followed by centrifugation at 5° C. and 38,000 rpm for 6 hours.

After centrifugation, a modified P31 protein-containing fraction was collected and subjected to SDS-polyacrylamide gel electrophoresis under reducing conditions, whereupon a main band corresponding to a molecular weight of 37 kilodaltons was detected.

EXAMPLE 7

Construction of plasmids pTB553 and pTB555 pTRP P31-R and pTRP P31-Rb (each 10 μg) were respectively treated with 100 units of EcoRI methylase (New England BioLabs) in 50 μl of a reaction mixture [50 mM Tris-HCl (pH 7.5), 1 mM EDTA, 5 mM DTT, 50 μM S-adenosylmethionine] at 37° C. for 1 hour. The EcoRI methylase was inactivated by heat treatment at 65° C. for 5 minutes and the DNA was recovered by precipitation with ethanol. This plasmid was digested with 30 units each of the restriction enzymes ClaI and PstI in 80 μl of a reaction mixture [10 mM Tris-HCl (pH 7.5), 10 mM MgCl$_2$,1 mM DTT, 50 mM NaCl] at 37° C. for 1 hour, followed by agarose slab gel electrophoresis. Thus were obtained a 1.4 kb DNA fragment containing either the P31 gene or the modified P31 gene. 2 μg of this DNA was filled in with 4 units of T4 DNA polymerase (PL) in 30 μl of a reaction mixture [33 mM Tris-acetate (pH 7.9), 66 mM K-acetate, 10 mM Mg-acetate, 100 μg/ml BSA,0.5 mM DTT, 0.2 mM dNTP] at 37° C. for 5 minutes. The reaction was terminated by addition of 4 μl of 0.2M EDTA (pH 7) and, after extraction with phenol-chloroform (1:1), the DNA was recovered by precipitation with ethanol. 2 μg of the DNA fragment with blunt termini was dissolved in 15 μl of a ligation buffer [66 mM Tris-HCl (pH 7.6), 6.6 mM MgCl$_2$, 10 mM DTT, 66 μM ATP]. Thereto were added 0.2 μg of an EcoRI linker phosphorylated at the 5' end [5'-P-d(GGAATTCC)] and 2 units of T4 DNA ligase and ligation was conducted at 14° C. for 17 hours. The ligase was inactivated by heat treatment at 65° C. for 10 minutes, 5 volumes of distilled water was added and further digestion with 30 units of the restriction enzyme EcoRI was performed in a reaction mixture for EcoRI [50 mM Tris-HCl (pH 8), 100 mM NaCl, 10 mM MgCl$_2$, 1 mM mercaptoethanol, 100 μg/ml BSA] for 3 hours. The linker and the linker-joined P31 DNA were separated from each other on a Sepharose 4B column (0.5 cm in diameter and 15 cm in length) and the EcoRI linker-joined P31 DNA was recovered by precipitation with ethanol.

Separately, the PstI cleavage site on the 5' end side and the BamHI site on the 3' end side of the IL-2 gene region of the plasmid pTB106 described in the specification to Japenese Patent Application No.133490/1985 [Japanese Unexamined Patent Publication No. 63282/1986] were each converted to an EcoRI site, the plasmid pIB389 missing the IL-2 gene region was cleaved with the restriction enzyme EcoRI, and the 5' end phosphoryl groups were eliminated by treatment with alkaline phosphatase.

Figure 8:
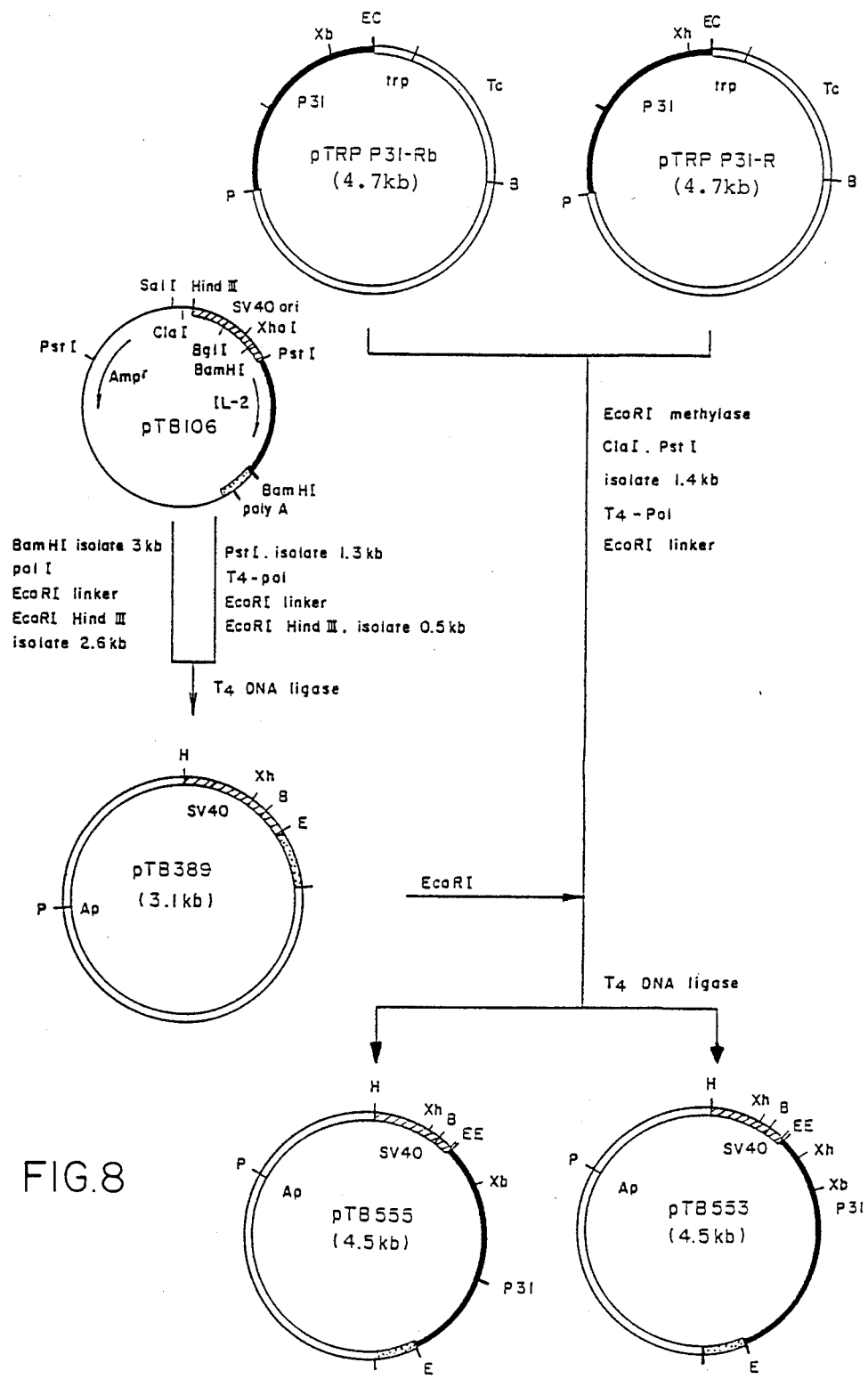
FIG. 8 shows the construction schemes for pTB553 and p-TB555.

The EcoRI linker-joined 1.4 kb DNA fragment was mixed with the pTB389 DNA-derived EcoRI fragment and ligation was performed in the presence of T4 DNA ligase. Thus were constructed SV40 promoter-containing plasmids for animal cell transformation, pTB553 (P31) and pTB555 (modified P31) (FIG. 8).

EXAMPLE 8

Construction of plasmids pTB556 and pTB558 pTB491, prepared by ligation of a 0.95 kb BamHI fragment of the plasmid pTB348 described in the specification to Japanese Patent Application No.133490/1985 [Japenese Unexamined Patent Publication No. 63282/1986] with a 3.8 kb BamHI fragment of the plasmid pTB399 described in said specification in the presence of T4 DNA ligase, was cleaved with the restriction enzymes HindIII and PstI and the 1.1 kb DHFR (dihydrofolate reductase) DNA was separated.

Furthermore, a plasmid, pTB308, was constructed by treating with S1 nuclease a 0.9 kb HindIII-SacI DNA fragment of λY73-11A with the avian sarcoma virus (ASV) LTR cloned therein [Kitamura et al., Nature, 297, 205–208 (1982)], ligating the so-treated DNA with a HindIII linker and inserting the ligation product into pTB106 at the HindIII cleavage site. This plasmid was then deprived of the HindIII cleavage site upstream from ASV LTR (pTB311) and thereafter cleaved ,with the restriction enzymes XhoI and HindIII to thereby eliminate the SV40 promoter region (pTB313), followed by elimination of a 0.3 kb fragment by cleavage with the restriction enzyme BstXI to convert the double ASV LTR to a single ASV LTR. Thus was constructed pTB401. This plasmid was cleaved with the restriction enzymes SalI and PstI to give an ASV LTR-containing 0.8 kb fragment.

Figure 9:
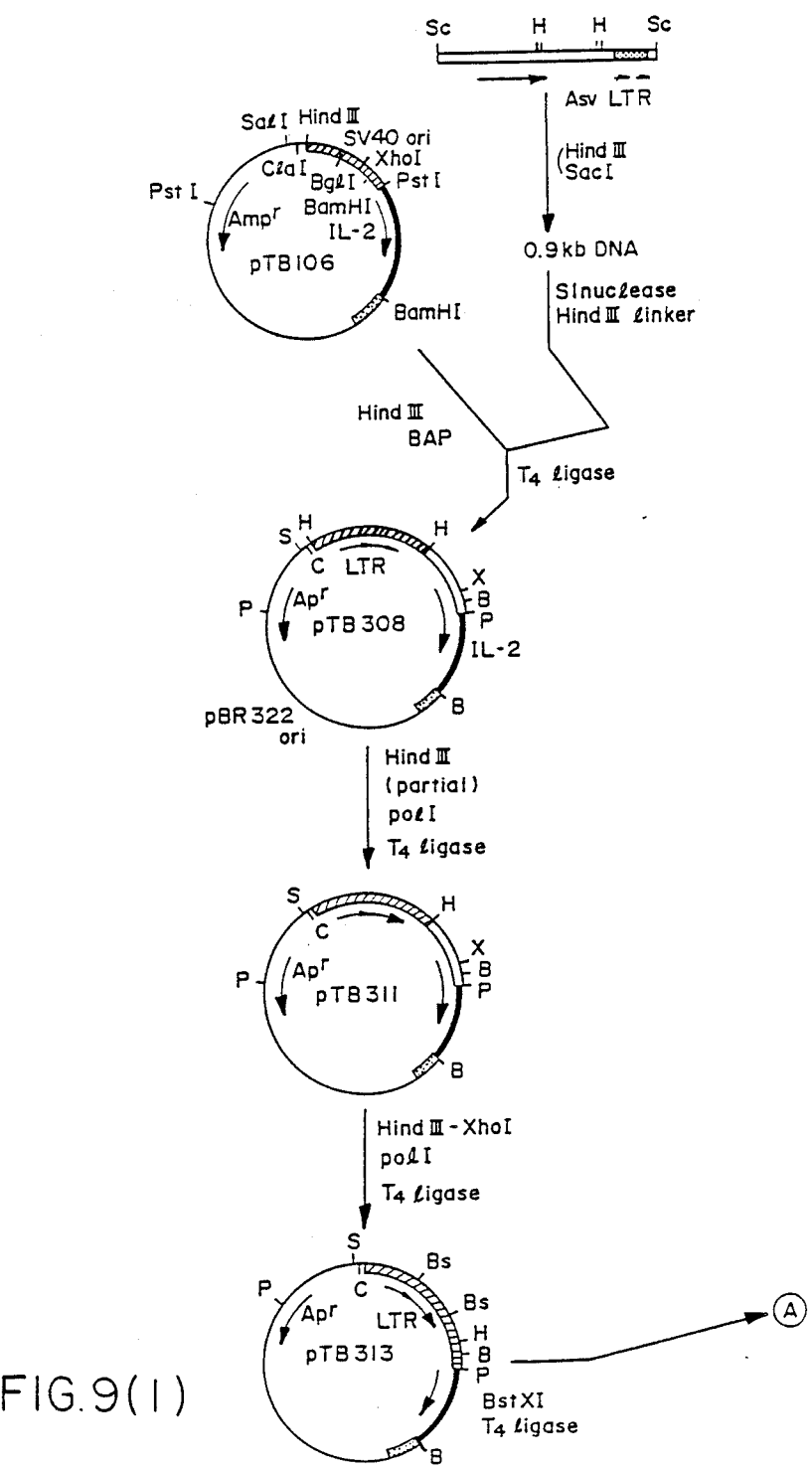
FIG. 9 (1-3) shows the construction schemes for pTB556 and PTB558.
Figure 9:
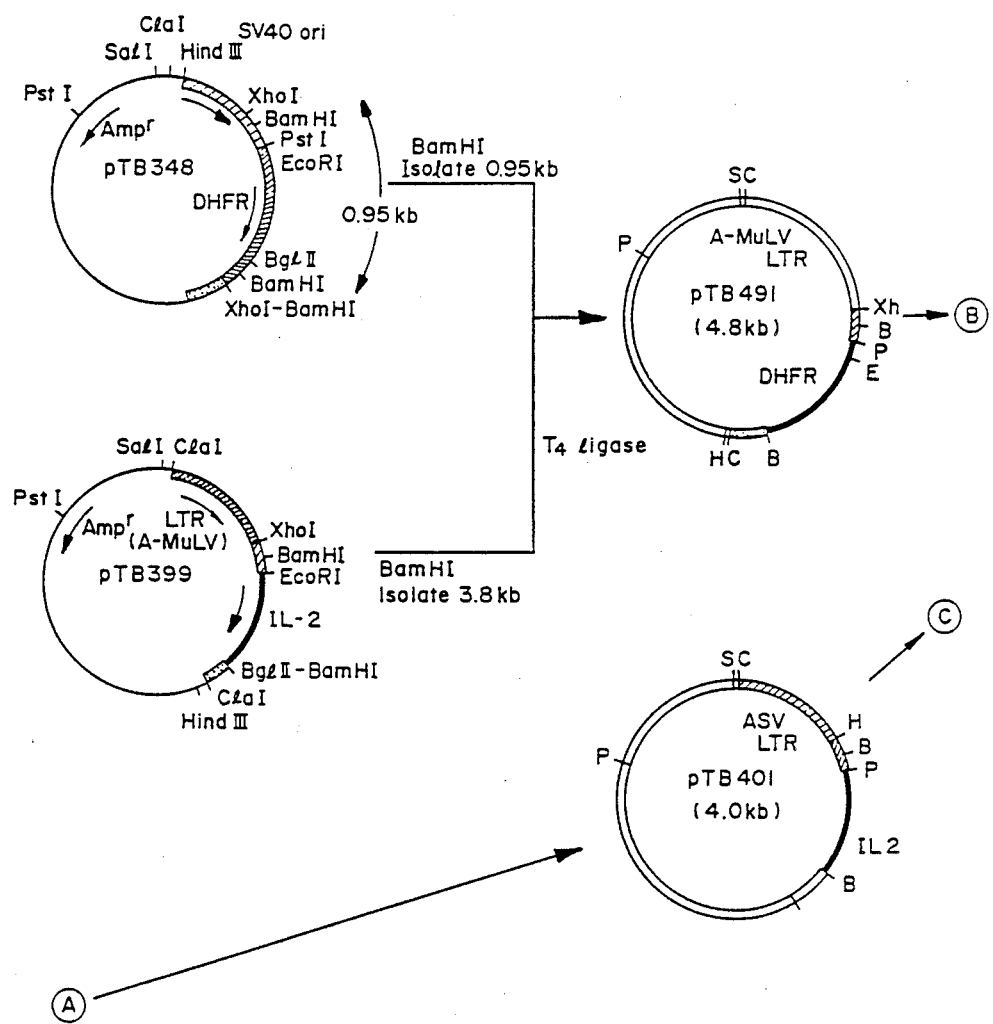
Figure 9:
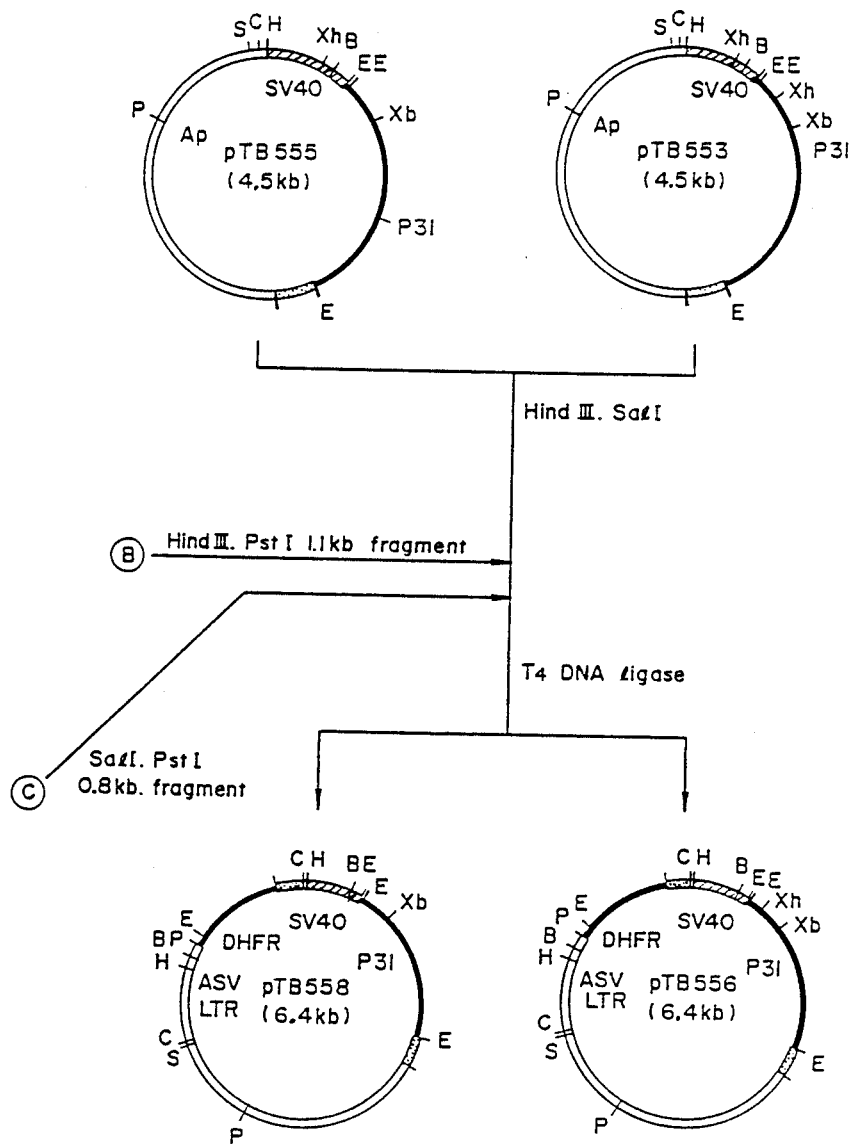

The DHFR DNA-containing 1.1 kb HindIII-PstI fragment and ASV LTR-containing 0.8 kb SalI-PstI fragment both mentioned above were mixed with a fragment derived from pTB553 or pTB555 by cleavage with the restriction enzymes HindIII and SalI and ligation was conducted in the presence of T4 DNA ligase. Thus were constructed pTB556 (P31) and pTB558 (modified P31) (FIG. 9). These plasmids have a structure such that the DHFR gene with ASV LTR as the promoter and the P31 gene or modified P31 gene with the SV40 replication initiation region as the promoter are joined together in the same direction.

EXAMPLE 9

Transformation of animal cells

Eagle's MEM medium containing 10% bovine fetal serum was distributed into Falcon dishes (6 cm in diameter) and mouse TK-deficient L cells were cultured overnight at 37° C. Thereafter, these cells ($7 \times 10^5$ cells per dish) were mixed with and thereby inoculated with 0.2 μg of the plasmid pTK61 [obtained by isolating the plasmid from *Escherichia coli* LE578 (Gene, 7, 335–342 (1979); gift of Dr. Enquist) carrying a pBR322-derived recombinant with a herpes simplex virus (HSV) TK gene-containing 3.5 kb BamHI DNA fragment cloned therein and then re-cloning a TK gene-containing 2 kb PvuII fragment (Proc. Natl. Acad. Sci. USA, 78, 1441–1445 (1981)) in pBR322] and 10 μg of the pTB553 or pTB555 DNA according to the method of Graham et al. [Virology, 52, 456–467 (1973)]. After cultivation at 37° C. for 4 hours, the medium was replaced with a fresh portion of medium and cultivation was continued overnight. On the next day, the medium was replaced with 10% bovine fetal serum-containing HAT medium (MEM medium containing 15 μg/ml hypoxanthine, 1 μg/ml aminopterine, 5 μg/ml thymidine and 0.25 μg/ml glycine). In about 2–3 weeks of continued cultivation ion at 37° C. with medium exchange at 3- or 4-day intervals, cells which had become TK+ multiplied and formed colonies.

As for the plasmids pTB556 and pTB558, DHFR− CHO cells [Urlaub et al., Proc. Natl. Acad. Sci. USA, 77, 4216–4220 (1980)] were cultivated in HAM F12 medium containing 5% bovine fetal serum and gene infection was attained according to the method of Graham et al. (vide supra) using 1 μg of plasmid per dish. After 2 days, the medium was replaced with Dulbecco's modified MEM medium containing 10% dialyzed bovine fetal serum and 35 μg/ml proline and, thereafter, cultivation was continued in this selective medium. In about 2–3 weeks, cells which had become DHFR+ multiplied and formed colonies.

EXAMPLE 10

Cloning of transformants

The respective transformant cells obtained in Example 9 were cloned by a known method (e.g. the limited dilution method). After completion of cloning, each L(TK+) cell clone was cultivated in Eagle's MEM medium containing 10% bovine fetal serum, while each CHO(DHFR+) cell clone was cultivated in Dulbecco's modified MEM medium containing 5% bovine fetal serum and 35 μg/ml proline. For each clone isolated, the cell culture supernatant was assayed for HBsAg activity using Ausria II-125 (Dianabbott).

The results thus obtained are shown in Table 3.

TABLE 3

| Plasmid | Transformant (clone) | HBsAg cpm |
| --- | --- | --- |
| pTB553 | L-P31-553-10 | 4,287 |
| pTB555 | L-P31-555-4 | 2,278 |
| pTB556 | C-P31-556-2 | 1,137 |

TABLE 3-continued

| Plasmid | Transformant (clone) | HBsAg cpm |
| --- | --- | --- |
| pTB558 | C-P31-558-1 | 3,002 |

EXAMPLE 11

Endo-β-N-acetylglucosaminidase H treatment of modified P31 gene product 0.1 g of wet cells of the strain *Saccharomyces cerevisiae* AH22R−/pPHO P31-Rb described in Example 6 were disrupted by suspending them in 0.5 ml of 7.5M urea-10 mM KPB (pH 7.4)-10 mM EDTA-1 mM PMSF, adding 1 g of glass beads 0.45–0.5 mm in diameter and stirring vigorously with a mixer (Taiyo Kagaku automatic mixer). The resultant mixture was centrifuged at 5° C. at 12,000 rpm for 10 minutes to give a supernatant. To 0.2 ml of said supernatant, there was added an equal volume of 0.2M 2-mercaptoethanol-0.4% SDS-100 mM sodium citrate buffer (pH 5.5), and the protease in the extract was inactivated by heat treatment at 95° C. for 5 minutes. To 0.4 ml of said extract was added 0.8 ml of cold ethanol and, after standing on ice for 15 minutes, the mixture was centrifuged at 5° C. at 12,000 rpm to give a sediment. Said sediment was suspended in 0.2 ml of 50 mM citrate buffer (pH 5.5). To a 0.1-ml portion of the suspension, there was added 0.05 unit of endo-β-N-acetylglucosaminidase H (Seikagaku Kogyo). After 2 hours of reaction at 37° C., a sample of the reaction mixture as well as a sample of the unreacted sediment was subjected to SDS-polyacrylamide gel electrophoresis under reducing conditions, and the protein was transferred onto a nitrocellulose membrane using a transblotting device (Bio-Rad). The subsequent testing for HBsAg using a peroxidase-labeled anti-HBsAg antibody (Auszyme II; Abbott Laboratories) and an immune blot assay kit (Bio-Rad) revealed that the sample of the reaction mixture contained a 34-kilodalton P31 gene product. The use of monoclonal antibodies to HBsAg gave the same results. This means that the product of the 37-kilodalton modified P31 gene has a sugar chain added thereto and that a part of said sugar chain can be cleaved off with endo-β-N-acetylglucosaminidase H.

EXAMPLE 12

Construction of modified P31 gene having glutamine codons in lieu of codons of subtype adr P31 gene for 16th and 18th amino acids (arginine)

10 μg of the plasmid pBR-Sal-6c described in Example 3 was digested with 20 units of SalI and 20 units of XbaI in 20 μl of a reaction mixture [50 mM Tris-HCl (pH 7.5), 100 mN NaCl, 10 mM MgCl₂, 1 mM dithiothreitol] at 37° C. for 2 hours, followed by 5% polyacrylamide slab gel electrophoresis of the reaction mixture. After electrophoresis, the gel piece containing a 0.25 kb DNA fragment was sealed in a dialysis tube and the 0.25 kb DNA fragment was recovered by the method described in Example 1. 0.2 μg of the double-stranded phage vector M13mp11 DNA [Messing, J., Methods in Enzymology, 101, 20 (1983)] was digested with 2 units of SalI and 2 units of XbaI in 20 μl of a reaction mixture [50 mM Tris-HCl (pH 7.5), 100 mM NaCl, 10 mM MgCl₂, 1 mM dithiothreitol] for 2 hours to thereby cleave the DNA at the SalI and XbaI sites. The restriction enzymes were inactivated by heat treatment of said reaction mixture at 65° C. for 5 minutes. To 0.01 μg of said DNA was added 0.5 μg of the above-mentioned 0.25 kb DNA fragment and both the DNAs were ligated together in 10 μl of a reaction mixture in the presence of T4 DNA ligase, and the ligation product was introduced into *Escherichia coli* JM103 by the method of Messing, J. [Methods in Enzymology, 101, 20 (1983)] and allowed to to form plagues. From among white plaques, there was obtained M13mp11-101 with the above-mentioned 0.25 kb DNA fragment cloned in M13mp11.

A phage DNA (single-stranded DNA) was prepared fro M13mp11-101 phage particles by the method of Messing, J., supra. Using said single-stranded DNA, oligonucletide-directed mutagenesis [Smith, M. and Gilliam, S., Genetic Engineering, 3, 1 (1981)] was carried out in the following manner. To 1 μg of the single-stranded M13mp11-101 DNA, there was added 18 ng of a primer comprising a DNA synthesized by the phosphotrieter method and phosphorylated at the 5' end using T4 polyncucleotide kinase, 5'-P-(AGGCCTT-GCACTTGGGGATCTAG) and, after heat treatment at 90° C. for 5 minutes in 10 μl of a reaction mixture [10 mM Tris-HCl (pH 7.5), 10 mM MgCl$_2$], annealing was effected by allowing the mixture to stand at room temperature for 30 minutes. To said reaction mixture was added 10 μl of a reaction mixture [10 mM Tris-HCl (pH 7.5), 1 mM ATP, 1 MgCl$_2$, 1 mM dATP, 1 mM dCTP, 1 mM dGTP, 1 mM dTTP, 10 mM DTT, 2 units of DNA polymerase I large fragment (Takara Shuzo), 0.5 unit of T4 DNA ligase] and the single-stranded DNA was repaired to the double-stranded form by reaction at room temperature for 16 hours. Using the reaction mixture, *Escherichia coli* JM103 was transformed by the above-mentioned method of Messing, J. and plaque formation was allowed to take place. Plaque hybridization [Benton, W. D. and Davis, W. R., Science, 196, 180 (1977)] was performed in order that a phage DNA containing the same sequence as that of the above synthetic primer could be selected from among the plaques obtained. 1 μg of the above-mentioned chemically synthesized DNA d(AGGCCTTGCACTTGGGGATC-TAG) was labeled with $^{32}$P at the 5' end by reacting with 20 μCi of γ-[$^{32}$P]ATP (Amersham) using 5 units of T4 polynucleotide kinase (Takara Shuzo) in 30 μl of a reaction mixture [50 mM Tris-HCl (pH 7.6), 10 mM MgCl$_2$, 10 mM 2-mercaptoethanol] at 37° C. for 30 minutes. An equal volume of phenol was added to the reaction mixture to effect deproteinization Thereafter, the reaction mixture was applied to a Sepharose 4B (Pharmacia) column (0.25×25 cm) equilibrated with TEN buffer [10 mM Tris-HCl (pH 8.0), 200 mM NaCl, 1 mM EDTA], and the first eluate $^{32}$P-labeled synthetic DNA was recovered and used as a probe for plaque hybridization. Plaque hybridization was carried out by the method of Benton, W. D. and Davis, R. W., supra. About 4,000 plaques were examined and, as a result, 36 plaques were found to hybridize with the probe. From one of the plaques, the phage DNA was isolated, and analysis of the DNA base sequence by the M13 dideoxy method described in Example 1 confirmed conversion of each of the Arg16 and Arg18 codons of the P31 gene to a Gln codon. Said phage was named M13mp11-102.

Figure 15:
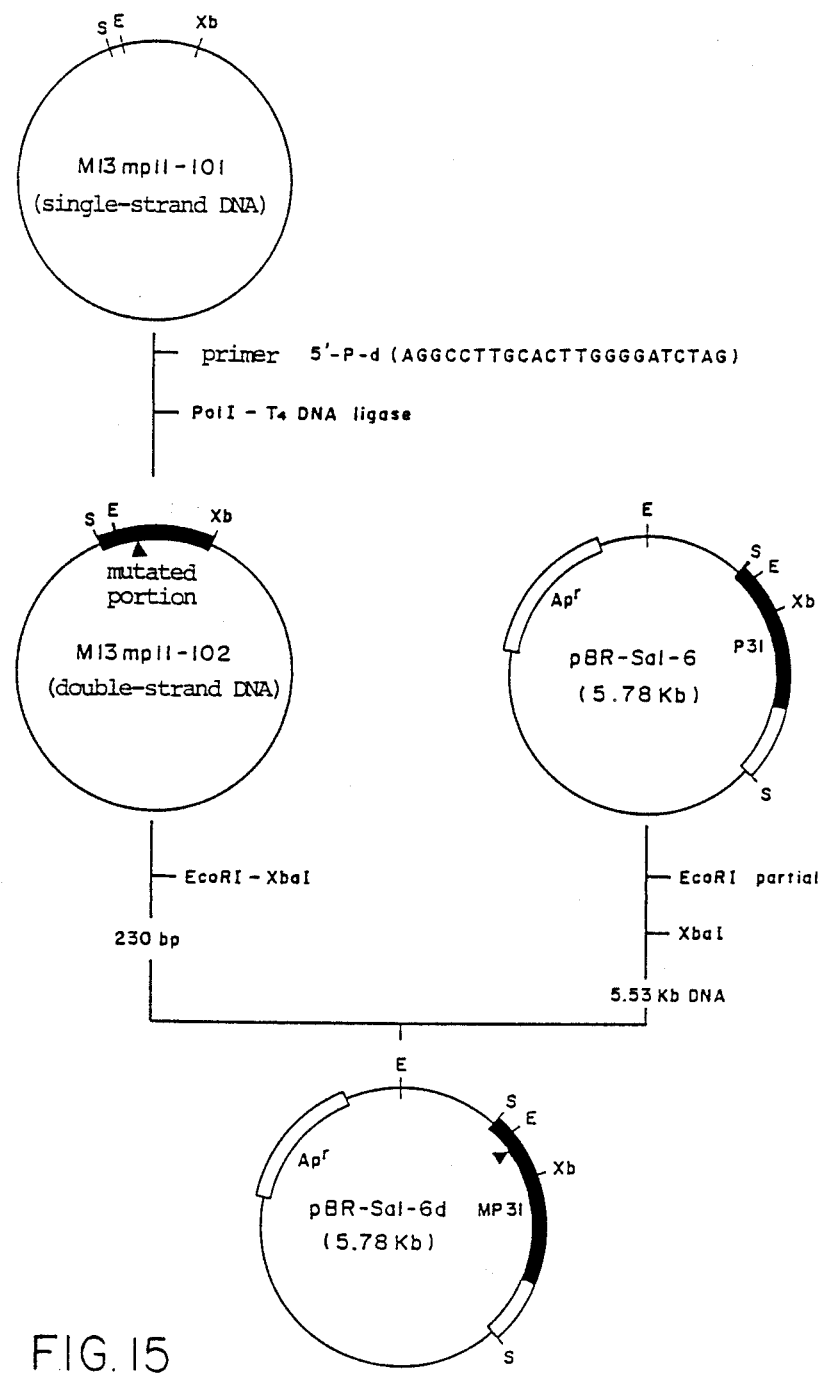
FIG. 15 shows the construction scheme for the plasmid pBR Sal-6d.

20 μg of the double-stranded M13mp11-102 DNA was digested with 40 units of EcoRI and 40 units of XbaI in 100 μl of a reaction mixture [50 mM Tris-HCl (pH 7.5), 100 mM NaCl, 10 mM MgCl$_2$, 1 mM dithiothreitol] at 37° C. for 2 hours, followed by 5% polyacrylamide slab gel electrophoresis, by which a 230 bp DNA fragment was separated and recovered from the gel. 0.05 μg of said DNA fragment was mixed with 0.1 μg of the pBR-Sal-6-derived 5.53 kb DNA fragment described in Example 2 and ligation was carried out using T4 DNA ligase. Transformation of *Escherichia coli* DH1 with the ligation mixture gave ampicillin-resistant transformants. From among said transformants, there was obtained a plasmid, pBR-Sal-6d, with the M13mp11-102-derived 230 bp DNA fragment inserted therein (FIG. 15). The modified P31 gene contained in said plasmid is a gene missing the codn for Arg48 which is susceptible to cleavage with protease and having Gln codons in lieu of the Arg16 and Arg18 codons.

EXAMPLE 13

Figure 16:
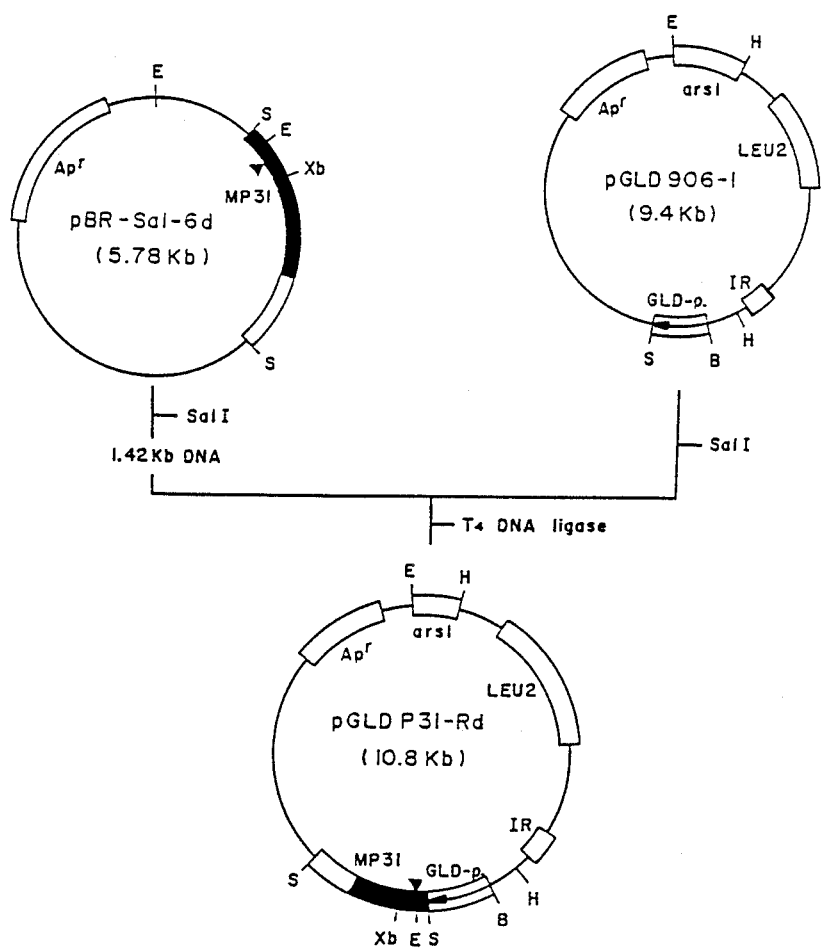
FIG. 16 shows the construction scheme for the plasmid pGLD P31-Rd.

Construction of modified P31 gene expression plasmid using exogenous gene expression vector having GLD promoter and transformation of yeast with said plasmid 5 μg of the plasmid pBR-Sal-6d described in Example 12 was digested with 10 units of SalI and a modified P31 gene-containing 1.42 kb DNA fragment was separated by agarose slab gel electrophoresis and said DNA was recovered from the gel. 0.2 μg of said DNA was mixed with 0.1 μg of the DNA derived from the plasmid pGLD 906-1 described in Reference Example 3 by digestion with SalI and ligation was effected using T4 DNA ligase. The reaction mixture was used for transformation of *Escherichia coli* DH1 to give ampicillin-resistant transformants. From among said transformants, there was obtained a plasmid, pGLD P31-Rd, with the modified P31 gene inserted therein in the same directionality as that of the GLD promoter (FIG. 16).

Using pGLD P31-Rd, the yeast host *Saccharomyces cerevisiae* AH22R$^-$ was transformed and a non-leucine-requiring transformant, AH22R$^-$/pGLD P31-Rd, was obtained.

EXAMPLE 14

Construction of modified P31 gene expression plasmid having PGK terminator connected downstream from modified P31 gene and transformation of yeast with said transformant The plasmid pPKT 3 having the phosphoglycerate kinase (PGK) gene inserted therein as described in Reference Example 2 contains an about 290 bp 3'-non-coding region of the PGK gene. The presence in said region of a terminator for terminating messenger RNA synthesis has been demonstrated by Hitzeman, R. A. et al. [Nucleic Acids Res., 10, 7791–7808 (1982)]. For expediting completion of the transcription of the modified P31 gene, it was attempted to connect the 3'-non-coding region of the PGK gene immediately behind the modified P31 gene.

Thus, 60 μg of the plasmid pPKT3 was digested with 50 units each of the restriction enzymes ClaI and HindIII in 100 μl of a reaction mixture [10 mM Tris-HCl (pH 7.5), 50 mM NaCl, 10 mM MgCl$_2$] at 37° C. for 5 hours, followed by 5% polyacrylamide slab gel electrophoresis in a buffer [100 mM Tris-HCl, 100 mM boric acid, 2 mM EDTA (pH 8.3)] at 150 V for 2 hours. After electrophoresis, the gel piece containing a 0.28 kb DNA fragment was sealed in a dialysis tube and the 0.28 kb DNA fragment was eluted from the gel by the method described in Reference Example 1, followed by extraction with phenol and with ether. Thereafter, said DNA was recovered by adding ethanol.

Since the above 0.28 kb DNA fragment was deficient in 20 bp from the stop codon out of the 3'-non-coding region, the missing DNA sequence was chemically synthesized. Thus, a DNA having the sequence

was synthesized by the above-mentioned method of Crea, R. et al. and phosphorylated on the 5' sides under the conditions described in Reference Example 1.

10 μg of the plasmid pBR-Sal-6d described in Example 12 was digested with 10 units of the restriction enzyme SalI and 10 units of the restriction enzyme AhaIII in 50 μl of a reaction mixture [50 mM Tris-HCl (pH 7.5), 100 mM NaCl, 10 mM $MgCl^2$, 1 mM dithiothreitol] at 37° C. for 2 hours and the reaction mixture was subjected to 0.8% agarose slab gel electrophoresis to thereby separate a 0.85 kb DNA fragment containing the modified P31 gene. Said DNA was recovered from the gel.

0.2 μg of the 3.74 kb DNA fragment obtained by digestion of the plasmid pBR322 with the restriction enzymes HindIII and SalI, 0.05 μg of the above 0.28 kb DNA fragment (containing the terminator for the PGK gene), 50 ng of the above-mentioned phosphorylated, chemically synthesized DNA and 0.1 μg of the above-mentioned 0.85 kb DNA fragment (containing the modified P31 gene) were mixed together and ligation was carried out in the presence of T4 DNA ligase under the conditions described in Reference Example 1. The reaction mixture was used for transformation of Escherichia coli DH1 and, from among the ampicillin-resistant transformants obtained, a transformant carrying a plasmid, pBR-Sal-6dT, composed of the four DNA fragments ligated together was isolated. Then, following the procedure described in Reference Example 1, the HindIII site of said plasmid pBR-Sal-6dT was converted to a SalI site to give a plasmid, pBR-Sal-6dTS.

Figure 17:
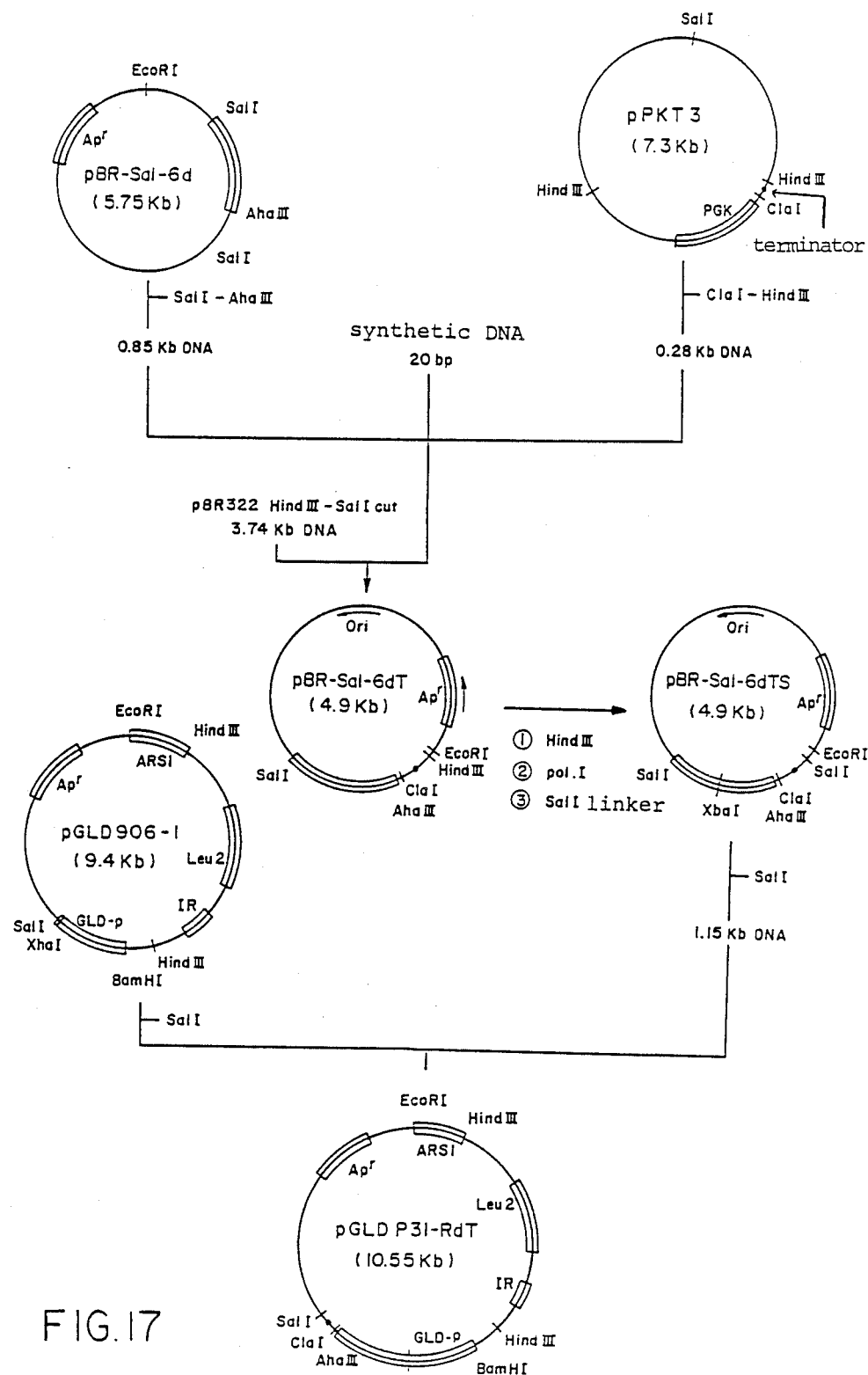
FIG. 17 shows the construction scheme for the plasmid pGLD P31-RdT.

5 μg of pBR-Sal-6dTS was digested with 10 units of the restriction enzyme SalI in 30 μl of a reaction mixture [50 mM Tris-HCl (pH 7.5), 100 mM NaCl, 10 mM $MgCl_2$, 1 mM dithiothreitol]at 37° C. for 2 hours. Then, a 1.15 kb DNA fragment containing the modified P31 gene and PGK terminator was separated on an agarose slab gel under the conditions mentioned above and said DNA was recovered from the gel. 0.5 μg of said DNA was mixed with 0.1 μg of a DNA derived from the plasmid pGLD 906-1 by digestion with SalI and ligation was effected using T4 DNA ligase. The reaction mixture was used for transformation of Escherichia coli DH1 to give ampicillin-resistant transformants. From one of said transformants, there was obtained a plasmid, pGLD P31-RdT, with the modified P31 gene-PGK terminator inserted therein in the same directionality as that of the GLD promoter (FIG. 17).

Using pGLD P31-RdT, the yeast host Saccharomyces cerevisiae AH22R⁻ was transformed and a transformant (AH22R⁻/pGLD P31-RdT) was isolated.

EXAMPLE 15

Expression of modified P31 gene in yeast

The yeast transformants carrying the respective modified P31 gene expression plasmids as obtained in Examples 13 and 14 were each cultured with shaking in 5 ml of a medium [containing, per liter, 3 g $K_2HPO_4$, 30 g glucose, 4 g asparagine, 100 mg L-histidine, 0.1 mg KI, 500 mg $MgSO_4\cdot 7H_2O$, 330 mg $CaCl_2\cdot 2H_2O$, 0.4 mg $CuSO_4\cdot 5H_2O$, 2.5 mg $FeSO_4\ 7H_2O$, 0.4 mg $MnSO_4\cdot 4H_2O$, 0.2 mg $(NH_4)_3PO_4\cdot 12MoO_3\cdot 3H_2O$, 3.1 mg $ZnSO_4\cdot 7H_2O$, 10 mg inositol, 0.2 mg thiamine, 0.2 mg pyridoxine, 0.2 mg Ca pantothenate, 0.2 mg niacin and 0.002 mg biotin] at 30° C. for 1 day. Then, 2 ml of the culture broth was transferred to 18 ml of a fresh medium [containing, per liter, 300 mg $KH_2PO_4$, 50 g sucrose, 4 g asparagine, 100 mg L-histidine, 1.5 g KCl, 0.1 mg KI, 500 mg $MgSO_4\cdot 5H_2O$, 330 mg $CaCl_2\cdot 2H_2O$, 10 g glucose, 25 mM Tris-maleate (pH 6.5), 0.4 mg $CuSO_4\cdot 5H_2O$, 2.5 mg $FeSO_4\cdot 7H_2O$, 0.4 mg $MnSO_4\cdot 4H_2O$, 0.2 mg $(NH_4)_3PO_4\cdot 12MoO_3\cdot 3H_2O$, 3.1 mg $ZnSO_4\cdot 7H_2O$, 10 mg inositol, 0.2 mg thiamine, 0.2 mg pyridoxine, 0.2 mg Ca-pantothenate, 0.2 mg niacin and 0.002 mg biotin] and cultivation with shaking was further carried out at 30° C. for 2 days. Cells were then harvested by centrifugation, and a cell extract was obtained by the procedure described in Example 5 and assayed for P31 activity. As a result, the P31 production by AH22R⁻/pGLD P31-Rd was calculated as 29 μg per milliliter of broth, and the P31 production by AH22R⁻/pGLD P31-RdT was calculated as 47 μg per milliliter of broth.

EXAMPLE 16

(1) Extraction from cells

Frozen and stored cells (1 kg) of the yeast Saccharomyces cerevisiae AH22R⁻/pGLD P31-Rd as obtained by cultivation by the method described in Example 15 followed by freezing at −20° C. were uniformly suspended in 4,000 ml of a buffer (pH 7.5) containing 7.5 M urea, 10 mM tetrasodium ethylenediaminetetraacetate (EDTA), 2 mM phenylmethylsulfonyl fluoride(PMSF), 0.1 mM (p-amidinophenyl)methanesulfonyl fluoride hydrochloride (P-APMSF) and 10 mM sodium phosphate. This suspension was treated in a Dynomill model KDL ball mill (WAB, Basel, Switzerland) at a flow rate of 4,000 ml/hr using glass beads of 0.50–0.75 mm to thereby disrupt cells continuously. For increasing the extraction efficiency, this procedure was repeated twice. Centrifugation of the extract at 13,900 ×g for 30 minutes gave 5,500 ml of a supernatant. The HBsAg concentration was 4.2 μg/ml as determined with Auszyme.

(2) Fractionation with polyethylene glycol

To the supernatant obtained in the above, there was added 0.5 volume of 33% (w/w) polyethylene glycol 6000 (PEG-6000) gradually, followed by centrifugation at 13,900 ×g for 30 minutes, by which the HBsAg fraction was recovered as a sediment. The sediment obtained was dissolved in 1,000 ml of a buffer (pH 7.5) containing 7.5 M urea, 10 mM EDTA, 2 mM PMSF, 0.1 mM P-APMSF and 10 mM sodium phosphate, and sodium chloride was added to a final concentration of 0.2 M. To this solution was added 0.25 volume of 33% (w/w) PEG-6000, followed by centrifugation at 13,900 ×g for 30 minutes. To the thus-obtained supernatant, there was again added 0.5 volume of 33% (w/w) PEG-6000, followed by centrifugation at 13,900 ×g for 30 minutes, which gave a sediment. This sediment was dissolved in 120 ml of 5.0 M urea-0.145 M sodium chloride-5 mM EDTA-1 mM PMSF-0.05 mM P-APMSF-10 mM sodium phosphate buffer (pH 7.5).

(3) Gel filtration using Sephacryl S-300

A Sephacryl S-300 (Pharmacia, Sweden) column (5×102 cm, 2,000 ml) equilibrated with 5.0 M urea-5 mM EDTA-1 mM PMSF-0.05 mM P-APMSF-10 mM sodium phosphate buffer (pH 7.5) was loaded with the solution obtained in the above and elution was conducted with the same buffer. A 240-ml eluate fraction corresponding to the void volume of the column was collected.

(4) Ultracentrifugation

On 8.5 ml of 40% cesium chloride (CsCl)-5 M urea-2 mM EDTA-1 mM PMSF-0.05 MM P-APMSF-10 mM potassium phosphate buffer (pH 7.4) placed in a ultracentrifuge tube for Beckman SW-28, there was layered 8.5 ml of 30% CsCl-5 M urea-2 mM EDTA-1 mM PMSF-0.05 mM P-APMSF-10 mM potassium phosphate buffer (pH 7.4) and, further, 20 ml of the above-mentioned solution was layered thereon. Ultracentrifugation was carried out at 28,000 rpm and 4° C. for 16 hours, whereby HBsAg was concentrated and purified in the vicinity of a density of about 1.2.

(5) Hydroxylapatite column

The HBsAg fraction concentrated and purified by ultracentrifugation was dialyzed against 50 mM potassium phosphate buffer (pH 7.0) containing 0.05 mM P-APMSF for a day and then passed through a hydroxylapatite column (2.5×10 cm, 50 ml) equilibrated with the above-mentioned buffer for adsorption of HBsAg, followed by washing of the column with the above buffer for equilibration.

HBsAg was then eluted by the linear concentration gradient elution method using 300 ml of 50 mM potassium phosphate buffer (pH 7.0) containing 0.05 mM P-APMSF and 300 ml of 600 mM potassium phosphate buffer (pH 7.0) containing 0.05 mM P-APMSF. The HBsAg fraction was collected, dialyzed against PBS and passed through a membrane filter to give 42 ml of a purified HBsAg solution having an HBsAg protein concentration of 65 μg/ml.

10 ml of the above solution was mixed with 55 ml of an alum solution having a concentration of 1.18 mg/ml at 4° C. for 3 hours to thereby cause adsorption of HBsAg on alum. Thus was obtained 65 ml of a vaccine having an HBsAg concentration of 10 μg/ml.

EXAMPLE 17

Construction of modified P31 gene expression plasmid having PGK terminator connected downstream from modified P31 gene and transformation of yeast with said transformant 10 μg of the plasmid pBR-Sal-6c described in Example 3 was treated with 10 units of restriction enzyme Sal I and 10 units of restriction enzyme Xba I in 50 μl of a reaction mixture [50 mM Tris-HCl (pH 7.5), 100 mM NaCl, 10 mM MgCl₂, 1 mM dithiothreitol] at 37° C. for 2 hours, followed by 5% polyacrylamide slab gel electrophoresis. After electrophoresis, the gel piece containing 0.25 kb DNA was sealed in a dialysis tube and the DNA fragment was eluted from the gel by the method described in Reference Example 1, followed by extraction with phenol and with ether. Thereafter, said DNA was recovered by ethanol precipitation.

3 μg of the plasmid pBR-Sal-6dT described in Example 14 was treated with 5 units of restriction enzyme Sal I and 5 units of restriction enzyme Xba I in 20 μl of a reaction mixture [50 mM Tris-HCl (pH 7.5), 100 mM NaCl, 10 mM MgCl₂, 1 mM dithiothreitol] at 37° C. for 2 hours, followed by 0.8% agarose slab gel electrophoresis. A 4.65 kb DNA fragment was separated and recovered from the gel by the above-mentioned method.

0.05 μg of the above 0.25 kb DNA fragment and 0.2 μg of the 4.65 kb DNA fragment were mixed together and ligation was carried out in the presence cf T4 DNA ligase under the conditions described in Reference Example 1. The reaction mixture was used for transformation of Escherichia coli DH1 and, from among the ampicillin-resistant transformants, a transformant carrying a plasmid, pBR-Sal-6cT, composed of the above two DNA fragment ligated together was isolated. Then, following the procedure described in Reference Example 1, the Hind III site of said plasmid pBR-Sal-6cT was converted to a Sal I site to give a plasmid, pBR-Sal-6cTS.

Figure 18:
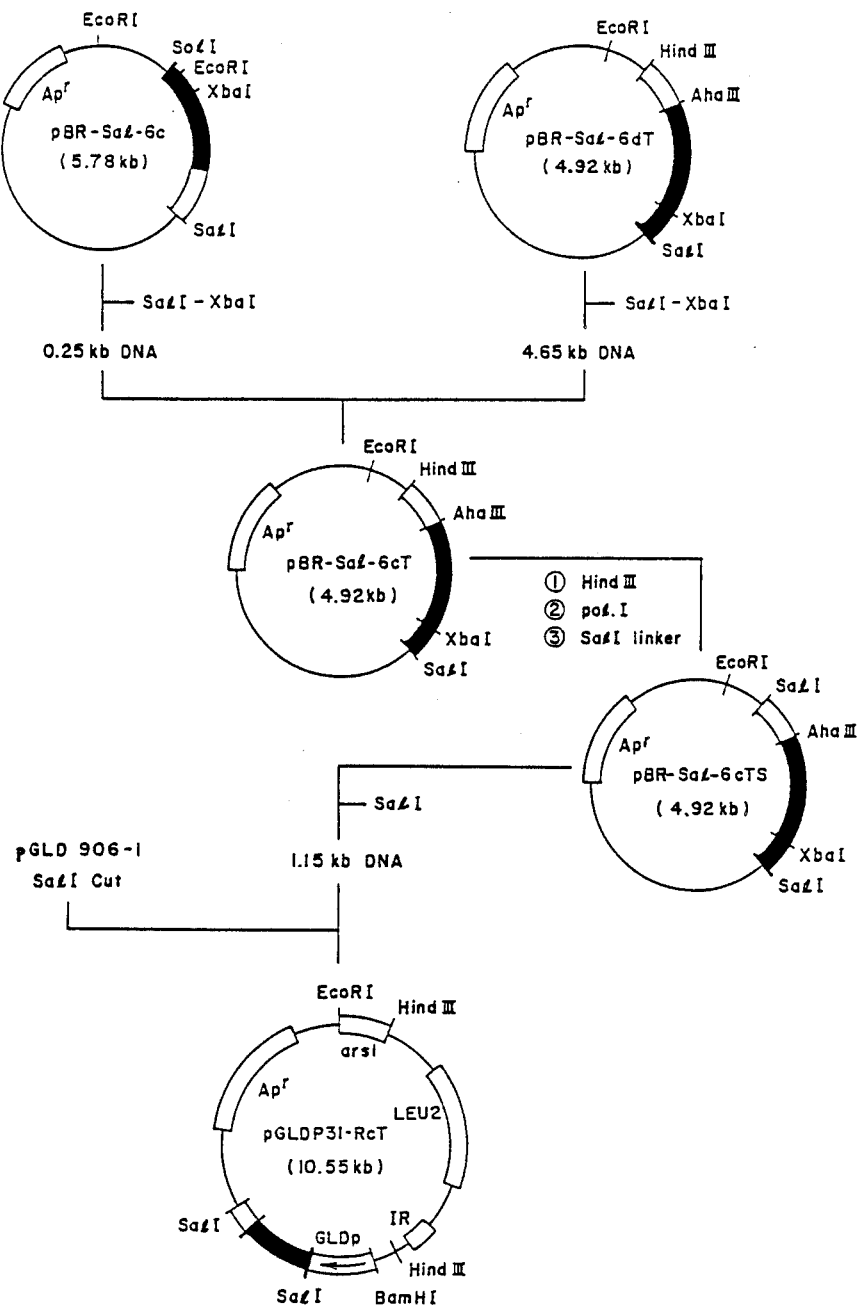
FIG. 18 shows the construction scheme for the plasmid pGLD P31-RcT.

5 μg of pBR-Sal-6cTS was treated with 10 units of restriction enzyme Sal I in 30 μl of a reaction mixture [50 mM Tris-HCl (pH 7.5), 100 mM NaCl, 10 mM MgCl₂, 1 mM dithiothreitol] at 37° C. for 2 hours. Then, a 1.15 kb DNA fragment was separated on agarose slab gel under the above-mentioned conditions and said DNA was recovered from the gel. 0.5 μg of said DNA was mixed with 0.1 μg of a DNA derived from the plasmid pGLD 906-1 by digestion with Sal I and ligation was effected using T4 DNA ligase. The reaction mixture was used for transformation of Escherichia coli DH1 to give ampicillin-resistant transformants. From one of said transformants, there was obtained a plasmid, pGLD P31-RcT, with the modified P31 gene-PGK terminator inserted therein the same directionality as that of the GLD promoter (FIG. 18).

Using pGLD P31-RcT, the yeast Saccharomyces cerevisiae AH22R⁻ was transformed and a transformant (AH22R⁻/pGLD P31-RcT) was isolated.

EXAMPLE 18

Expression of modified P31 gene in yeast

The yeast transformant carrying the modified P31 gene expression plasmid as obtained in Example 17 was cultured with shaking in 5 ml of a medium [containing, per liter 3 g K₂HPO₄, 30 g glucose, 4 g asparagine, 100 mg L-histidine, 0.1 mg KI, 500 mg MgSO₄·7H₂O, 330 mg CaCl₂·2H₂O, 0.4 mg CuSO₄·5H₂O, 2.5 mg FeSO₄·7H₂O, 0.4 mg MnSO₄·4H₂O, 0.2 mg (NH₄)₃PO₄·12MoO₃·3H₂O, 3.1 mg ZnSO₄·7H₂O, 10 mg inositol, 0.2 mg thiamine, 0.2 mg pyridoxine, 0.2 mg Ca pantothenate, 0.2 mg niacin and 0.002 mg biotin] at 30° C. for 1 day. Then, 2 ml of the culture broth was transferred to 18 ml of a fresh medium [containing, per liter, 300 mg KH₂PO₄, 50 g sucrose, 4 g asparagine, 100 mg L-histidine, 1.5 g KCl, 0.1 mg KI, 500 mg MgSO₄·7H₂O, 330 mg CaCl₂·2H₂O, 10 g glucose, 25 mM Tris-maleate (pH 6.5), 0.4 mg CuSO₄·5H₂O, 2.5 mg FeSO₄·7H₂O, 0.4 mg MnSO₄·4H₂O, 0.2 mg (NH₄)₃PO₄·12MoO₃·3H₂O, 3.1 mg ZnSO₄·7H₂O, 10 mg inositol, 0.2 mg thiamine, 0.2 mg pyridoxine, 0.2 mg Ca-pantothenate, 0.2 mg niacin and 0.002 mg biotin] and cultivation with shaking was further carried out at 30° C. for 2 days. Cells were harvested by centrifugation, and a cell extract was obtained by the procedure described in Example 5 and assayed for P31 activity. As a result, the P31 production by AH22R⁻/pGLD P31-RcT was calculated as 17.8 μg per milliliter of broth.

EXAMPLE 19

(1) Extraction from cells

Frozen and stored cells (500 g) of the yeast *Saccharomyces cerevisiae* AH22R−/pGLD P31-RcT as obtained by cultivation by the method described in Example 18 followed by freezing at −20° C. were uniformly suspended in 2,500 ml of a buffer (pH 7.2) containing 0.1% polyoxyethylene (20) sorbitan monooleate (Tween-80), 7.5 M urea, 10 mM tetrasodium ethylenediaminetetraacetate (EDTA), 2mM phenylmethylsulfonyl fluoride (PMSF), 0.1 mM (p-amidinophenyl) methanesulfonyl fluoride hydrochloride (P-APMSF) and 100 mM sodium phosphate. This suspension was treated in a Dynomill model KDL ball mill (WAB, Basel, Switzerland) at a flow rate of 4,000 ml/hr using glass beads of 0.50–0.75 mm to thereby disrupt cells continuously. For increasing the extraction efficiency, this procedure was repeated twice. Centrifugation of the extract at 13,900 ×g for 30 minutes gave 3,300 ml of a supernatant. The $HB_sAg$ concentration was 34.6 μg/ml as determined with Auszyme II.

(2) Fractionation with polyethylene glycol

To the supernatant obtained in the stove, there was added 0.65 volume of 33% (w/w) polyethylene glycol 6000 (PEG-6000) gradually, followed by adjustment of the pH to 6.0. The mixture was stirred for 30 minutes and, then, centrifuged at 13,900 ×g for 30 minutes to recover the HBsAg fraction as a sediment The sediment obtained was dissolved in 1,000 ml of a buffer (pH 7.2) containing 7.5 M urea, 10 mM EDTA, 2 mM PMSF, 0.1 mM P-APMSF and 100 mM sodium phosphate, and the pH was adjusted to 7.0, followed by addition of sodium chloride to a final concentration of 0.30 M. To this solution was added 0.25 volume of 33% (w/w) PEG-6000, and, after 30 minutes, centrifugation at 13,900 ×g was carried out for 30 minutes. To the thus-obtained supernatant, there was again added 0.29 volume of 33% (w/w) PEG-6000 and the pH was adjusted to 6.0, followed by stirring for 30 minutes. The mixture was centrifuged at 13,900 ×g for 30 minutes to collect a sediment. This sediment was dissolved in 120 ml of 5.0 M urea-0.145 M sodium chloride-5 mM EDTA-1 mM PMSF-0.05 mM P-APMSF-10 mM sodium phosphate buffer (pH 7.5).

(3) Gel filtration using Sephacryl S-300

A Sephacryl S-300 (Pharmacia, Sweden) column (5×102 cm, 2,000 ml) equilibrated with 5.0 M urea-0.145 M sodium chloride-5 mM EDTA-1 mM PMSF-0.05 mM P-APMSF-10 mM sodium phosphate buffer (pH 6.0) was loaded with the solution obtained in the above and elution was conducted with the same buffer. A 240 ml eluate fraction corresponding to the void volume of the column was collected.

(4) Antibody column 240 ml of the eluate obtained in the above was diluted five times with 0.145 M sodium chloride-5 mM EDTA-0.1 mM P-APMSF-10 mM sodium phosphate buffer (pH 6.0) and passed through the Formyl-Cellulofine column (200 ml) equilibrated with the same buffer, to which mouse derived-anti HBsAg antibody described in Reference Examples 1 to 3 of International Application No. PCT/JP85/00161 [Japanese Patent Application No. 4092/1986, filed Jan. 10, 1986] was bound. The HBsAg adsorbed-column was washed with 1 M ammonium thiocyanate-10 mM sodium phosphate buffer (pH 6.0) and elution was effected with 4 M ammonium thiocyate-10 mM sodium phosphate buffer (pH 6.0). About 300 ml of the eluate was concentrated to a volume of 40 ml.

(5) Gel filtration using Sephacryl S-400

A Sephacryl S-400 (Pharmacia, Sweden) column (5×102 cm, 2,000 ml) equilibrated with 5.0 M urea-0.145 M sodium chloride-5 mM EDTA-1 mM PMSF-0.05 mM P-APMSF-10 mM sodium phosphate buffer (pH 6.0) was loaded with the concentrate obtained in the above and elution was effected with the same buffer to collect 186 ml of an HBsAg fraction. The eluate was concentrated to a volume of 120 ml.

(6) Ultracentrifugation

On 8.5 ml of 40% cesium chloride (CsCl)-5M urea-2 mM EDTA-1 mM PMSF-0.05 mM P-APMSF-10 mM potassium phosphate buffer (pH 7.4) placed in a ultracentrifuge tube for Beckman SW-28, there was layered 8.5 ml of 30% CsCl-5 M urea-2 mM EDTA-1 mM PMSF-0.05 mM P-APMSF-10 mM potassium phosphate buffer (pH 7.4) and, further, 20 ml of the above solution was layered thereon. Ultracentrifugation was carried out at 28,000 rpm at 4° C. for 16 hours, whereby HBsAg was concentrated and purified in the vicinity of a density of about 1.2.

The concentrated and purified HBsAg fraction obtained by the above centrifugation was dialysed against PBS and passed through a membrane filter to give 50 ml of a purified HBsAg solution having an HBsAg protein concentration of 250 μg/ml.

EXAMPLE 20

The HBsAg obtained in Example 16 was investigated on the following properties:

(1) As a result of SDS-polyacrylamide slab gel electrophoresis by following the method of Laemmli [Nature 227, 680(1970)], and silver-staining, bands were detected at places corresponding to molecular weights of 37,000 and 34,000 daltons for the HBsAg protein.

(2) N-Terminal amino acid sequence

The N-terminal amino acid sequence was analysed by applying, to 74.2 μg of the HBsAg protein, the automatic Edman degradation method using a Gas-phase Protein Sequenator (Applied Biosystems Model 470A, USA). Phenylthiohydantion-amino acids (PTH-amino acids) were identified by high-performance liquid chromatography using a Micro Pak SP-ODS column (Varian, USA). The PTH-amino acids detected in the respective steps are shown in Table 4.

TABLE 4

| Step | Amino acid mainly detected |
|---|---|
| 1 | Met |
| 2 | Gln |
| 3 | Trp |
| 4 | x |
| 5 | x |
| 6 | x |
| 7 | x |
| 8 | Phe |
| 9 | His |
| 10 | Gln |
| 11 | Ala |
| 12 | Leu |
| 13 | Leu |
| 14 | Asp |

TABLE 4-continued

| Step | Amino acid mainly detected |
| --- | --- |
| 15 | Pro |

In the Table, x means unidentifiable amino acid.

(3) Observation by electron microscope

As a result of observation on the HBsAg particle by electron microscope (Nippon Denki, model 1200E), particles of 19.1±2.0 nm were observed.

It was identified that the HBsAg obtained in Example 19 had the same properties.

EXAMPLE 21

Construction 1 of plasmid capable of simultaneous expression of subtype adr modified P31 gene and subtype adw P25 gene 30 μg of the subtype adr modified P31 gene expression plasmid pPHO P31-Rc described in Example 3 was treated with 60 units of Sal I in 100 μl of a reaction mixture [50 mM Tris-HCl (pH 7.5), 100 mM NaCl, 10 mM MgCl$_2$, 1 mM dithiothreitol] at 37° C. for 10 minutes (partial digestion) and a 9.7 kb DNA fragment resulting from cleavage of one of the two Sal I sites occurring in the plasmid was separated by the method described in Reference Example 1 using agarose slab gel and recovered. 2 μg of this DNA fragment was treated with 4 units of restriction enzyme Sca I (New England Biolabs) in 20 μl of a reaction mixture [10 mM Tris-HCl (pH 7.5), 50 mM NaCl, 10 mM mgCl$_2$, 1 mM dithiothreitol] at 37° C. for 2 hours and the reaction mixture was subjected to agarose slab gel electrophoresis to separate a 6.85 kb DNA.

20 μg of the subtype adw P25 gene expression plasmid pPHO 17-58 described in the specification of Japanese Patent Application No. 193765/1984 [Japanese Unexamined Patent Publication No. 70989/1986] was treated with 40 units of restriction enzyme Bam HI (Nippon Gene) and 40 units of Hind III (Nippon Gene) in 100 μl of a reaction mixture [10 mM Tris-HCl (pH 7.5), 50 mM NaCl, 10 mM MgCl$_2$, 1 mM dithiothreitol] at 37° C. for 2 hours, and the reaction mixture was subjected to agarose slab gel electrophoresis to separate a 5.5 kb DNA. Then, 2 μg of this DNA fragment was treated with 5 units of DNA polymerase I large fragment (New England Biolabs) in 30 μl of a reaction mixture [40 mM potassium phosphate buffer (pH 7.5), 6.6 mM MgCl$_2$, 1 mM 2-mercaptoethanol, 33 μM dATP, 33 μM dGTP, 33 μM dTTP, 33 μM dCTP] to make the single-stranded portions at both ends of the DNA fragment double-stranded. 50 ng of the -Sal I linker phosphorylated at the 5′ end [5′-P-d(GGTCGACC)] (New England Biolabs) was ligated with 2 μg of the above blunt-ended DNA fragment using T4 DNA ligase. The reaction mixture was extracted with phenol and with ether, and NaCl was added to a concentration of 0.2 M. 2 volumes of cold ethanol was added and a DNA was precipitated at −20° C. 2 μg of said DNA fragment was treated with 10 units of restriction enzyme Sal I and 4 units of Sca I in 30 μl of a reaction mixture [50 mM Tris-HCl (pH 7.5), 10 mM NaCl, 10 mM MgCl$_2$, 1 mM dithiothreitol] at 37° C. for 3 hours and the reaction mixture was subjected to agarose slab gel electrophoresis to separate a 4.2 kb DNA fragment.

Figure 20:
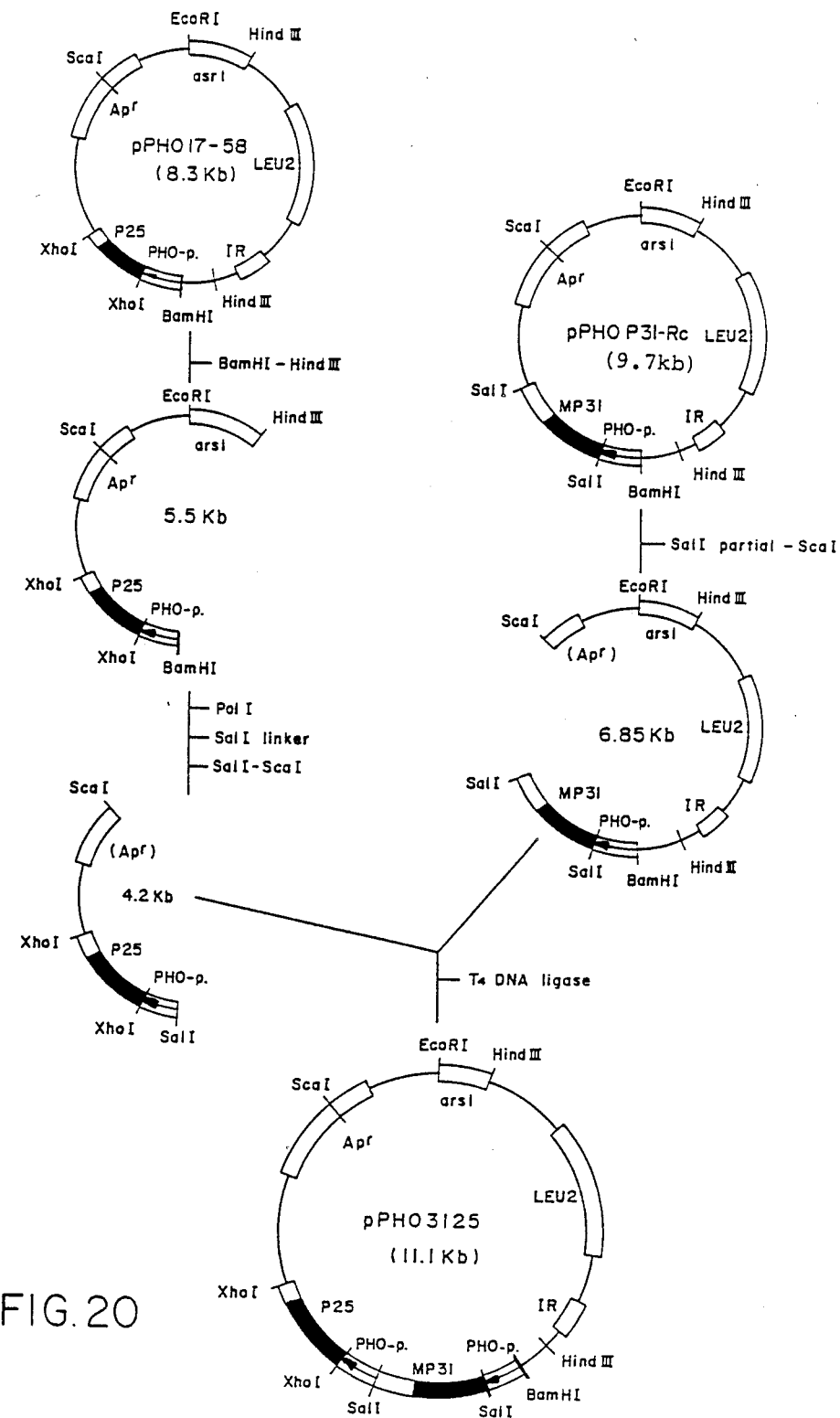
FIG. 20 shows the construction scheme for pPHO 3125.

0.5 μg of said 6.85 kb DNA fragment (derived from pPHO P31-Rc) and 0.5 μg of the 4.2 kb DNA fragment (derived from pPHO 17-58) were ligated together in 20 μl of a reaction mixture with use of T4 DNA ligase. The reaction mixture was used for transformation of *Escherichia coli* DH1 and pPHO 3125 was selected from ampicillin-resistant colonies by the miniscreening method [Birnboim, H.C. and Doly, J., Nucleic Acids Res., 7, 1513 (1979)](FIG. 20).

EXAMPLE 22

Construction 2 of plasmid capable of simultaneous expression of subtype adr modified P31 gene and subtype adw P25 gene.

30 μg of the subtype adw P25 gene expression plasmid pGLD P25-W described in Reference Example 6 was treated with 50 units of restriction enzyme Xho I (Nippon Gene) in 100 μl of a reaction mixture [50 mM Tris-HCl (pH 7.5) 100 mM NaCl, 10 mM MgCl$_2$, 1 mM dithiothreitol] at 37° C. for 10 minutes (partial digestion) and a 10.2 kb DNA fragment resulting from cleavage of one of the two Xho I sites occurring in the plasmid was separated by the method described in Reference Example 1 using agarose slab gel and recovered. 4 μg of this DNA fragment was treated with 4 units of restriction enzyme Sca I and the resulting 7.3 kb DNA fragment was separated on agarose slab gel and recovered. 1 μg of said DNA fragment was treated with DNA polymerase I large fragment by the method described in Example 21 to make the single-stranded DNA at one end resulting from Xho I digestion double-stranded.

20 μg of the subtype adr modified P31 gene expression plasmid pGLD P31-Rc described in Example 4 was treated with 40 units of restriction enzyme Sca I and 40 units of restriction enzyme Bam HI in 100 μl of a reaction mixture [10 mM Tris-HCl (pH 7.5), 50 mM NaCl, 10 mM MgCl$_2$, 1 mM dithiothreitol] at 37° C. for 2 hours and the reaction mixture was subjected to agarose slab gel electrophoresis to separate a 5.4 kb DNA fragment. 1 μg of said 5.4 kb DNA fragment was treated with DNA polymerase I large fragment by the method described in Example 21 to render the single-stranded DNA at one end resulting from Bam HI digestion double-stranded.

Figure 21:
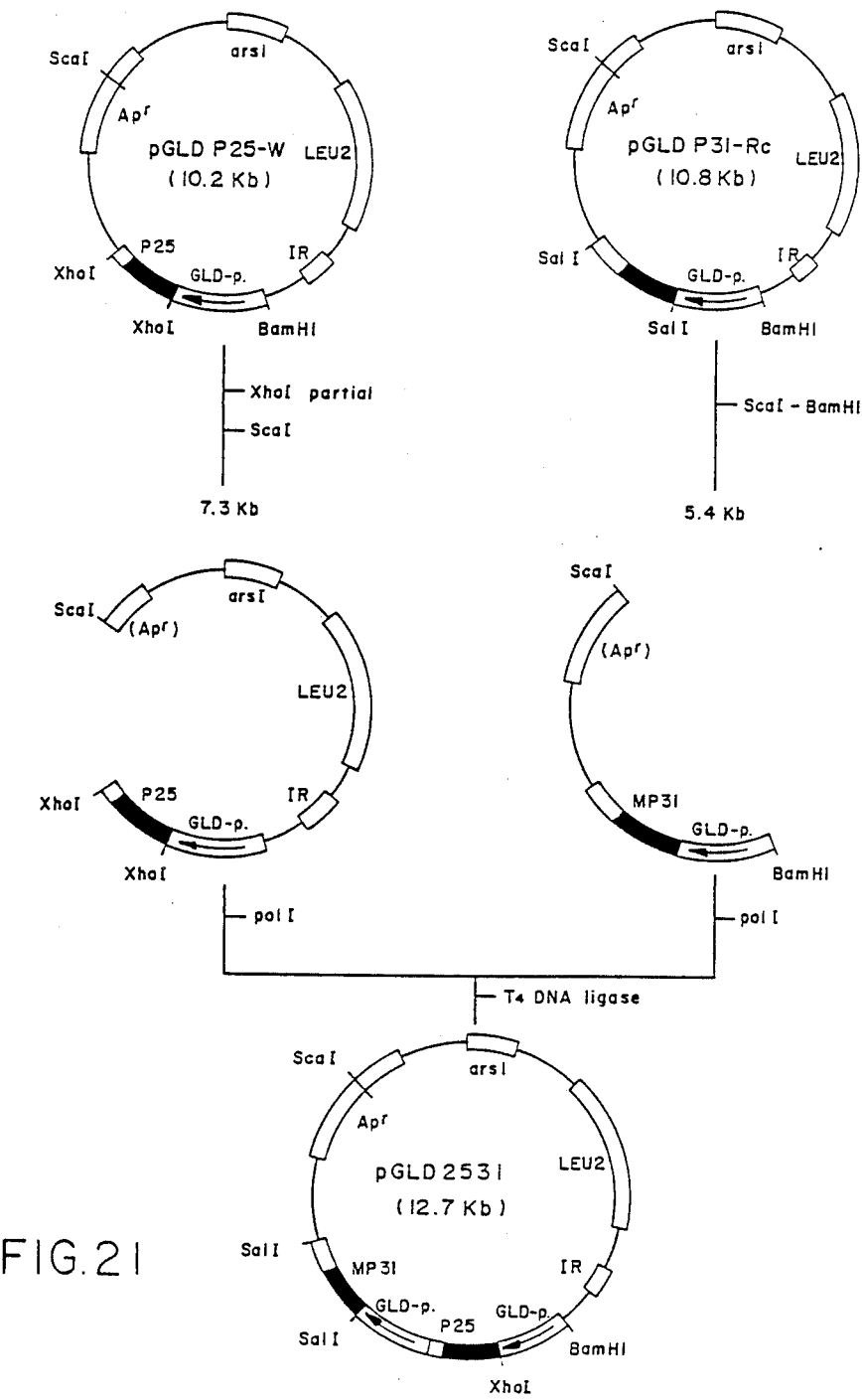
FIG. 21 shows the construction scheme for pGLD 2531.

0.5 μg of the above 7.3 kb DNA fragment (derived from pGLD P25-W) and 0.5 μg of the 5.4 kb DNA fragment (derived from pGLD P31-Rc) were ligated together in 20 μl of a reaction mixture using T4 DNA ligase. This reaction mixture was used for transformation of *Escherichia coli* DH1 and pGLD 2531 was separated from one of ampicillin-resistant colonies by the miniscreening method (FIG. 21).

EXAMPLE 23

Transformation of yeast with pPHO 3125 and pGLD 2531 and production of HBsAg with said transformants

*Saccharomyces cerevisiae* AH22R⁻ was transformed with 10 μg of pPHO 3125 described in Example 21 by a known method [Hinnen, A. et al., Proc. Natl. Acad. Sci. USA, 75, 1927 (1978)] to obtain a non-leucine-requiring transformant AH22R⁻/pPHO 3125. There was obtained AH22R⁻/pGLD 2531 by the same method using 10 μg of pGLD 2531 described in Example 22.

The yeast transformants carrying the above plasmids, capable of simultaneous expression of the subtype adr modified P31 gene and subtype adw P25 gene, were each cultivated in Burkholder's and his 5% sucrose-containing low phosphate media at 30° C. for 2 days. Thereafter, cells were harvested and washed with physiological saline.

The cells were converted to spheroplasts using Zymolyase (Seikagaku Kogyo) by the method of Miyanohara, A. et al. [Proc. Natl. Acad. Sci. USA, 80, 1 (1983)]. 0.1% Triton X-100 was then added to the spheroplasts for extraction of the HBsAg. The lysate was centrifuged at room temperature at 15,000 rpm for 15 minutes. The thus-obtained supernatant was measured for HBsAg activity using Auszyme II (Abbott). The results are shown in Table 5. Each HBsAg yield was calculated on the per-liter-of-broth basis.

TABLE 5

| Yeast transformant | HBsAg(μg/l broth) |
|---|---|
| Saccharomyces cerevisiae AH22R−/pPHO 3125 | 8,000 |
| Saccharomyces cerevisiae AH22R−/pGLD 2531 | 10,000 |

20 μl of said supernatant was subjected to SDS-polyacrylamide gel electrophoresis under reducing conditions [Laemmli, U.K., Nature, 227, 680 (1970)], and the protein was transferred onto a nitrocellulose membrane using a transblotting device (Bio-Rad). The testing for HBsAg using a peroxidase-labeled anti-HBsAg antibody (Auszyme II; Abbott) and an immune blot assay kit (Bio-Rad) revealed that the extract of AH22R−/pPHO 3125 contained an HBsAg protein of 37 kilodaltons (+trace amounts of 37 KD protein) and an HBsAg protein of 25 kilodaltons in the ratio of about 1:9. For the extract of AH22R−/pGLD 2531, an amount of the 37-kilodalton HBsAg protein (+trace amounts of 34 KD protein) was approximately equal to that of the 25-kilodalton HBsAg protein.

EXAMPLE 24

Construction 3 of plasmid capable of simultaneous expression of subtype adr modified P31 gene and subtype adw P25 gene 12 μg of the plasmid pGLD 906-1 described in Reference Example 3 was treated with 10 units of Bam HI and 10 units of Xho I in 50 μl of a reaction mixture [50 mM Tris-HCl (pH 7.5), 100 mM NaCl, 10 mM MgCl₂, 1 mM dithiothreitol] at 37° C. for 3 hours and the reaction mixture was subjected to 1 % agarose slab gel electrophoresis under the before-mentioned conditions. After electrophoresis, a 1.1 kb DNA fragment containing GLD promoter was recovered by the method described in Reference Example 1.

15 μg of the plasmid pPHO 17-58 described in Japanese Patent Unexamined Publication No. 70989/1986 was treated with 15 units of Xho I and 15 units of Aha III in a reaction mixture [50 mM Tris-HCl (pH 7.5), 100 mM NaCl, 10 mM MgCl₂, 1 mM dithiothreitol] at 37° C. for 3 hours, and the reaction mixture was subjected to 1.2% agarose slab gel electrophoresis under the before-mentioned conditions. After electrophoresis, there was recovered a 0.69 kb DNA fragment containing subtype adw P25 gene.

10 μg of the plasmid pBR-Sal-6cT described in Example 17 was treated with 8 units of Hind III and 8 units of Aha III in 30 μl of a reaction mixture [10 mM Tris-HCl (pH 7.5), 50 mM NaCl, 10 mM MgCl₂, 1 mM dithiothreitol] at 37° C. for 3 hours and the reaction mixture was subjected to 5% polyacrylanide slab gel electrophoresis. After electrophoresis, there was recovered a 0.29 kb DNA fragment containing PGK terminator.

3 μg of the plasmid pBR 322 was treated with 8 units of Hind III and 8 units of Bam HI in 20 μl of a reaction mixture [10 mM Tris-HCl (pH 7.5), 50 mM NaCl, 10 mM MgCl₂, 1 mM dithiothreitol] at 37° C. for 2 hours, and the reaction mixture was subjected to 0.8% agarose slab gel electrophoresis to recover a 4.02 kb DNA fragment.

Figure 22:
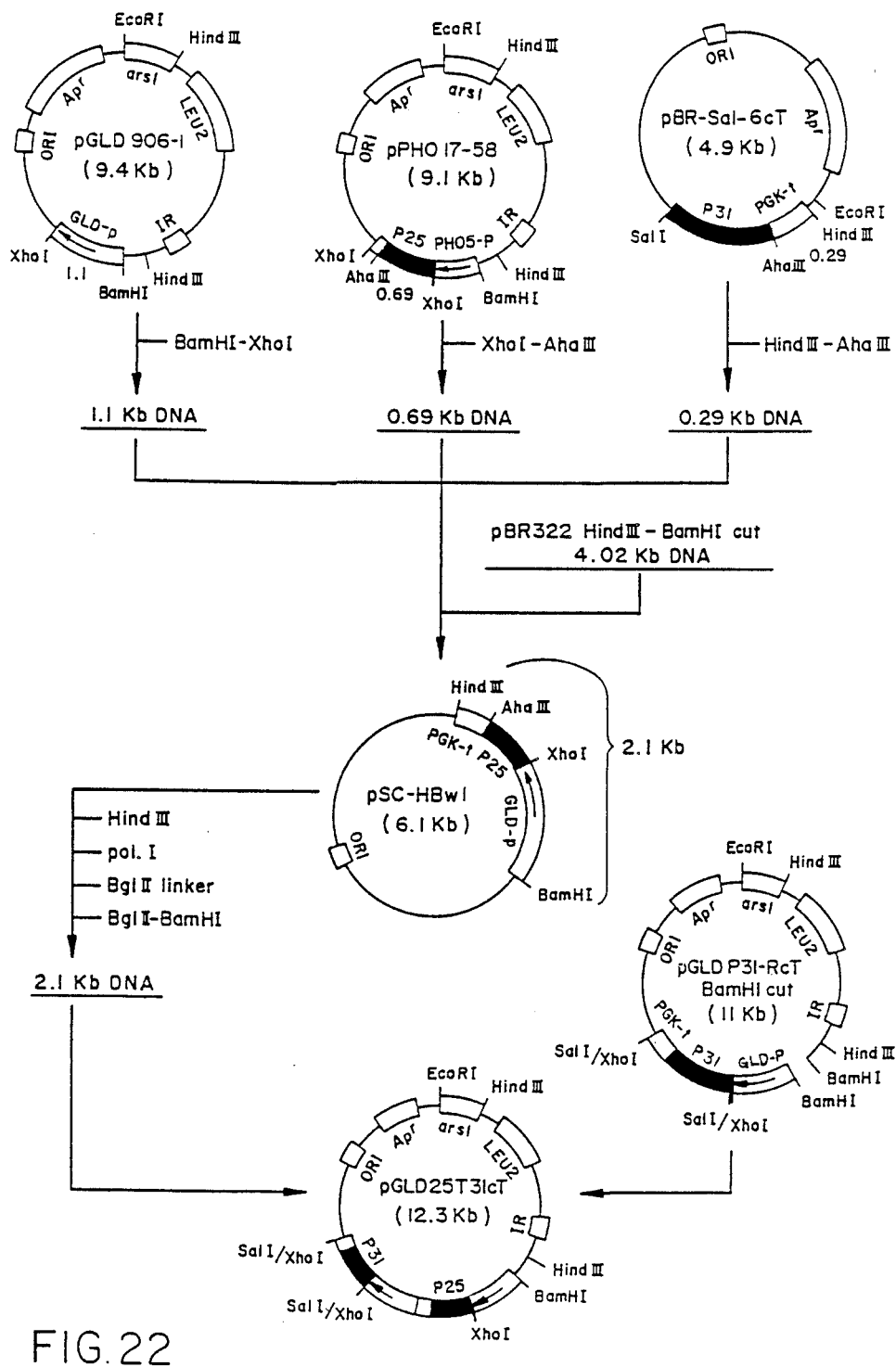
FIG. 22 shows the construction scheme for pGLD 25T31cT.

Four kinds of DNA fragments obtained by the above procedure were mixed together (0.1 μg of the 1.1 kb DNA fragment containing GLD promoter, 0.1 μg of the 0.69 kb DNA fragment containing adw P25 gene, 0.03 μg of the 0.29 kb DNA fragment containing PGK terminator and 0.2 μg of the 4.02 kb DNA fragment derived from pBR 322), and ligation was effected in 20 μl of a reaction mixture [66 mM Tris-HCl (pH 7.6), 6.6 mM MgCl₂, 10 mM dithiothreitol, 1 mM ATP] with 200 units of T4 DNA ligase at 14° C. for 16 hours. The reaction mixture was used for transformation of Escherichia coli DH1 to obtain ampicillin-resistant transformants. From one of said transformants, there was isolated a plasmid pSC-HBwl in which the GLD promoter, P25 gene adn PGK terminator were ligated (FIG. 22).

5 μg of the plasmid pSC-HBwl was digested with 4 units of Hind III in 20 μl of a reaction mixture at 37° C. for 3 hours to obtain a 6.1 kb DNA fragment. 5 μg of said DNA fragment was treated with 5 units of DNA polymerase I large fragment in 30 μl of a reaction mixture [40 mM potassium phosphate buffer (pH 7.5), 6.6 mM MgCl₂, 1 mM 2-mercaptoethanol, 33 μM dATP, 33 μM dGTP, 33 μM dTTP, 33 μM dCTP] to render the single-stranded portion at both ends of the DNA fragment double-stranded. To said DNA fragment was added 100 ng of a Bam HI linker phosphorylated at the 5' end [5'-CAGATCTG-3'] (New England Biolabs) and ligation was effected with T4 DNA ligase, followed by DNA precipitation with 2 volumes of ethanol. Said DNA was reacted with 8 units of Bam HI and 20 units of Bgl II in 30 μl of a reaction mixture [50 mM Tris-HCl (pH 7.5), 100 mM NaCl, 10 mM MgCl₂, 1 mM dithiothreitol] at 37° C. for 5 hours. The reaction mixture was subjected to 1% agarose slab gel electrophoresis to isolate a 2.1 kb DNA fragment.

0.2 μg of an 11 kb DNA fragment resulting from Bam HI digestion of the plasmid pGLD P31-RcT described in Example 17 and 0.2 μg of the above 2.1 kb DNA fragment were mixed and reacted with each other in 20 μl of a reaction mixture [66 mM Tris-HCl (pH 7.6), 6.6 mM MgCl₂, 10 mM dithiothreitol, 1 mM ATP] with use of 100 units of T4 DNA ligase at 14° C. for 16 hours. The reaction mixture was used for transformation of Escherichia coli DH1 tocbtain ampicillin-resistant transformants. There was obtained a plasmid, pGLD 25T31cT, from one of the transformants (FIG. 22).

EXAMPLE 25

Transformation of yeast with pGLD 25T31cT and HBsAg production with said transformant Yeast saccharomyces cerevisiae AH22R− was transformed with 10 μg of pGLD 25T31cT described in Example 24 [Hinnen, A. et al., Proc. Natl. Acad. Sci. USA, 75, 1927 (1978)] to obtain a transformant (AH22R−/pGLD 25T31cT).

The above transformant was cultured with shaking in 5 ml of a medium [containing, per liter, 3 g K₂HPO₄, 30 g glucose, 4 g asparagine, 100 mg L-histidine, 0.1 mg KI, 500 mg MgSO$_4$·7H$_2$O, 330 mg CaCl$_2$·2H$_2$O, 0.4 mg CuSO$_4$·5H$_2$O, 2.5 mg FeSO$_4$·7H$_2$O, 0.4 mg MnSO$_4$·4H$_2$O, 0.2 mg (NH$_4$)$_3$PO$_4$·12 MoO$_3$·3H$_2$O, 3.1 mg ZnSO$_4$·7H$_2$O, 10 mg inositol, 0.2 mg thiamine, 0.2 mg pyridoxine, 0.2 mg Ca-pantothenate, 0.2 mg niacin and 0.002 mg biotin] at 30° C. for a day. Then, 2 ml of the culture broth was transferred to 18 ml of a fresh medium [containing, per liter, 300 mg KH$_2$PO$_4$, 50 g sucrose, 4 g asparagine, 100 mg L-histidine, 1.5 g KCl, 0.1 mg KI, 500 mg MgSO$_4$·.7H$_2$O, 330 mg CaCl$_2$·2H$_2$O, 10 g glucose, 25 mM Trismaleate (pH 6.5), 0.4 mg CuSO$_4$·5H$_2$O, 2.5 mg FeSO$_4$·7H$_2$O, 0.4 mg MnSO$_4$·4H$_2$O, 0.2 mg (NH$_4$)$_3$PO$_4$. 12 MoO$_3$·3H$_2$O, 3.1 mg ZnSO$_4$·7H$_2$O, 10 mg inositol, 0.2 mg thiamine, 0.2 mg pyridoxine, 0.2 mg Ca-pantothenate, 0.2 mg niacin and 0.002 mg biotin] and cultivation with shaking was further carried out at 30° C. for 2 days. Cells were harvested by centrifugation and washed with physiological saline.

Cells were converted to spheroplasts by the method of Miyanohara, A. et al. [Proc. Natl. Acad. Sci. USA, 80, 1 (1983)] with Zymolyase [Seikagaku Kogyo], and 0.1% Triton X-100 was added to the spheroplasts, followed by extraction of HBsAg. The lysate was centrifuged at room temperature at 15,000 rpm for 15 minutes to obtain a supernatant. The assay for HBsAg activity of the supernatant by Auszyme II (Abbott) revealed that 20–30 mg of HBsAg was produced per liter of broth.

15 mg of the above cells were suspended in 100µl of a sample buffer [Laemmli, U. K., Nature, 227, 680 (1970)] and treated with heating at 100° C. for 10 minutes. 30 µl of the obtained supernatant was subjected to SDS-Polyacrylamide slab gel electrophoresis [Laemmli, U. K., Nature, 227, 680 (1970)], and the protein was transferred onto a nitrocellulose membrane using a transblotting device (Bio-Rad). The testing for HBsAg using a peroxidase-labeled anti-HBsAg antibody (Auszyme II; Abbott) and an immune blot assay kit (Bio-Rad) revealed that the proteins of 37, 34 and 25 kilodaltons were reacted with the anti-HBsAg antibody.

The microorganisms and animal cell lines that have been deposited with depository institutions are listed in Table 6 together with their deposit numbers.

In the table, IFO stands for Institute for Fermentation, Osaka and FRI for Fermentation Research Institute, Agency of Industrial Science and Technology, Ministry of International Trade and Industry, Japan, E. coli for Escherichia coli, and S. cerevisiae for Saccharomyces cerevisiae. The FERM BP numbers are deposit numbers under the Budapest Treaty.

TABLE 6

| Strain or cell line deposited | IFO (IFO) | FRI (FERM) |
|---|---|---|
| E. coli 294 | 14171 | |
| E. coli 294/pTRP P31-R | 14355 | BP-802 |
| E. coli C600 | 14410 | BP-808 |
| E. coli C600/pTRP P31-R | 14425 | BP-807 |
| S. cerevisiae AH22R⁻ | 10134 | BP-804 |
| S. cerevisiae AH22R⁻/pPHO P31-R | 10135 | BP-805 |
| S. cerevisiae AH22R⁻/pPHO P31-Ra | 10154 | BP-1060 |
| S. cerevisiae AH22R⁻/pGLD P31-RdT | 10172 | BP-1066 |
| S. cerevisiae AH22R⁻/pGLD P31-Rb | 10155 | BP-1061 |
| S. cerevisiae AH22R⁻/pGLD P31-Rc | 10156 | BP-1062 |
| S. cerevisiae AH22R⁻/pGLD P31-Rd | 10169 | BP-1063 |
| S. cerevisiae AH22R⁻/pGLD P31-RcT | 10206 | BP-1059 |
| S. cerevisiae AH22R⁻/pPHO 17-58 | 10137 | BP-854 |
| S. cerevisiae AH22R⁻/pPHO 3125 | 10171 | BP-1065 |
| S. cerevisiae AH22R⁻/pGLD 2531 | 10170 | BP-1064 |
| S. cerevisiae AH22R⁻/pGLD 25T31cT | 10208 | BP-1073 |

TABLE 6-continued

| Strain or cell line deposited | IFO (IFO) | FRI (FERM) |
|---|---|---|
| C-P31-558-1 | 50058 | |

E. coli 294 is a known strain [Backman, K. et al., Proc. Natl. Acad. Sci. U.S.A., 73, 4174 (1974)].

What is claimed is:

1. A DNA which contains a DNA sequence coding for a modified hepatitis B virus surface antigen P31 protein having hepatitis B virus surface antigenicity and the ability to bind polymerized human serum albumin, wherein:
   (a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, or
   (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and at least one amino acid residue selected from the group consisting of the 16th, 18th, 177th, and 196th amino acid residues from the N-terminus of a hepatitis B virus surface antigen P31 protein is replaced by an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine.

2. The DNA of claim 1, wherein
   (a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, or
   (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, and the 16th and 18th amino acid residues Arg from the N-terminus of a hepatitis B virus surface antigen P31 are replaced by Gln.

3. The DNA of claim 2, wherein the hepatitis B virus surface antigen P31 protein has the following amino acid sequence:

MetGlnTrpAsnSerThrThrPheHisGlnAla LeuLeuAspProArgValArgGlyLeuTyrPheProAlaGlyGlySerSerSer GlyThrValAsnProValProThrThrAlaSerProIleSerSerIlePheSer ArgThrGlyAspProAlaProAsnMetGluAsnThrThrSerGlyPheLeuGly ProLeuLeuValLeuGlnAlaGlyPhePheLeuLeuThrArgIleLeuThrIle ProGlnSerLeuAspSerTrpTrpThrSerLeuAsnPheLeuGlyGlyAlaPro ThrCysProGlyGlnAsnSerGlnSerProThrSerAsnHisSerProThrSer CysProProIleCysProGlyTyrArgTrpMetCysLeuArgArgPheIleIle PheLeuPheIleLeuLeuLeuCysLeuIlePheLeuLeuValLeuLeuAspTyr GlnGlyMetLeuProValCysProLeuLeuProGlyThrSerThrThrSerThr GlyProCysLysThrCysThrIleProAlaGlnGlyThrSerMetPheProSer CysCysCysThrLysProSerAspGlyAsnCysThrCysIleProIleProSer SerTrpAlaPheAlaArgPheLeuTrpGluTrpAlaSerValArgPheSerTrp LeuSerLeuLeuValProPheValGlnTrpPheValGlyLeuSerProThrVal TrpLeuSerValIleTrpMetMetTrpTyrTrpGlyProSerLeuTyrAsnIle LeuSerProPheLeuProLeuLeuProIlePhePheCysLeuTrpValTyrIle.

4. The DNA of claim 3, wherein the peptide chain covering the 44th to 49th amino acid residues from the N-terminus of the amino acid sequence is eliminated.

5. The DNA sequence of claim 1, which further comprises a DNA sequence coding for a heptatitis B virus surface antigen P25 protein.

6. The DNA of claim 1, which further comprises a terminator at the 3' end of the DNA sequence coding for the modified protein.

7. The DNA of claim 1, which is pGLD P31-Rc.

8. The DNA of claim 5, which is pGLD 2531.

9. The DNA of claim 6, which is pGLD P310-RcT.

10. A transformant carrying a DNA which contains a DNA (sequence coding for a modified heptatitis B virus surface antigen P31 protein having hepatitis B virus surface antigenicity and the ability to bind polymerized human serum albumin, wherein:

(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, or (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P3I protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and at least one amino acid residue selected from the group consisting of the 16th, 18th, 177th and 196th amino acid residues from the N-terminus of a hepatitis B virus surface antigen P31 protein is replaced by an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine.

11. The transformant of claim 10, wherein:

(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated on replaced by Trp or Pro-Asp-Pro-Gly, or (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, and the 16th and 18th amino acid residues Arg from the N-terminus of a hepatitis B virus surface antigen P31 are replaced by Gln.

12. The transformant of claim 11, wherein the hepatitis B virus surface antigen P31 protein has the following amino acid sequence:

MetGlnTrpAsnSerThrThrPheHisGlnAla LeuLeuAspProArgValArgGlyLeuTyrPheProAlaGlyGlySerSerSer GlyThrValAsnProValProThrThrAlaSerProIleSerSerIlePheSer ArgThrGlyAspProAlaProAsnMetGluAsnThrThrSerGlyPheLeuGly ProLeuLeuValLeuGlnAlaGlyPhePheLeuLeuThrArgIleLeuThrIle ProGlnSerLeuAspSerTrpTrpThrSerLeuAsnPheLeuGlyGlyAlaPro ThrCysProGlyGlnAsnSerGlnSerProThrSerAsnHisSerProThrSer CysProProIleCysProGlyTyrArgTrpMetCysLeuArgArgPheIleIle PheLeuPheIleLeuLeuLeuCysLeuIlePheLeuLeuValLeuLeuAspTyr GlnGlyMetLeuProValCysProLeuLeuProGlyThrSerThrThrSerThr GlyProCysLysThrCysThrIleProAlaGlnGlyThrSerMetPheProSer CysCysCysThrLysProSerAspGlyAsnCysThrCysIleProIleProSer SerTrpAlaPheAlaArgPheLeuTrpGluTrpAlaSerValArgPheSerTrp LeuSerLeuLeuValProPheValGlnTrpPheValGlyLeuSerProThrVal TrpLeuSerValIleTrpMetMetTrpTyrTrpGlyProSerLeuTyrAsnIle LeuSerProPheLeuProLeuLeuProIlePhePheCysLeuTrpValTyrIle.

13. The transformant of claim 12, wherein the peptide chain covering the 44th to 49th amino acid residues from the N-terminus of the amino acid sequence is eliminated.

14. The transformant of claim 10, which comprises a yeast.

15. The transformant of claim 10, which comprises a microorganism belonging to *Saccharomyces cerevisiae*.

16. The transformant of claim 13, which comprises *Saccharomyces cerevisiae* AH22R−/pPHO P31-Ra.

17. The transformant of claim 13, which comprises *Saccharomyces cerevisiae* AH22R−/pGLD P31-Rb.

18. The transformant of claim 13, which comprises *Saccharomyces cerevisiae* AH22R−/pGLD P31-Rc.

19. The transformant of claim 13, which comprises *Saccharomyces cerevisiae* AH22R⁻/pGLD P31-Rd.

20. The transformant of claim 13, which comprises *Sacharomyces cerevisiae* AH22R⁻/pGLD P31-RcT.

21. The transformant of claim 13, which comprises *Saccharomyces cerevisiae* AH22R⁻/pGLD P31-RdT.

22. The transformant of claim 13, which comprises *Saccharomyces cerevisiae* AH22R⁻/pPHO 3125.

23. The transformant of claim 13, which comprises *Saccharomyces cerevisiae* AH22R⁻/pGLD 2531.

24. The transformant of claim 13, which comprises *Saccharomyces cerevisiae* AH22R⁻/pGLD 25T31cT.

25. A method of producing a modified hepatitis B virus surface antigen P31 protein having hepatitis B virus surface antigenicity and the ability to bind polymerized human serum albumin, wherein:

(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, or (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and at least one amino acid residue selected form the group consisting of the 16th, 18th, 177th and 196th amino acid residues from the N-terminus of a hepatitis B virus surface antigen P31 protein is replaced by an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine, the method comprising the steps of culturing a transformant carrying a DNA which contains a DNA sequence coding for the modified P31 protein and recovering the modified P31 protein produced thereby.

26. The method of claim 25, wherein:

(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, or (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, and the 16th and 18th amino acid residues Arg from the N-terminus of a hepatitis B virus surface antigen P31 are replaced by Gln.

27. The method of claim 26, wherein the hepatitis B virus surface antigen P31 protein has the following amino acid sequence:

MetGlnTrpAsnSerThrThrPheHisGlnAla LeuLeuAspProArgValArgGlyLeuTyrPheProAla- GlyGlySerSerSer GlyThrValAsnProValProThr- ThrAlaSerProIleSerSerIlePheSer ArgThr- GlyAspProAlaProAsnMetGluAsnThrThrSerGly- PheLeuGly ProLeuLeuValLeuGlnAlaGlyPhe- PheLeuLeuThrArgIleLeuThrIle ProGlnSer- LeuAspSerTrpTrpThrSerLeuAsnPheLeuGly- GlyAlaPro ThrCysProGlyGlnAsnSerGlnSer- ProThrSerAsnHisSerProThrSer CysPro- ProIleCysProGlyTyrArgTrpMetCysLeuArgArg- PheIleIle PheLeuPheIleLeuLeuLeuCysLeuIle- PheLeuLeuValLeuLeuAspTyr GlnGlyMetLeu- ProValCysProLeuLeuProGlyThrSerThrTh- rSerThr GlyProCysLysThrCysThrIleProAlaGln- GlyThrSerMetPheProSer CysCysCysThrLys- ProSerAspGlyAsnCysThrCysIleProIleProSer SerTrpAlaPheAlaArgPheLeuTrpGluTrpAlaSer- ValArgPheSerTrp LeuSerLeuLeuValPro- PheValGlnTrpPheValGlyLeuSerProThrVal TrpLeuSerValIleTrpMetMetTrpTyrTrpGly- ProSerLeuTyrAsnIle LeuSerProPheLeu- ProLeuLeuProIlePhePheCysLeuTrpValTyrIle.

28. The method of claim 27, wherein the peptide chain covering the 44th to 49th amino acid residues from the N-terminus of the amino acid sequence is eliminated.

29. A method of producing (i) a hepatitis B virus surface antigen P25 protein, and (ii) a modified hepatitis B virus surface antigen P31 protein having hepatitis B virus surface antigenicity and the ability to find polymerized human serum albumin, wherein:

(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, or (b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and at least one amino acid residue selected form the group consisting of the 16th, 18th, 177th and 196th amino acid residues from the N-terminus of a hepatitis B virus surface antigen P31 protein is replaced by an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine, the method comprising the steps of culturing a transformant carrying a DNA which contains a DNA sequence coding for the modified P31 protein and a DNA sequence coding for the P25 protein and recovering the modified P31 protein and the P25 protein produced thereby.

30. The method of claim 29, wherein:
(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, or
(b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P3I protein is eliminated or replaced by Trp or Pro-Asp-Pro-Gly, and the 16th and 18th amino acid residues Arg from the N-terminus of a hepatitis B virus surface antigen P31 are replaced by Gln.

31. The method of claim 30, wherein the hepatitis B virus surface antigen P31 protein has the following amino acid sequence:

MetGlnTrpAsnSerThrThrPheHisGlnAla Leu-LeuAspProArgValArgGlyLeuTyrPheProAla-GlyGlySerSerSer GlyThrValAsnProValProThr-ThrAlaSerProIleSerSerIlePheSer ArgThr-GlyAspProAlaProAsnMetGluAsnThrThrSerGly-PheLeuGly ProLeuLeuValLeuGlnAlaGlyPhe-PheLeuLeuThrArgIleLeuThrIle ProGlnSer-LeuAspSerTrpTrpThrSerLeuAsnPheLeuGly-GlyAlaPro ThrCysProGlyGlnAsnSerGlnSer-ProThrSerAsnHisSerProThrSer CysPro-ProIleCysProGlyTyr.ArgTrpMetCysLeuAr-gArgPheIleIle PheLeuPheIleLeuLeuLeuCys-LeuIlePheLeuLeuValLeuLeuAspTyr GlnGlyMetLeuProValCysProLeuLeuProGlyTh-rSerThrThrSerThr GlyProCysLysThrCysThrIle-ProAlaGlnGlyThrSerMetPheProSer CysCys-CysThrLysProSerAspGlyAsnCysThrCysIle-ProIleProSer SerTrpAlaPheAlaArgPheLeuTrp-GluTrpAlaSerValArgPheSerTrp LeuSer-LeuLeuValProPheValGlnTrpPheValGlyLeuSer-ProThrVal TrpLeuSerValIleTrpMetMetTr-pTyrTrpGlyProSerLeuTyrAsnIle LeuSerPro-PheLeuProLeuLeuProIlePhePheCysLeuTrpVal-TyrIle.

32. The method of claim 30, wherein the peptide chain covering the 44th to 49th amino acid residues from the N-terminus of the amino acid sequence is eliminated.

33. A method of producing a transformant carrying a DNA which contains a DNA sequence coding for a modified hepatitis B virus surface antigen P31 protein having hepatitis B virus surface antigenicity and the ability to bind polymerized human serum albumin, wherein:

(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the M-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, or
(b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and at least one amino acid residue selected from the group consisting of the 16th, 18th, 177th and 196th amino acid residues from the N-terminus of a hepatitis B virus surface antigen P31 protein is replaced by an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine;

the method comprising the step of transforming a host with the DNA.

34. The method of claim 33, wherein:
(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, or
(b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Fro-Gly, and the 16th and 18th amino acid residues Arg from the N-terminus of a hepatitis B virus surface antigen P31 are replaced by Gln.

35. The method of claim 34, wherein the hepatitis B virus surface antigen P31 protein has the following amino acid sequence:

MetGlnTrpAsnSerThrThrPheHisGlnAla Leu-LeuAspProArgValArgGlyLeuTyrPheProAla-GlyGlySerSerSer GlyThrValAsnproValProThr-ThrAlaSerProIleSerSerIlePheSer ArgThr-GlyAspProAlaProAsnMetGluAsnThrThrSerGly-PheLeuGly ProLeuLeuValLeuGlnAlaGlyPhe-PheLeuLeuThrArgIleLeuThrIle ProGlnSer-LeuAspSerTrpTrpThrSerLeuAsnPheLeuGly-GlyAlaPro ThrCysProGlyGlnAsnSerGlnSer-ProThrSerAsnHisSerProThrSer CysPro- ProIleCysProGlyTyrArgTrpMetCysLeuArgArg-PheIleIle PheLeuPheIleLeuLeuLeuCysLeuIle-PheLeuLeuValLeuLeuAspTyr GlnGlyMetLeu-ProValCysProLeuLeuProGlyThrSerThrThrSerThr GlyProCysLysThrCysThrIleProAlaGln-GlyThrSerMetPheProSer CysCysCysThrLys-ProSerAspGlyAsnCysThrCysIleProIleProSer SerTrpAlaPheAlaArgPheLeuTrpGluTrpAlaSer-ValArgPheSerTrp LeuSerLeuLeuValPro-PheValGlnTrpPheValGlyLeuSerProThrVal TrpLeuSerValIleTrpMetMetTrpTyrTrpGly-ProSerLeuTyrAsnIle LeuSerProPheLeu-ProLeuLeuProIlePhePheCysLeuTrpValTyrIle.

36. The method of claim 35, wherein the peptide chain covering the 44th to 49th amino acid residues from the N-terminus of the amino acid sequence is eliminated.

37. The method of claim 28, wherein the host comprises a yeast.

38. The method of claim 33, wherein the host comprises *Saccharomyces cerevisiae*.

39. The method of claim 33, wherein the transformant comprises *Saccharomyces cerevisiae* AH22R⁻/pPHO P31-Ra.

40. The method of claim 33, wherein the transformant comprises *Saccharomyces cerevisiae* AH22R⁻/pGLD P31-Rb.

41. The method of claim 33, wherein the transformant comprises *Saccharomyces cerevisiae* AH22R⁻/pGLD P31-Rc.

42. The method of claim 33, wherein the transformant comprises *Saccharomyces cerevisiae* AH22R⁻/pGLD P31-Rd.

43. The method of claim 33, wherein the transformant comprises *Saccharomyces cerevisiae* AH22R⁻/pGLD P31-RcT.

44. The method of claim 33, wherein the transformant comprises *Saccharomyces cerevisiae* AH22R⁻/pGLD P31-RdT.

45. The method of claim 33, wherein the transformant comprises *Saccharomyces cerevisiae* AH22R⁻/pPHO 3125.

46. The method of claim 33, wherein the transformant comprises *Saccharomyces cerevisiae* AH22R⁻/pGLD 2531.

47. The method of claim 33, wherein the transformant is *Saccharomyces cerevisiae* AH22R⁻/pGLD 25T31cT.

48. A method of producing a DNA which contains a DNA sequence coding for a modified hepatitis B virus surface antigen P31 protein having hepatitis B virus surface antigenicity and the ability to bind polymerized human serum albumin, wherein:
(a) The 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, Valine, histidine, phenylalanine, proline, methionine and leucine, or
(b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and at least one amino acid residue selected form the group consisting of the 16th, 18th, 177th and 196th amino acid residues from the N-terminus of a hepatitis B virus surface antigen P31 protein is replaced by an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine, the method comprising the step of:
(i) eliminating a codon coding for the 48th amino acid residue Arg from the N-terminus of a hepatitis B virus surface antigen P31 protein or codons coding for a peptide containing the 48th amino acid residue Arg within the range of the peptide chain covering the 44th to 49th amino acid residues from the N-terminus of a hepatitis B virus surface antigen P31 protein or replacing the codon or codons by a codon coding for form one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline methionine and leucine, or
(ii) eliminating a codon coding for the 48th amino acid residue Arg from the N-terminus of a hepatitis B virus surface antigen P31 protein or codons coding for a peptide containing the 48th amino acid residue Arg within the range of the peptide chain covering the 44th to 49th amino acid residues from the N-terminus of a hepatitis B virus surface antigen P31 protein or replacing the codon or codons by from one to four amino acids selected from the group consisting of asparagine, aspartic acid, alanine, isoleucine, glycine, glutamine, glutamic acid, cysteine, serine, tyrosine, tryptophan, threonine, valine, histidine, phenylalanine, proline, methionine and leucine, and replacing at least one codon coding for at least one amino acid residue selected from the group consisting of the 16th, 18th, 177th and 196th amino acid residues from the N-terminus of a hepatitis B virus surface antigen P31 protein by a codon coding for an amino acid residue selected from asparagine, aspartic acid, alanine, isoleucine, glycine, glutamine, glutamic acid, cysteine, serine, tyrosine, tryptophan, threonine, valine, histidine, phenylalanine, proline, methionine and leucine.

49. The method of claim 48, wherein:
(a) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, or
(b) the 48th amino acid residue Arg from the N-terminus of a hepatitis B virus surface antigen P31 protein or a peptide containing the 48th amino acid residue Arg within the range of the peptide chain covering the 44th to 49th amino acid residues from the N-terminus of a hepatitis B virus surface antigen P31 protein is eliminated or replaced by Trp or Pro-Asp-Pro-Gly, and the 16th and 18th amino acid residues Arg from the N-terminus of a hepatitis B virus surface antigen P31 are replaced by Gln.

50. The method of claim 49, wherein the hepatitis B virus surface antigen P31 protein has the following amino acid sequence:

MetGlnTrpAsnSerThrThrPheHisGlnAla LeuLeuAspProArgValArgGlyLeuTyrPheProAlaGlyGlySerSerSer GlyThrValAsnProValProThrThrAlaSerProIleSerSerIlePheSer ArgThrGlyAspProAlaProAsnMetGluAsnThrThrSerGlyPheLeuGly ProLeuLeuValLeuGlnAlaGlyPhePheLeuLeuThrArgIleLeuThrIle ProGlnSerLeuAspSerTrpTrpThrSerLeuAsnPheLeuGlyGlyAlaPro ThrCysProGlyGlnAsnSerGlnSerProThrSerAsnHisSerProThrSer CysProProIleCysProGlyTyrArgTrpMetCysLeuArgArgPheIleIle PheLeuPheIleLeuLeuLeuCysLeuIlePheLeuLeuValLeuLeuAspTyr GlnGlyMetLeuProValCysProLeuLeuProGlyThrSerThrThrSerThr GlyProCysLysThrCysThrIleProAlaGlnGlyThrSerMetPheProSer CysCysCysThrLysProSerAspGlyAsnCysThrCysIleProIleProSer SerTrpAlaPheAlaArgPheLeuTrpGluTrpAlaSerValArgPheSerTrp LeuSerLeuLeuValProPheValGlnTrpPheValGlyLeuSerProThrVal TrpLeuSerValIleTrpMetMetTrpTyrTrpGlyProSerLeuTyrAsnIle LeuSerProPheLeuProLeuLeuProIlePhePheCysLeuTrpValTyrIle.

51. The method of claim 50, wherein the peptide chain covering the 44th to 49th amino acid residues from the N-terminus of the amino acid sequence is eliminated.

* * * * *